United States Patent
Gazit et al.

(10) Patent No.: US 12,185,635 B2
(45) Date of Patent: Dec. 31, 2024

(54) PIEZOELECTRIC PEPTIDE-BASED MATERIALS AND PIEZOELECTRIC DEVICES CONTAINING SAME

(71) Applicants: Ramot at Tel-Aviv University Ltd., Tel-Aviv (IL); Xidian University, Shaanxi (CN)

(72) Inventors: Ehud Gazit, Tel-Aviv (IL); Santu Bera, Tel-Aviv (IL); Yu Chen, Tel-Aviv (IL); Sharon Gilead, Tel-Aviv (IL); Kai Tao, Tel-Aviv (IL); Sigal Lazar, Tel-Aviv (IL); Rusen Yang, Xi'an (CN); Sudipta Mondal, Tel-Aviv (IL); Vasantha Basavalingappa, Tel-Aviv (IL)

(73) Assignees: Ramot at Tel-Aviv University Ltd., Tel-Aviv (IL); Xidian University, Xi'an (CN)

(*) Notice: Subject to any disclaimer, the term of this patent is extended or adjusted under 35 U.S.C. 154(b) by 50 days.

(21) Appl. No.: 17/442,765

(22) PCT Filed: Mar. 25, 2020

(86) PCT No.: PCT/IL2020/050357
§ 371 (c)(1),
(2) Date: Sep. 24, 2021

(87) PCT Pub. No.: WO2020/194304
PCT Pub. Date: Oct. 1, 2020

(65) Prior Publication Data
US 2022/0190232 A1 Jun. 16, 2022

Related U.S. Application Data

(60) Provisional application No. 62/823,128, filed on Mar. 25, 2019.

(51) Int. Cl.
| | | |
|---|---|---|
| H10N 30/857 | (2023.01) | |
| C07K 5/065 | (2006.01) | |
| C07K 5/083 | (2006.01) | |
| C07K 5/087 | (2006.01) | |
| C07K 5/097 | (2006.01) | |

(52) U.S. Cl.
CPC ....... *H10N 30/857* (2023.02); *C07K 5/06078* (2013.01); *C07K 5/0806* (2013.01); *C07K 5/0812* (2013.01); *C07K 5/0821* (2013.01); *C07K 5/0823* (2013.01)

(58) Field of Classification Search
None
See application file for complete search history.

(56) References Cited

U.S. PATENT DOCUMENTS

| | | | |
|---|---|---|---|
| 9,362,481 B2 | 6/2016 | Yu et al. | |
| 2014/0375172 A1* | 12/2014 | Hutchison | H10N 30/302 310/365 |

FOREIGN PATENT DOCUMENTS

| | | | | |
|---|---|---|---|---|
| WO | WO 2004/052773 | 6/2004 | | |
| WO | WO-2004052773 A2 * | 6/2004 | ......... | A61K 41/0052 |
| WO | WO 2004/060791 | 7/2004 | | |
| WO | WO 2006/013552 | 2/2006 | | |
| WO | WO 2006/027780 | 3/2006 | | |
| WO | WO-2006125324 A1 * | 11/2006 | .......... | A61K 31/404 |
| WO | WO 2007/043048 | 4/2007 | | |
| WO | WO 2008/068752 | 6/2008 | | |
| WO | WO 2011/151832 | 12/2011 | | |
| WO | WO 2014/132262 | 9/2014 | | |
| WO | WO 2014/178057 | 11/2014 | | |
| WO | WO-2016055810 A1 * | 4/2016 | ............. | A61K 38/06 |
| WO | WO 2017/068584 | 4/2017 | | |
| WO | WO 2019/012545 | 1/2019 | | |
| WO | WO 2020/194304 | 10/2020 | | |

OTHER PUBLICATIONS

Arnon et al. ("Opal-like Multicolor Appearance of Self-Assembled Photonic Array," ACS Appl Mater Interfaces. Jun. 02, 2018; 10(24): 20783-20789) (Year: 2018).*
Tao et al. "Quantum confined peptide assemblies with tunable visible to near-infrared spectral range," Nature Communications (2018) 9:3217, pp. 1-11 (Year: 2018).*
Amdursky et al. "Structural Transition in Peptide Nanotubes," Biomacromolecules 2011, 12, 1349-1354 (Year: 2011).*
Handelman et al. Reconstructive Phase Transition in Ultrashort Peptide Nanostructures and Induced Visible Photoluminescence, Langmuir 2016, 32, 2847-2862 (Year: 2016).*
International Search Report and the Written Opinion Dated Jun. 29, 2020 From the International Searching Authority Re. Application No. PCT/IL2020/050357. (11 Pages).
Bera et al. "Self-Assembly of Functional Nanostructures by Short Helical Peptide Building Blocks", Protein & Peptide Letters, 26(2): 88-97, Feb. 2019.
Chen et al. "Chiral Synthesis of D- and L-3, 3-Diphenylalanine (DIP), Unusual Alpha-Amino Acids for Peptides of Biological Interest", Tetrahedron Letters, 33(23): 3293-3296, Jun. 2, 1992.
Chen-Glasser et al. "Piezoelectric Materials for Medical Applications", Piezoelectricity—Organic and Inorganic Materials and Applications, Chap.7: 125-145, Aug. 29, 2018.
Chorsi et al. "Piezoelectric Biomaterials for Sensors and Actuators", Advanced Materials, 31(1): 1802084-1-1802084-15, Published Online Oct. 8, 2018.

(Continued)

*Primary Examiner* — Christina Bradley

(57) ABSTRACT

A piezoelectric transducer is provided herein, comprising a three-dimensional structure made of a plurality of peptides, the peptides being self-assembling and the structure being piezoelectric, wherein at least a portion, or each, of said plurality of peptides comprises peptides of 2 to 10 amino acid residues, provided that the plurality of peptides is not consisted of a plurality of Phe-Phe dipeptides. Further described herein are peptides having an amino acid sequence Hyp-Phe-Phe, Boc-Dip-Dip, (L)Trp-(D)Trp or (D)Trp-(L)Trp, as well as three-dimensional structures comprising such peptides.

15 Claims, 45 Drawing Sheets

(56) References Cited

OTHER PUBLICATIONS

Guerin et al. "Control of Piezoelectricity in Amino Acids by Supramolecular Packing", Nature Materials, 17(2): 180-186, Published Online Dec. 4, 2017.
Guerin et al. "Deconstructing Collagen Piezoelectricity Using Alanine-Hydroxyproline-Glycine Building Blocks", Nanoscale, 10(20): 9653-9663, Published Online May 8, 2018.
Handelman et al. "Reconstructive Phase Transition in Ultrashort Peptide Nanostructures and Induced Visible Photoluminescence", Langmuir, 32(12): 2847-2862, Published Online Oct. 23, 2015.
Jenkins et al. "Piezoelectric Diphenylalanine Peptide for Greatly Improved Flexible Nanogenerators", Nano Energy, 51: 317-323, Sep. 2018.
Kelly et al. "Conformational Dynamics and Aggregation Behavior of Piezoelectric Diphenylalanine Peptides in An External Electric Field", Biophysical Chemistry, 0: 16-24, Published Online Sep. 7, 2014.
Kholkin et al. "Strong Piezoelectricity in Bioinspired Peptide Nanotubes", ACS Nano, 4(2): 610-614, Published Online Feb. 4, 2010.
Knowles et al. "Nanomechanics of Functional and Pathological Amylois Materials", Nature Nanotechnology, 6(8): 469-479, Published Online Jul. 31, 2011.
Kol et al. "Self-Assembled Peptide Nanotubes Are Uniquely Rigid Bioinspired Supramolecular Structures", Nano Letters, 5(7): 1343-1346, Published on Web Jun. 8, 2005.
Liu et al. "A Comprehensive Review on Piezoelectric Energy Harvesting Technology: Materials, Mechanisms, and Applications", Applied Physics Reviews, 5(4): 041306-1-041306-36, Published Online Dec. 27, 2018.
Nguyen et al. "Epitaxial Growth of Vertically Aligned Piezoelectric Diphenylalanine Peptide Microrods With Uniform Polarization", Nano Energy, 17: 323-329, Available Online Sep. 6, 2015.
Nguyen et al. "Self-Assembly of Diphenylalanine Peptide With Controlled Polarization for Power Generation", Nature Communciations, 7: 13566-1-13566-6, Published Online Nov. 18, 2016.
Niu et al. "Using the Bending Beam Model to Estimate the Elasticity of Diphenylalanine Nanotubes", Langmuir, 23(14): 7443-7446, Published on Web Jun. 6, 2007.
Ryan et al. "Nanoscale Piezoelectric Properties of Self-Assembled Fmoc-FF Peptide Fibrous Networks", ACS Applied Materials & Interfaces, 7(23): 12702-12707, Published Online May 21, 2015.
Tabata et al. "Piezoelectric Property of Bundled Peptide Nanotubes Stapled by Bis-Cyclic-Beta-Peptide", Journal of Peptide Science, 25(1): e3134-1-e3134-6, Published Online Nov. 4, 2018.
Tao et al. "Bioinspired Stable and Photoluminescent Assemblies for Power Generation", Advanced Materials, 31(12): 1807481-1-1807481-7, Published Online Feb. 1, 2019.
Tao et al. "Stable and Optoelectronic Dipeptide Assemblies for Power Harvesting", Materials Today, 30: 19-16, Published Online Apr. 22, 2019.
Todaro et al. "Biocompatible, Felxible, and Compliant Energy Harvesters Based on Piezoelectric Thin Films", IEEE Transactions on Nanotechnology, 17(2): 220-230, Published Online Jan. 3, 2018.
Vasilev et al. "Piezoelectric Properties of Diphenylalanine Microtubes Prepared From the Solution", Journal of Physics and Chemistry of Solids, 93: 68-72, Available Online Feb. 11, 2016.

* cited by examiner

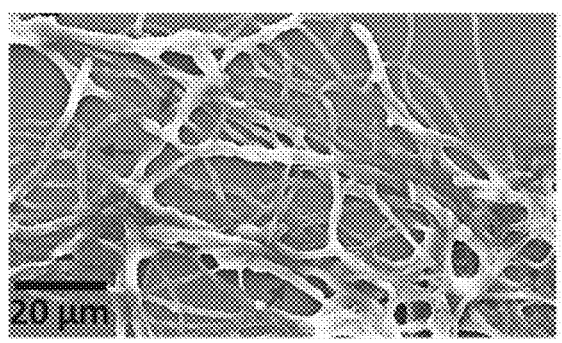
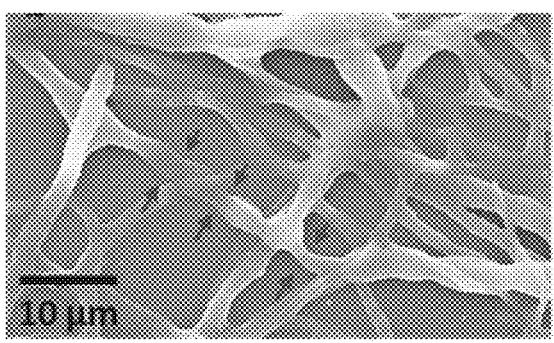
FIG. 1A　　　　　　　　　　FIG. 1B
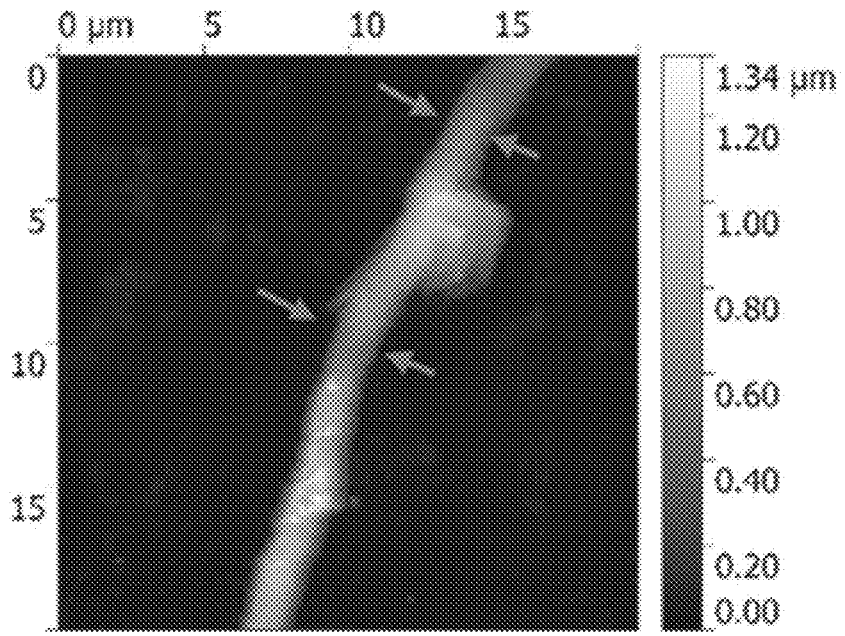
FIG. 1C
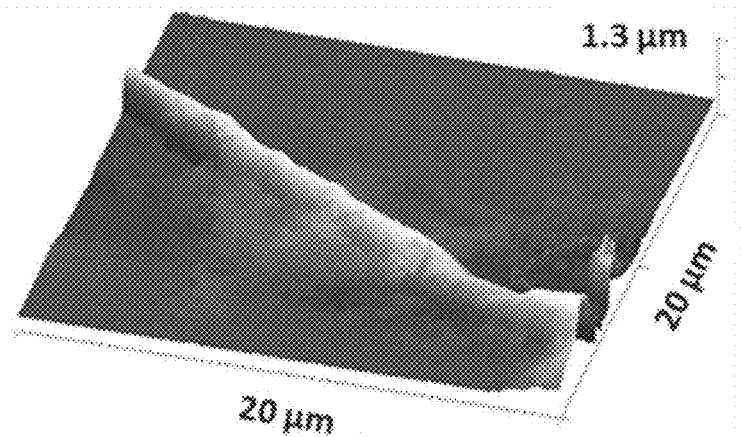
FIG. 1D

| Sequence | φ | ψ | Conformation |
|---|---|---|---|
| Pro-Phe-Phe | -78.5° | -38.9° | Cross-helix |
| Hyp-Phe-Phe | | | Cross-helix |
| Molecule A | -71.1° | -43.2° | |
| Molecule B | -70.5° | -41.9° | |
| Ala-Phe-Phe | | | Cross-beta |
| Molecule A | -144.20° | 150.81° | |
| Molecule B | -127.95° | 135.10° | |
| Ala-Phe-Ala | | | Cross-beta |
| Molecule A | -141.77° | 144.12° | |
| Molecule B | -140.72° | 130.43° | |

FIG. 15

FIG. 16
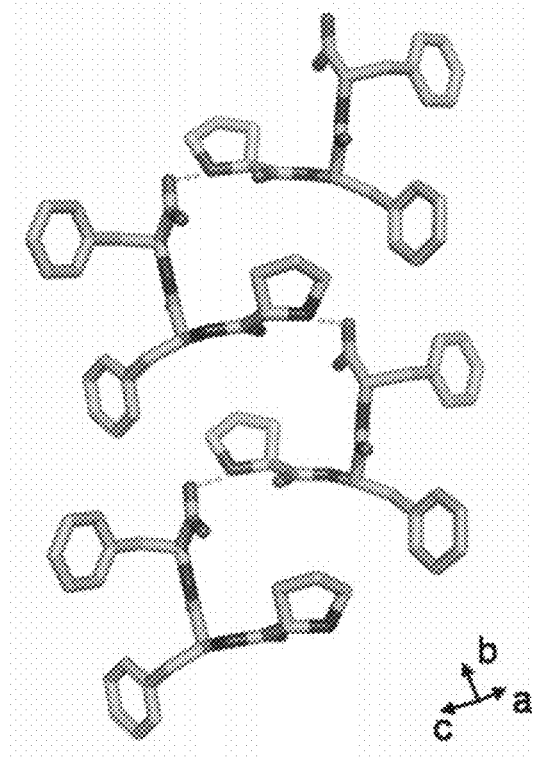
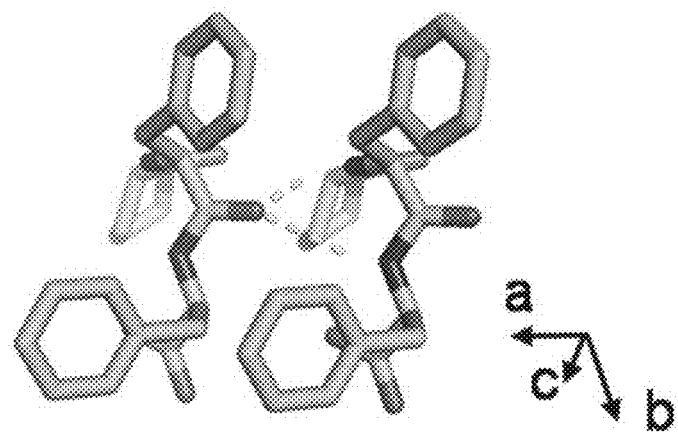
FIG. 17

FIG. 21
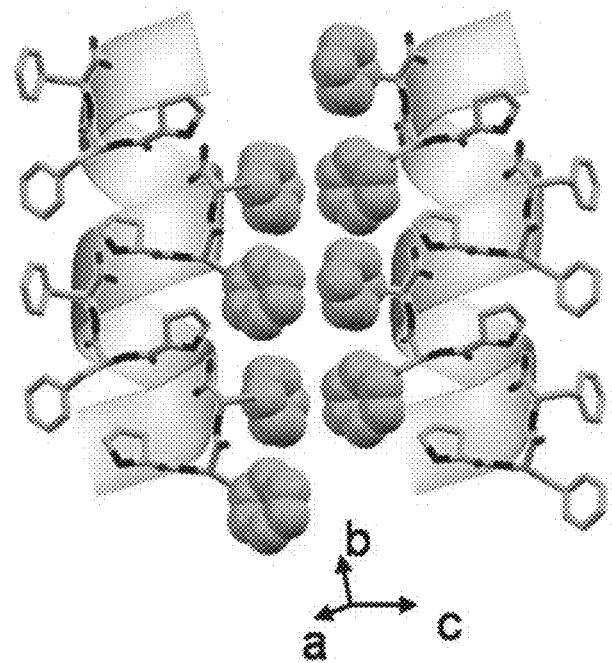
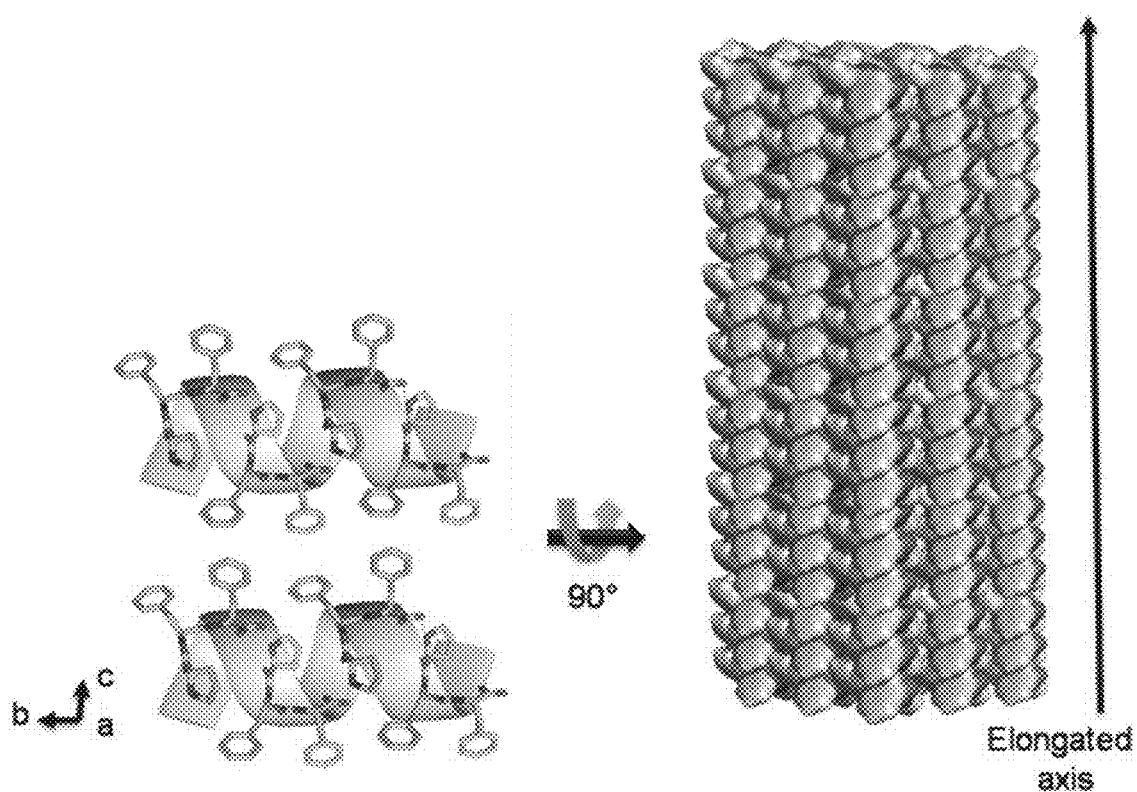
FIG. 22

FIG. 23B
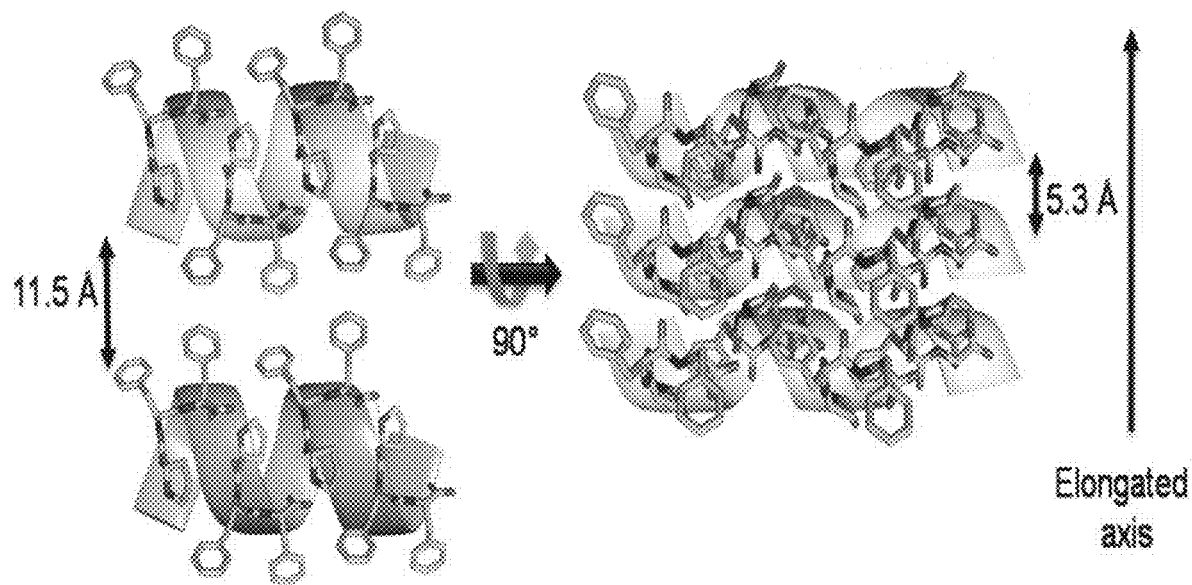
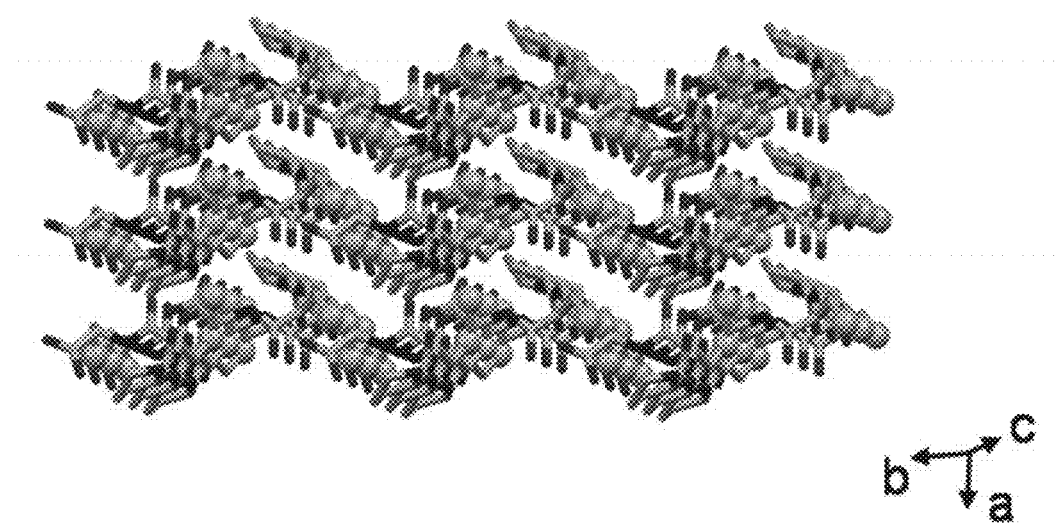
FIG. 23C

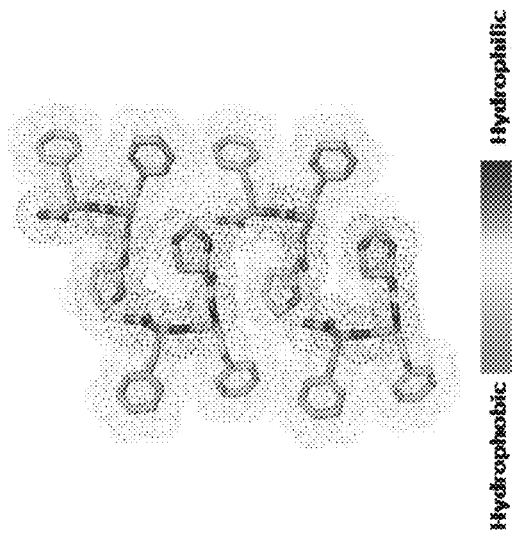
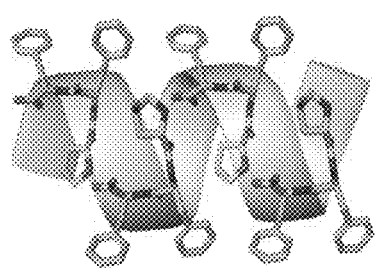
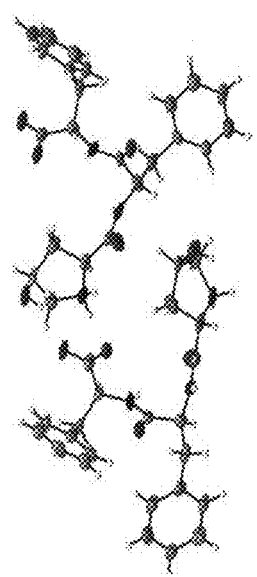
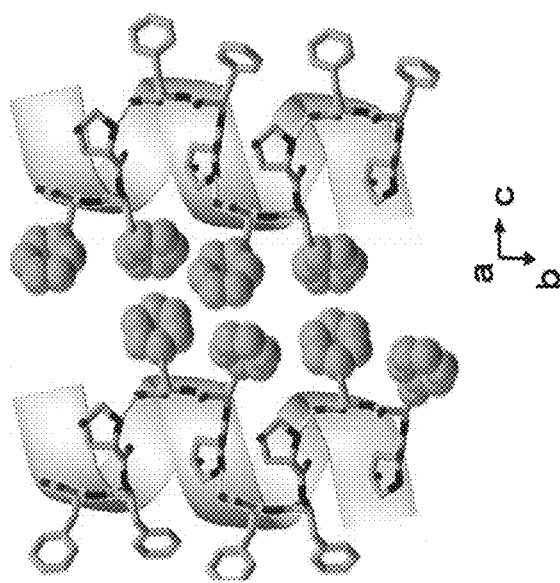
FIG. 24A
FIG. 24B
FIG. 24C

*Charge Tensor (C m⁻²)*

$$\begin{pmatrix} 0 & 0 & 0 & -0.006 & 0 & -0.0017 \\ -0.018 & 0.022 & -0.003 & 0 & -0.008 & 0 \\ 0 & 0 & 0 & 0 & 0 & -0.004 \end{pmatrix}$$

*Strain Tensor (pC N⁻¹)*

$$\begin{pmatrix} 0 & 0 & 0 & 0.12 & 0 & 1.16 \\ -1.58 & \boxed{3.48} & -0.31 & 0 & -3.14 & 0 \\ 0 & 0_{d_{22}} & 0 & 0 & 0 & 0.28 \end{pmatrix}$$

*Voltage Tensor (mV m N⁻¹)*

$$\begin{pmatrix} 0 & 0 & 0 & 5 & 0 & 43 \\ -59 & 129 & -12 & 0 & -117 & 0 \\ 0 & 0 & 0 & 0 & 0 & 10 \end{pmatrix}$$

FIG. 33A

*Charge Tensor (C m⁻²)*

$$\begin{pmatrix} -0.021 & 0.003 & -0.019 & 0.006 & 0.039 & -0.08 \\ 0.048 & -0.026 & 0.004 & 0.007 & 0 & 0 \\ -0.053 & 0.055 & -0.102 & -0.016 & 0.108 & -0.004 \end{pmatrix}$$

*Strain Tensor (pC N⁻¹)*

$$\begin{pmatrix} -2.20 & 2.20 & -1.79 & -3.55 & -10.96 & 26.67 \\ 5.04 & -19.3 & 0.38 & -4.14 & 0.28 & -1.00 \\ -5.57 & 4.07 & -9.59 & 9.47 & \boxed{-30.3}_{d_{35}} & 16.67 \end{pmatrix}$$

*Voltage Tensor (mV m N⁻¹)*

$$\begin{pmatrix} -86 & 86 & -70 & -139 & -429 & 1043 \\ 187 & -715 & 14 & -153 & 10 & -37 \\ -159 & 116 & -273 & 270 & -864 & 474 \end{pmatrix}$$

FIG. 33B

PIEZOELECTRIC PEPTIDE-BASED MATERIALS AND PIEZOELECTRIC DEVICES CONTAINING SAME

RELATED APPLICATIONS

This application is a National Phase of PCT Patent Application No. PCT/IL2020/050357 having International filing date of Mar. 25, 2020, which claims the benefit of priority under 35 USC § 119 (e) of U.S. Provisional Patent Application No. 62/823,128 filed on Mar. 25, 2019. The contents of which the above applications are all incorporated by reference as if fully set forth herein in their entirety.

The project leading to this application has received funding from the European Research Council (ERC) under the European Union's Horizon 2020 research and innovation programme grant agreement No. 694426.

FIELD AND BACKGROUND OF THE INVENTION

The present invention, in some embodiments thereof, relates to materials science, and more particularly, but not exclusively, to self-assembled structures formed of short peptides, which exhibit piezoelectric properties, and to uses thereof.

Piezoelectricity refers to the electric charge that accumulates in certain solid materials in response to mechanical stress. The piezoelectric effect is reversible—materials which generate a charge upon application of mechanical force also generate mechanical strain upon application of an electric field.

Piezoelectricity is exploited in various applications, such as production and detection of sound, piezoelectric inkjet printing, generation of high voltages, time reference sources (e.g., in quartz watches), amplification pickups (e.g., in guitars), electronic frequency generation, microbalances, ultrasonic nozzles, ultrafine focusing of optical assemblies, and scanning probe microscopic techniques.

20 of the 32 crystal classes exhibit piezoelectricity. Each of these 20 crystal classes is non-centrosymmetric, that is, they do not have inversion symmetry.

Lead zirconate titanate ($Pb[Zr_xTi_{1-x}]O_3$ where $0 \leq x \leq 1$), commonly referred to as "PZT" is a commonly used piezoelectric ceramic.

Bone, tendons, silk, wood, enamel, dentin, DNA and certain viral proteins are examples of biological materials which exhibit piezoelectric properties. Piezoelectric biomaterials and their uses are reviewed in Chorsi et al. [*Adv Mater* 31:e1802084 (2019)]

Nguyen et al. [*Nature Commun* 7:13566 (2016)] report that the random and unswitchable polarization of diphenylalanine (FF) peptide piezoelectricity has been an obstacle to utilization of its piezoelectricity, but that an effective piezoelectric constant $d_{33}$ of up to 17.9 pm/V was obtained upon application of an electric field during peptide self-assembly, and a peptide-based power generator produced an open-circuit voltage of 1.4 V and a power density of 3.3 $nM/cm^2$.

Additional background art includes Bera & Gazit [*Protein Pept Lett* 26:88-97 (2019)]; Guerin et al. [*Nat Mater* 17:180-186 (2018)]; Kelly et al. [*Biophys Chem* 196:16-24 (2015)]; Kholkin et al. [*ACS Nano* 4:610-614 (2010)]; Knowles & Buehler [*Nat Nanotechnol* 6:469-479 (2011)]; Kol et al. [*Nano Lett* 5:1343-1346 (2005)]; Nguyen et al. [*Nano Energy* 17:323-329 (2015)]; Niu et al. [*Langmuir* 23:7443-7446 (2007)]; Ryan et al. [*ACS Appl Mater Interfaces* 7:12702-12707 (2015)]; Tao et al. [*Adv Mater* 31:e1807481 (2019)]; Tao et al. [*Mater Today* (Kidlington) 30:10-16 (2019)]; Todaro et al. [*IEEE Transactions on Nanotechnology* 220-230 (2018)]; Vasilev et al. [*J Phys Chem Solids* 93:68-72 (2016)]; U.S. Pat. No. 9,362,481; U.S. Patent Application Publication No. 2014/0375172; and International Patent Applications having Publication Nos. WO 2004/052773, WO 2004/060791, WO 2006/027780, WO 2006/013552, WO 2007/043048, WO 2008/068752, WO 2011/151832, WO 2014/132262, 2014/178057, 2017/068584, and WO 2019/012545.

SUMMARY OF THE INVENTION

According to an aspect of some embodiments of the invention, there is provided a piezoelectric transducer comprising a three-dimensional structure made of a plurality of peptides, the peptides being self-assembling and the structure being piezoelectric, wherein at least a portion, or each, of the plurality of peptides comprises peptides of 2 to 10 amino acid residues, provided that the plurality of peptides is not consisted of a plurality of Phe-Phe dipeptides.

According to an aspect of some embodiments of the invention, there is provided an electronic device comprising a transducer according to any of the embodiments described herein relating to a transducer.

According to an aspect of some embodiments of the invention, there is provided a peptide having the amino acid sequence Hyp-Phe-Phe.

According to an aspect of some embodiments of the invention, there is provided a peptide having the amino acid sequence Boc-Dip-Dip, wherein Boc is an N-terminal tert-butoxycarbonyl group.

According to an aspect of some embodiments of the invention, there is provided a peptide having the amino acid sequence (L)Trp-(D)Trp or (D)Trp-(L)Trp.

According to an aspect of some embodiments of the invention, there is provided a three-dimensional structure made of a plurality of self-assembling peptides, wherein at least a portion, or each, of the plurality of peptides comprises a peptide according to any of the embodiments described relating to a peptide.

According to some of any of the embodiments described herein relating to a peptide, the peptide is in a three-dimensional structure made of a plurality of the peptides.

According to some of any of the embodiments described herein relating to a three-dimensional structure, the structure is a piezoelectric structure.

According to some of any of the embodiments described herein relating to a three-dimensional structure, the structure is characterized by a non-centrosymmetric unit cell.

According to some of any of the embodiments described herein relating to a three-dimensional structure, the three-dimensional structure is a crystalline form.

According to some of any of the embodiments described herein relating to a plurality of peptides, at least a portion, or each, of the plurality of peptides comprises 2 or 3 amino acid residues.

According to some of any of the embodiments described herein relating to a plurality of peptides, at least one of the amino acid residues comprises an aromatic moiety.

According to some of any of the embodiments described herein relating to a plurality of peptides, the peptides comprise at least two adjacent amino acid residues which each comprise an aromatic moiety.

According to some of any of the embodiments described herein relating to a plurality of peptides, at least one of the amino acid residues is a residue of an amino acid selected from the group consisting of phenylalanine (Phe), tyrosine (Tyr), tryptophan (Trp), histidine (His), β,β-diphenylalanine (Dip), naphthylalanine (Nal), and dihydroxyphenylalanine (DOPA).

According to some of any of the embodiments described herein relating to a plurality of peptides, the peptides comprise at least two adjacent amino acid residues which are each independently a residue of an amino acid selected from the group consisting of phenylalanine (Phe), tyrosine (Tyr), tryptophan (Trp), histidine (His), β,β-diphenylalanine (Dip), naphthylalanine (Nal), and dihydroxyphenylalanine (DOPA).

According to some of any of the embodiments described herein relating to a plurality of peptides, the peptides comprise at least one amino acid residue which comprises a plurality of non-fused aromatic moieties.

According to some of any of the embodiments described herein relating to a plurality of peptides, the peptides comprise at least two adjacent amino acid residues which each independently comprise a plurality of non-fused aromatic moieties.

According to some of any of the embodiments described herein relating to a peptide which comprises a plurality of non-fused aromatic moieties, the at least one amino acid residue which comprises a plurality of non-fused aromatic moieties comprises a Dip residue.

According to some of any of the embodiments described herein relating to a plurality of peptides, the peptides comprise at least one non-coded amino acid residue.

According to some of any of the embodiments described herein relating to a plurality of peptides, at least a portion, or each, of the plurality of peptides has a helical secondary structure.

According to some of any of the embodiments described herein relating to a helical secondary structure, the helical secondary structure is characterized by at least one amino acid residue having dihedral angles of psi ($\psi$) in a range of from −100° to 45° and phi ($\phi$) in a range of from −180° to 15°.

According to some of any of the embodiments described herein relating to peptides which have a helical secondary structure, the peptides comprise an amino acid sequence selected from the group consisting of Pro-Phe-Phe and Hyp-Phe-Phe.

According to some of any of the embodiments described herein relating to a plurality of peptides, at least a portion, or each, of the plurality of peptides is a tripeptide.

According to some of any of the embodiments described herein relating to a plurality of peptides, at least a portion, or each, of the plurality of peptides is a cyclic peptide.

According to some of any of the embodiments described herein relating to a cyclic dipeptide, the cyclic peptide is a cyclic dipeptide.

According to some of any of the embodiments described herein relating to a cyclic dipeptide, the cyclic peptide is selected from the group consisting of cyclo-Phe-Phe, cyclo-Gly-Trp and cyclo-Phe-Trp.

According to some of any of the embodiments described herein relating to a plurality of peptides, each of the amino acid residues in the peptides is an L-amino acid residue or each of the amino acid residues in the peptides is a D-amino acid residue.

According to some of any of the embodiments described herein relating to a plurality of peptides, at least a portion, or each, of the plurality of peptides is selected from the group consisting of (L)Pro-(L)Phe-(L)Phe, (D)Pro-(D)Phe-(D)Phe, (L)Hyp-(L)Phe-(L)Phe, (D)Hyp-(D)Phe-(D)Phe, Boc-(L)Dip-(L)Dip, Boc-(D)Dip-(D)Dip, (L)Trp-(D)Trp, (D)Trp-(L)Trp, Gly-Trp, cyclo-(L)Phe-(L)Phe, cyclo-(D)Phe-(D)Phe, cyclo-Gly-(L)Trp, cyclo-Gly-(D)Trp, cyclo-(L)Phe-(L)Trp, and cyclo-(D)Phe-(D)Trp.

According to some of any of the embodiments described herein relating to a plurality of peptides, at least a portion, or each, of the plurality of peptides is selected from the group consisting of (L)Pro-(L)Phe-(L)Phe, (D)Pro-(D)Phe-(D)Phe, Boc-(L)Dip-(L)Dip, Boc-(D)Dip-(D)Dip, (L)Trp-(D)Trp, (D)Trp-(L)Trp, cyclo-Gly-(L)Trp, cyclo-Gly-(D)Trp, cyclo-(L)Phe-(L)Trp, and cyclo-(D)Phe-(D)Trp.

According to some of any of the embodiments described herein relating to a transducer, the transducer is configured to transform a mechanical input to an electronic output.

According to some of any of the embodiments described herein relating to a transducer, the transducer is configured to transform an electronic input to a mechanical output.

According to some of any of the embodiments described herein relating to an electronic device, the device is a medical implant.

According to some of any of the embodiments described herein relating to an electronic device, the transducer functions as a power source for the device.

According to some of any of the embodiments described herein relating to an electronic device, the transducer functions as a sensor, a monitor, an energy source, and/or a cell and/or tissue regenerator.

According to some of any of the embodiments described herein relating to an electronic device, the device is selected from the group consisting of a generator, a pacemaker, a vital-signs monitor, an ultrasound wand, artificial skin, a temperature sensor, and an ear implant.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1D present high resolution scanning electron microscopy (HR-SEM) images (FIGS. 1A and 1B) and atomic force microscopy images (FIGS. 1C and 1D) of amyloid-like fibrillar assembly of Pro-Phe-Phe tripeptide prepared in phosphate buffer at pH 7.4 (arrows indicate the helical nature of the fibers).

FIG. 15 presents a table of $Phe_2$ torsion angles of exemplary tripeptides.

FIG. 16 presents an image depicting head-to-tail hydrogen bonds (viewed approximately along the b-axis) of Pro-Phe-Phe in a single crystal structure.

FIG. 17 presents an image depicting side-by-side stacking of Pro-Phe-Phe in a single crystal structure through amide hydrogen bonds along the a-axis.

FIG. 21 presents an image depicting an aromatic zipper-like molecular packing of the adjacent helical assemblies along the c-direction of a Pro-Phe-Phe crystal structure (peptide helix is superimposed over an ideal helical model).

FIG. 22 presents an image schematically depicting formation of an elongated structure by stacking of helices through intermolecular hydrogen bonds along the a-direction of a Pro-Phe-Phe crystal structure (peptide helix is superimposed over an ideal helical model).

FIGS. 23A-23C presents images depicting a crystal structure of PSMα3 and the central core Lys-Phe-Phe residues (PDB code 5i55 [Tayeb-Fligelman et al., *Science* 355:831-833 (2017)]) (FIG. 23A), formation of a helical sheet and interaction between adjacent sheets in the crystal packing of Pro-Phe-Phe (inter-sheet and inter-strand distances are shown) (FIG. 23B), and a cross-helical arrangement of Pro-Phe-Phe in the crystallographic ab plane (the aromatic ring of the Phe residue is represented as a sphere) (FIG. 23C).

FIGS. 24A-24C present images depicting a Hyp-Phe-Phe crystal structure as an ORTEP diagram (FIG. 24A) of the asymmetric unit in 50% probability displacement ellipsoids in which the asymmetric unit of Hyp-Phe-Phe comprised two molecules and shared a common H-bonding pattern, as a single helix in the crystallographic b-direction represented by colors according to hydrophobicity (FIG. 24B), and as an aromatic zipper-like structural organization of Hyp-Phe-Phe in the be plane (FIG. 24C).

FIGS. 33A and 33B present calculated piezoelectric tensors for Pro-Phe-Phe (FIG. 33A) and Hyp-Phe-Phe (FIG. 33B).

DETAILED DESCRIPTION OF SPECIFIC EMBODIMENTS OF THE INVENTION

Figure 2A:
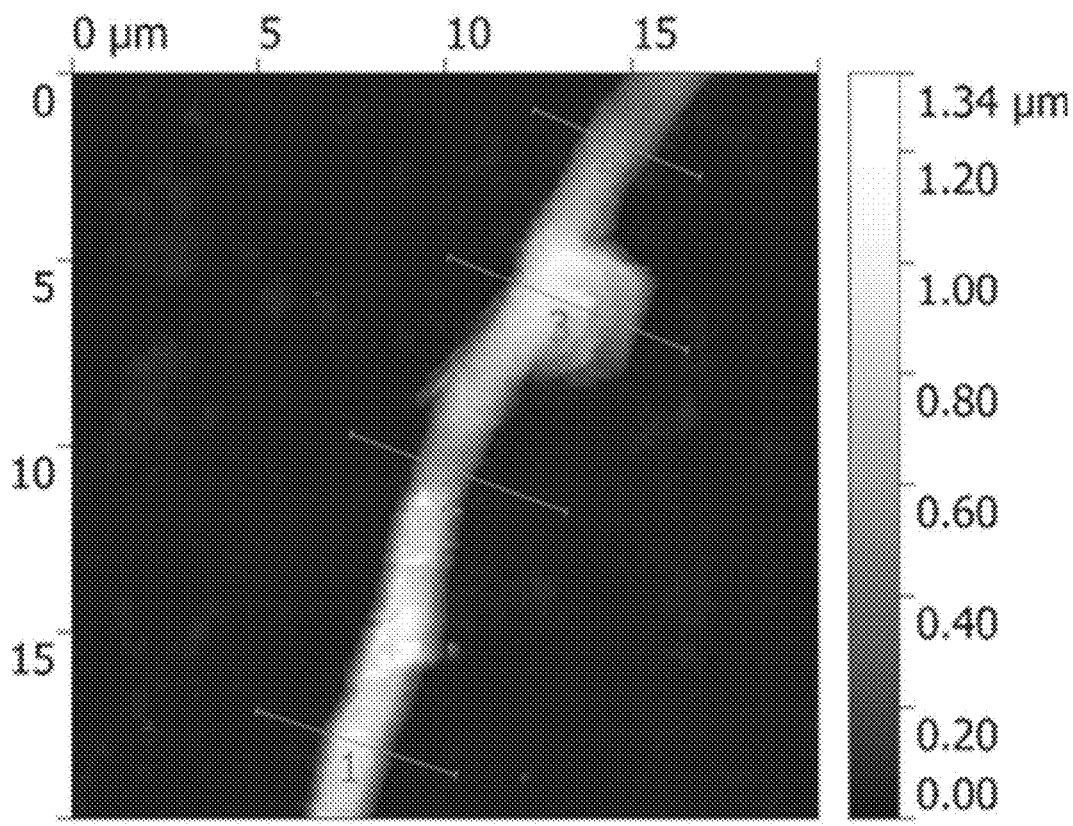
FIGS. 2A-2D present atomic force microscopy images (FIGS. 2A and 2C) of individual Pro-Phe-Phe fibers, and graphs (FIGS. 2B and 2D) showing height profiles of the fibers shown in FIGS. 2A and 2C (along the lines depicted therein crossing each fiber), respectively; the height profiles of the fibers exhibit nearly identical spatial fluctuation along the fiber axis at a regular interval, confirming their helical nature.
Figure 2B:
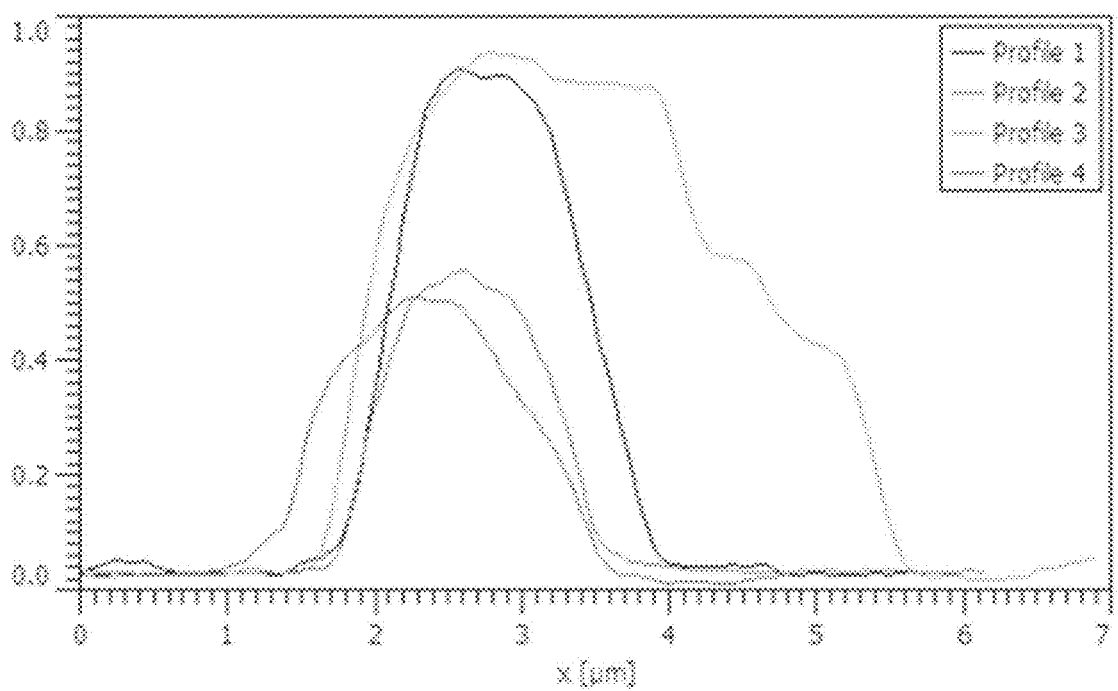
Figure 2C:
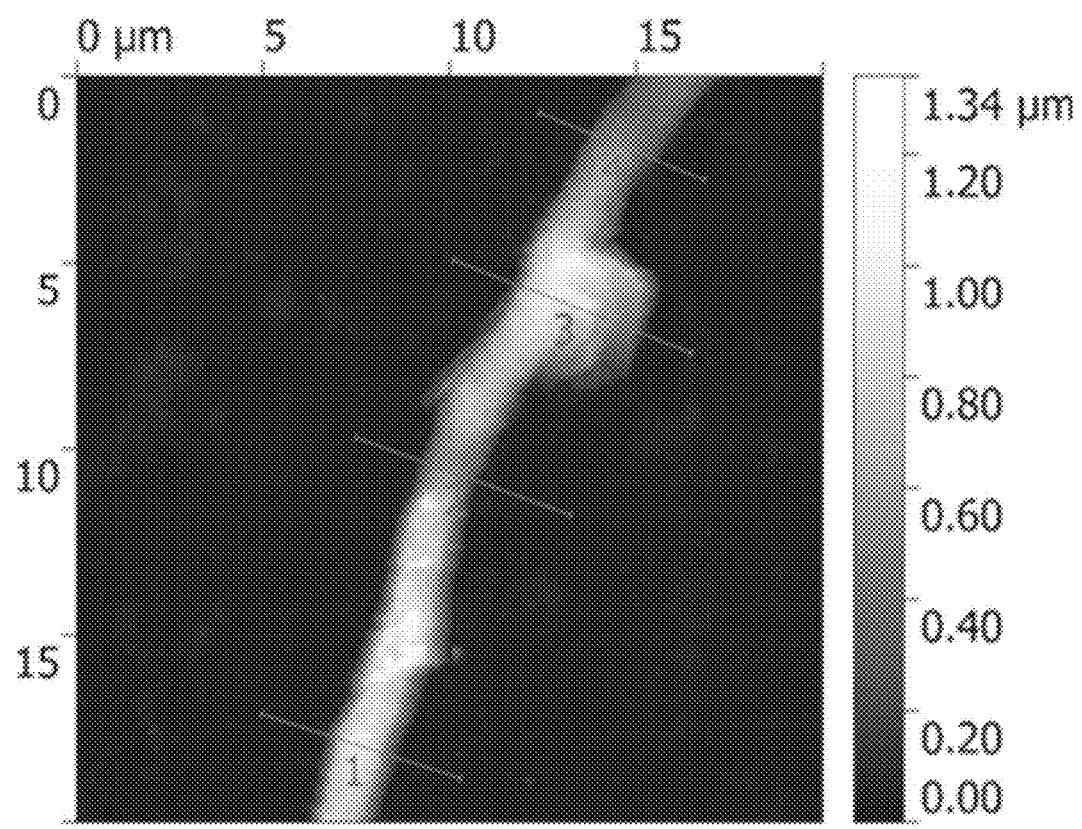
Figure 2D:
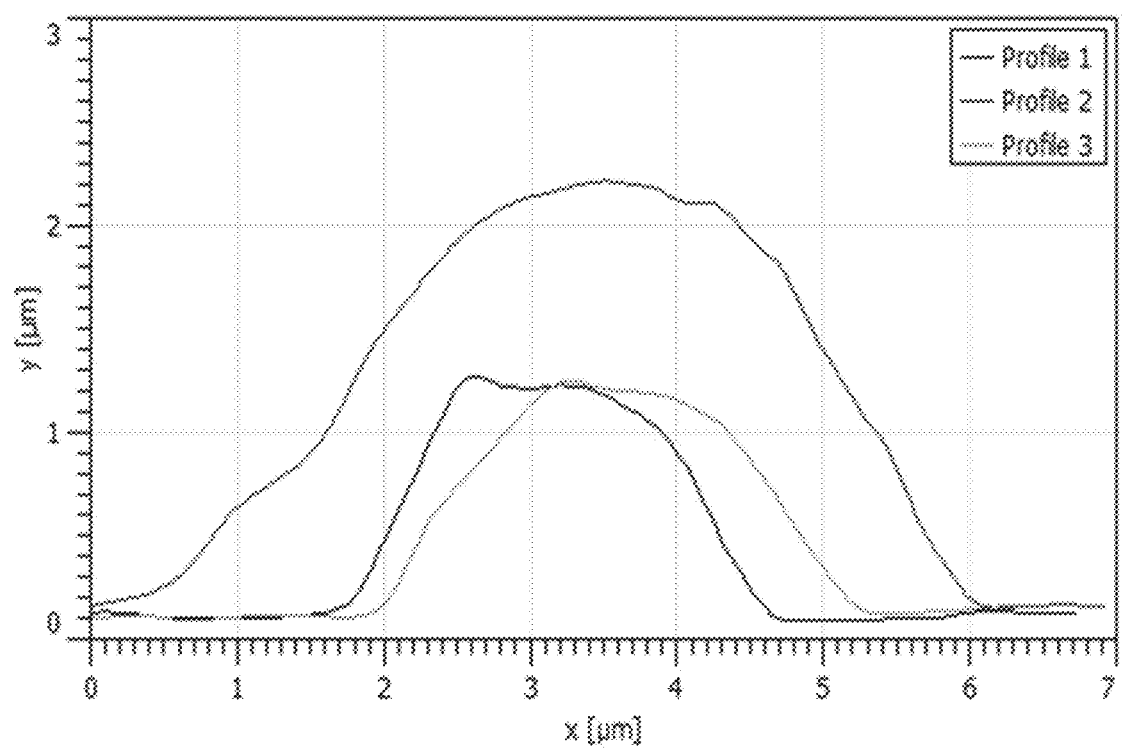
Figure 3:
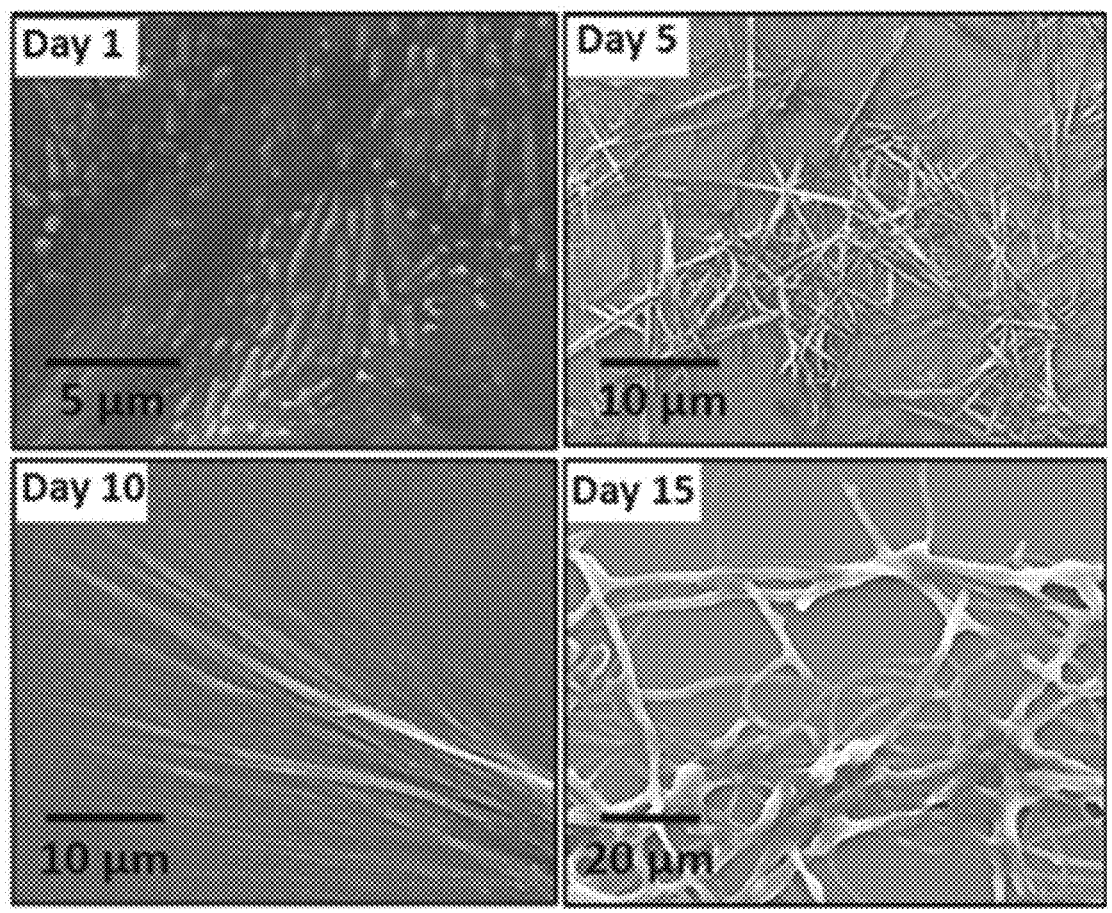
FIG. 3 presents HR-SEM images of Pro-Phe-Phe after 1, 5, 10 and 15 days in phosphate buffer (pH 7.4); the peptide transformed from unstructured to self-assembled twisted fiber morphology over the course of 15 days.
Figure 4A:
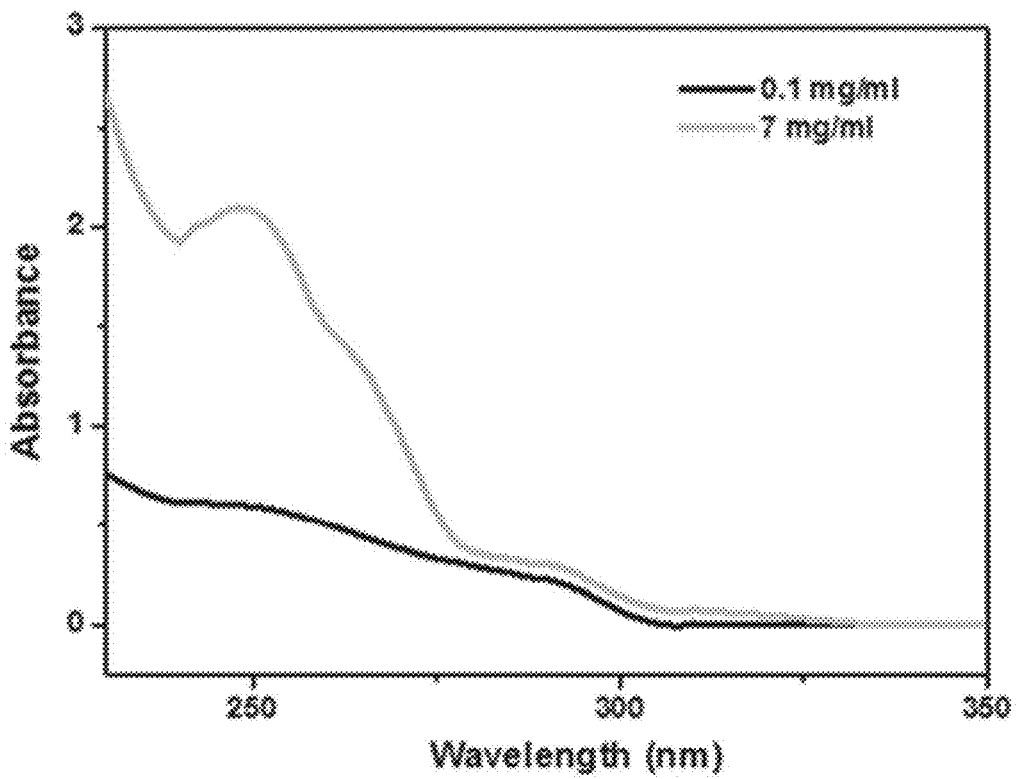
FIGS. 4A and 4B present UV-visible spectra of Pro-Phe-Phe at 0.1 and 7 mg/ml (FIG. 4A), and a graph showing the optical density of Pro-Phe-Phe as a function of the logarithm of Pro-Phe-Phe concentration (FIG. 4B), indicating a critical aggregation concentration of ~1.2 mg/ml.
Figure 4B:
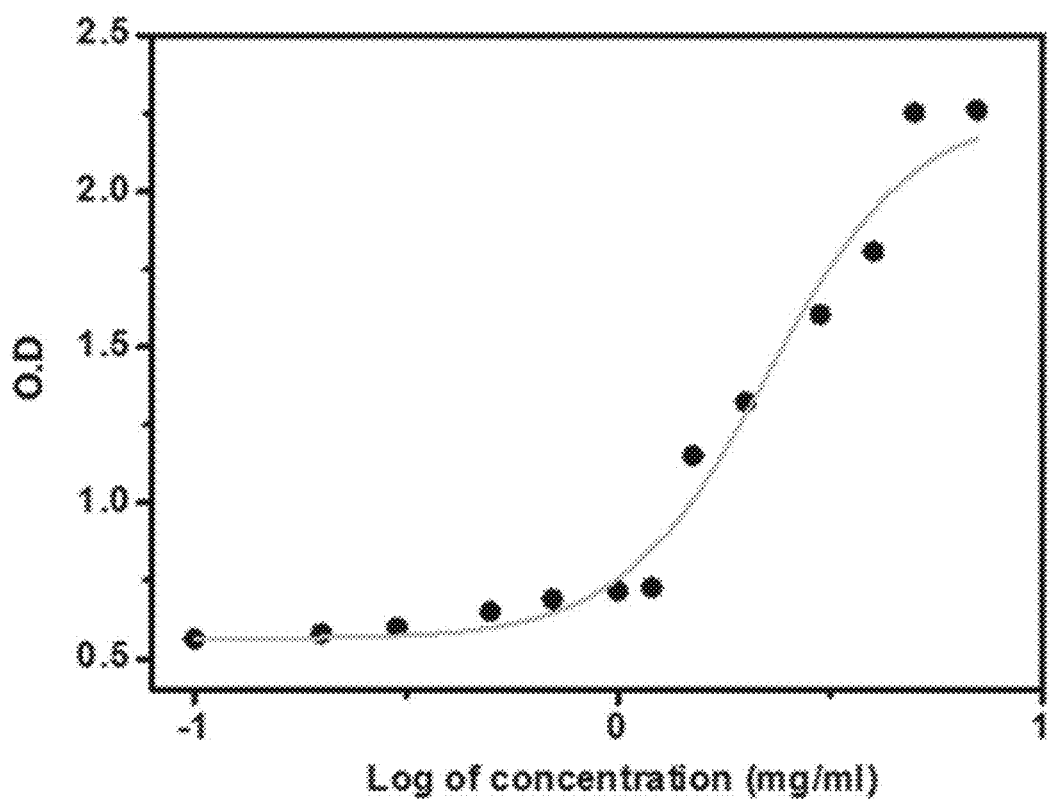
Figure 5A:
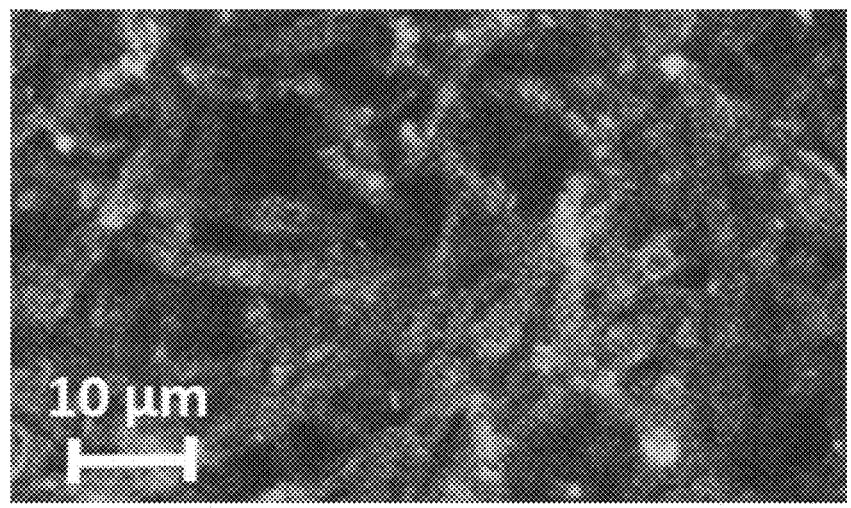
FIGS. 5A and 5B presents confocal fluorescence microscopy images of Pro-Phe-Phe fibers stained with Thioflavin T (ThT) in phosphate buffer at pH 7.4 (using 20 mM peptide and 20 µM ThT).
Figure 5B:
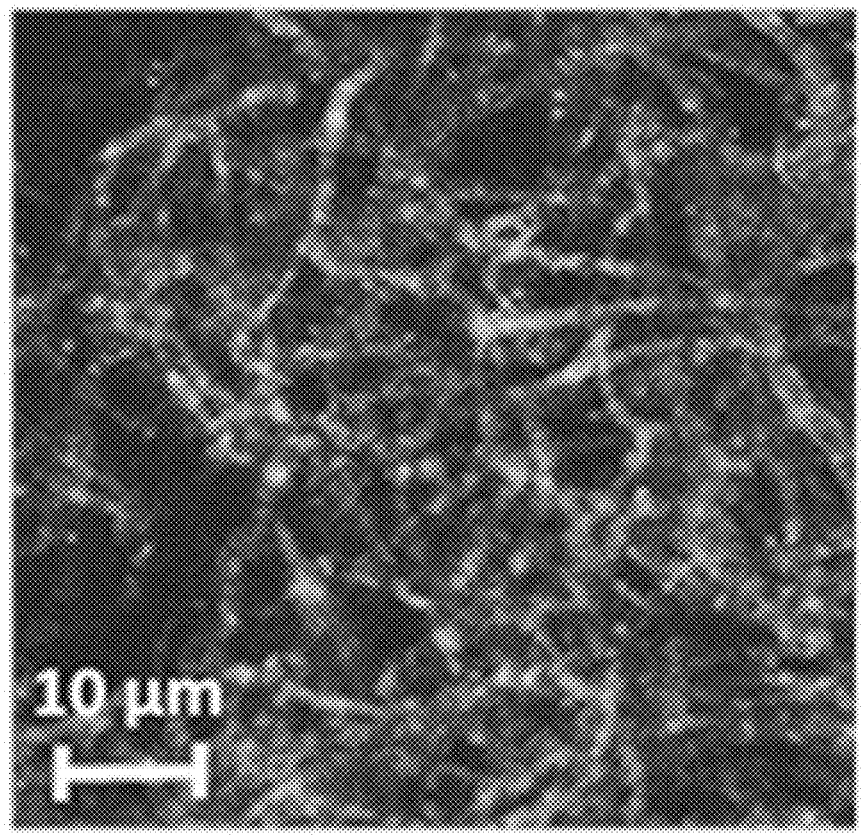
Figure 6:
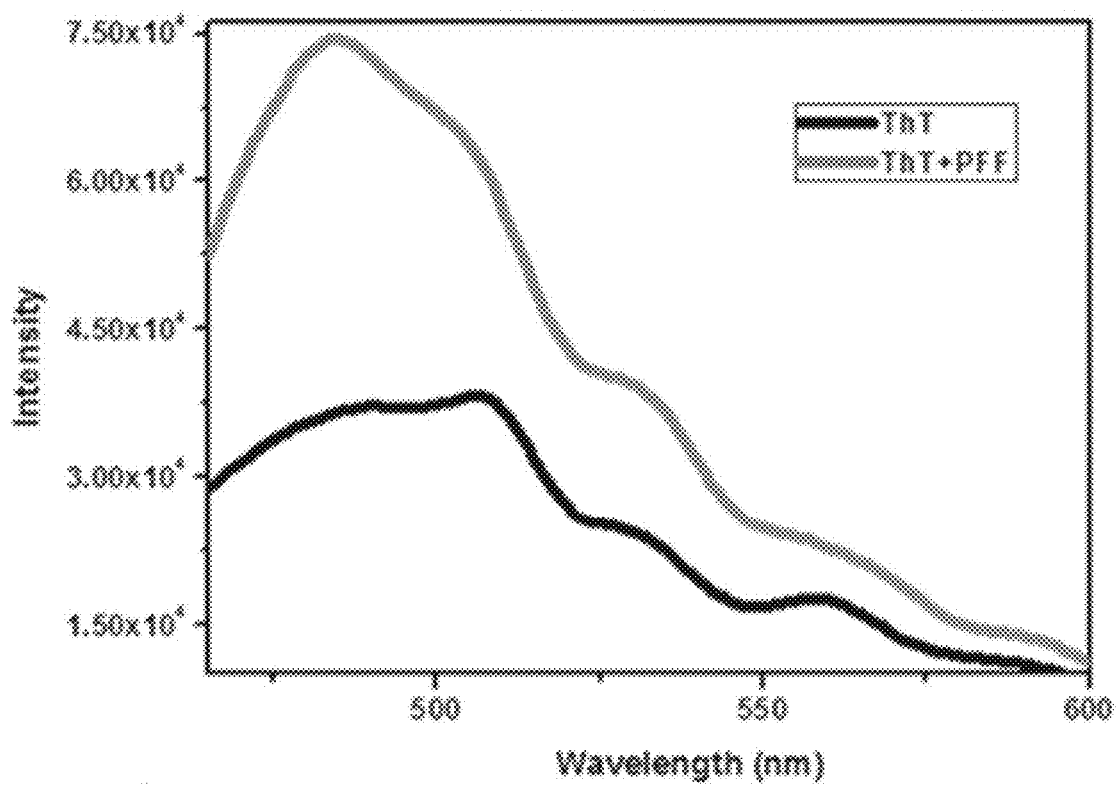
FIG. 6 presents a ThT fluorescence emission spectrum (excitation at 440 nm) upon addition of pre-assembled Pro-Phe-Phe (PFF) fibers at a concentration of 20 mM (red), or of phosphate buffer as a control (black), to 40 µM ThT solution in phosphate buffer at a 1:1 volume ratio.

The present invention, in some embodiments thereof, relates to materials science, and more particularly, but not exclusively, to self-assembled structures formed of short peptides, which exhibit piezoelectric properties, and to uses thereof.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exploring the possibilities of renewable, sustainable, green energy sources to replace fossil fuels is one of the most significant and challenging issues in energy research. Energy harvesters based on piezoelectric effects are a potential source for providing long-term energy needs and sustainable development.

The present inventors have uncovered various short peptides which self-assemble to form three-dimensional structures with notable mechanical and piezoelectric properties. Such piezoelectric peptide-based structures (e.g., nanostructures) are of particular potential as they exhibit impressive piezoelectric characteristics while being fully biocompatible, and may be used in diverse applications. The use of peptide-based structures as functional piezoelectric materials may overcome existing challenges for various applications, including, but not limited to, energy harvesting, sensing and monitoring, healthcare and medical applications, cell and tissue regeneration and wearables. The materials described herein may provide a renewable and biocompatible energy source based on controlled piezoelectricity of peptides, and open up new directions in the design of future smart devices.

For example, the present inventors have envisioned that peptide-based materials described herein can overcome the problems associated with conventional piezoelectric materials such as PZT, which tend to be toxic and therefore less suitable for medical applications and wearables that come in contact with the human body. The peptide-based materials described herein may therefore provide a solution to a great unmet need for biocompatible piezoelectric materials.

While reducing the present invention to practice, the present inventors have uncovered dipeptides and tripeptides comprising one or more aromatic amino acid which are capable of self-assembling into structures which exhibit a considerable piezoelectric effect. For example, the present inventors have demonstrated that proline-phenylalanine-phenylalanine (Pro-Phe-Phe) tripeptide is the shortest peptide sequence known to date to organize into a cross-helical structural arrangement stabilized by intermolecular hydrogen bonds and aromatic interactions, that peptide bond units are aligned in the same orientation in the helical structure, such that the helix gains an inherent dipole moment, and that these polarized cross-helical crystal structures possess a high shear piezoelectricity. The inventors have further designed and successfully practiced the novel tripeptide hydroxyproline-phenylalanine-phenylalanine (Hyp-Phe-Phe), which forms helical-like sheets via aromatic interactions of the Phe rings to comprise a cross-helical architecture, characterized by a Young's modulus of about 102 GPa, indicating a remarkable stiffness of the super-helical conformation, similar to that of the natural collagen matrix. The inventors have further designed and successfully practiced dipeptides such as Boc-Dip-Dip (tert-butoxycarbonyl-diphenylalanine-diphenylalanine) and (L)Trp-(D)Trp (L-tryptophan-D-tryptophan), which self-assemble and display a significant piezoelectric effect.

Embodiments of the present invention relate to piezoelectric three-dimensional structures made of a plurality of peptides, to a piezoelectric transducer comprising such a three-dimensional structure made of a plurality of peptides, to electronic devices comprising such a transducer, and to processes of preparing such a transducer.

Peptides and Peptide Structures:

According to an aspect of some embodiments of the invention, there is provided a three-dimensional structure made of a plurality of peptides, the peptides preferably being self-assembling and the structure being piezoelectric (e.g., featuring piezoelectricity as defined herein), provided that the plurality of peptides does not consist of a Phe-Phe dipeptide.

Herein, the term "three-dimensional structure" refers to a structure composed of more than one molecule in each of three perpendicular dimensions, e.g., as opposed to a monolayer, which is only one molecule wide in at least one dimension.

In some of any of the embodiments described herein, the three-dimensional structure is a nanostructure, that is, a structure that has an average size of less than 1 micrometer, or less than 500 nm, or less than 100 nm, of at least one dimension or cross-section thereof.

Herein, the term "piezoelectric" refers to any substance (e.g., a three-dimensional structure described herein) capable of accumulating an electric charge in response to mechanical stress, and the term "piezoelectricity" refers to the aforementioned phenomenon of accumulating an electric charge in response to mechanical stress. A piezoelectric substance is optionally characterized by at least one piezoelectric coefficient which is at least 10 pC/N (picocoulombs per newton), or at least 20 pC/N, or at least 30 pC/N, or at least 50 pC/N, or at least 75 pC/N, or at least 100 pC/N.

In some of any of the respective embodiments, the self-assembling peptides are capable of assembling into three-dimensional structures (as defined herein) upon contacting the peptides with an aqueous solution (e.g., aqueous phosphate buffer pH 7.4 and/or pure water), and/or in other solvents or forms, for example, at a gas-solid interface (e.g., as in physical vapor deposition (PVD)). In some embodiments, the three-dimensional structures form upon incubation (e.g., for at least one day or for at least one week) in a solvent (aqueous or non-aqueous) at a peptide concentration at which the peptides dissolve in the solvent. In exemplary embodiments, the solvent is an aqueous solvent and the incubation temperature is 18° C.

In some of any of the respective embodiments, the self-assembling peptides are capable of assembling into three-dimensional structures (as defined herein) upon contacting peptides (e.g., in dry form) with water (e.g., double-distilled water). In some such embodiments, the concentration of peptide is 5 mg/ml. In exemplary embodiments, the three-dimensional structures form upon incubation (e.g., for at least one day or for at least one week) in water at a peptide concentration of 5 mg/ml, at an incubation temperature of 18° C.

According to some of any of the embodiments described herein, the three-dimension structure comprising a plurality of self-assembling peptides is to be regarded as a self-assembled three-dimensional structure formed upon self-assembly of the plurality of peptides.

In some of any of the respective embodiments, the three-dimensional structure is characterized by a non-centrosymmetric unit cell. The non-centrosymmetric unit cell may be associated with a polar crystal class (e.g., 1, 2, m, mm2, 4, 4 mm, 3, 3 m, 6 and/or 6 m (according to Hermann-Mauguin notation)) or a non-polar crystal class (e.g., 222, $\bar{4}$, 422, $\bar{4}2$ m, 326$^-$, 622, $\bar{6}2$ m, 23 and/or $\bar{4}3$ m (according to Hermann-Mauguin notation)).

A conformation of molecules (e.g., along with a conformation of atoms in the molecules) of a given three-dimensional structure or plurality of such structures may be characterized experimentally according to well-known techniques in the crystallographic arts, such as by x-ray diffraction techniques. The structures are preferably separated from any surrounding liquid and/or unassembled peptide molecules (e.g., by centrifugation).

Optionally, powder x-ray diffraction techniques are used (e.g., according to procedures exemplified in the Examples section herein) to analyze a plurality of structures, for example, using GSAS-11 software to determine cell parameters, according to procedures such as described in Toby et al. [*J Appl Cryst* 46:544-549 (2013)] (which is incorporated herein by reference, especially the contents therein describing x-ray diffraction techniques), and/or using the whole profile fitting method with a final Rwp=1.1%, according to procedures such as described in Pawley [*J Appl Cryst* 14:357-361 (1981)] (which is incorporated herein by reference, especially the contents therein describing analysis of x-ray diffraction data).

Classification of the unit cell (e.g., as non-centrosymmetric), crystal class and/or space group (according to any of the respective embodiments described herein) of a given structure (e.g., characterized according to techniques described herein) is a mathematical technique which is well known in the chemical and physical arts, and may optionally be performed using commercially available algorithms.

In exemplary embodiments, the three-dimensional structure is characterized by P1 space group (associated with crystal class 1 according to Hermann-Mauguin notation), a $P2_1$ space group (associated with crystal class 2 according to Hermann-Mauguin notation) or a $P2_12_12_1$ space group (associated with crystal class 222 according to Hermann-Mauguin notation).

In some of any of the respective embodiments, the three-dimensional structure is a crystalline form, which may optionally be a single crystal form or polycrystalline form. The crystalline form may optionally be characterized by a triclinic, monoclinic and/or orthorhombic crystal structure.

In some of any of the respective embodiments, at least a portion, or each, of the plurality of peptides has a helical secondary structure in a three-dimensional structure described herein (according to any of the respective embodiments). In some such embodiments, at least a portion, or each, of the plurality of peptides has at least three amino acid residues (according to any of the respective embodiments described herein). In some such embodiments, at least a portion, or each, of the plurality of peptides is a tripeptide. Pro-Phe-Phe and Hyp-Phe-Phe are exemplary amino acid sequences for peptides having a helical secondary structure.

Tripeptides organized in helical assemblies have only very rarely been reported [Parthasarathy et al., *Proc Nat Acad Sci USA* 87:871-875 (1990)], particularly tripeptides constituted from coded amino acids. Moreover, the three residues in previously reported tripeptides with helical secondary structure are typically not sufficient to complete a helical turn, and at least one water molecule was required as an additional residue to link the translationally related peptide segments along the helical axis; whereas, as exemplified herein, Pro-Phe-Phe forms three-dimensional structures with a helical secondary structure without water molecules.

Herein, the term "secondary structure" refers to the conformation of an individual peptide molecule (e.g., within a crystalline form), as opposed, e.g., to the relative positions of different peptide molecules.

A helical secondary structure is optionally characterized by at least one amino acid residue having dihedral angles (as defined in the art, e.g., in Ramachandran plots) of psi ($\psi$) in a range of from −100° to 45° (optionally from −90° to 45°, and optionally from −60° to 30°), and phi ($\phi$) in a range of from −180° to 15° (optionally from −165° to 0°, and optionally from −150° to −15°). In some embodiments, at least 50%, optionally each, of the non-terminal residues of a peptide (having three or more amino acid residues) has dihedral angles within the aforementioned ranges. As exemplified herein, Pro-Phe-Phe and Hyp-Phe-Phe form structures characterized by psi ($\psi$) in a range of from about −35° to about −45°, and phi (φ) in a range of from about −70° to about −80° (in the non-terminal residue thereof).

Dihedral angles for a given structure may be readily determined based on a conformation of molecules in such a structure characterized according to any of the respective embodiments described hereinabove (e.g., using commercially available algorithms).

In some of any of the respective embodiments described herein, a crystalline form described herein (e.g., according to any of the respective embodiments) does not include solvent molecules (e.g., water molecules) other than the peptide molecules as a repeating component of the crystal structure. In some such embodiments described herein, the crystalline form is characterizes a helical secondary structure (e.g., according to any of the respective embodiments described herein). In some embodiments, the peptide with a helical secondary structure has at least three amino acids, and optionally is a tripeptide. As exemplified herein, Pro-Phe-Phe is a tripeptide which forms such solvent-free structures with helical secondary structure.

In some of any of the respective embodiments described herein, a crystalline form described herein (e.g., according to any of the respective embodiments) includes a component other than the peptide—for example, a counter-ion and/or solvent molecule (optionally water molecule)—as a repeating component thereof. The additional (non-peptide) component may be distributed throughout a crystalline form in any configuration, for example, wherein each solvent molecule is in contact only with one or more peptide molecule, or wherein solvent molecules are in contact with each other (optionally bonded by hydrogen bonds), e.g., so as to form a layer of solvent (e.g., water) molecules. (L)Trp-(D)Trp are (D)Trp-(L)Trp non-limiting examples of peptides which form piezoelectric structures comprising a layer of water molecules.

Herein, the term "Phe-Phe dipeptide" encompasses linear dipeptides consisting of two phenylalanine (Phe) residues (L-Phe and/or D-Phe; preferably unsubstituted), as well as dipeptides which further comprise (in addition to 2 Phe residues) one or more moiety (other than an amino acid residue) attached to the N-terminus (e.g., a carbonyl moiety attached to the N-terminus via an amide bond) or C-terminus (e.g., an amine moiety attached to the C-terminus via an amide bond) thereof.

In some of any of the respective embodiments, at least a portion, or each, of the plurality of peptides comprises peptides of 2 to 10 amino acid residues, optionally from 2 to 9 amino acid residues, optionally from 2 to 8 amino acid residues, optionally from 2 to 7 amino acid residues, optionally from 2 to 6 amino acid residues, optionally from 2 to 5 amino acid residues, and optionally from 2 to 4 amino acid residues. In exemplary embodiments, at least a portion, or each, of the plurality of peptides comprises 2 or 3 amino acid residues. In some of any of the aforementioned embodiments, each amino acid reside is an α-amino acid residue.

In some of any of the respective embodiments, at least a portion, or each, of the plurality of peptides comprises peptides of 3 to 10 amino acid residues, optionally from 3 to 9 amino acid residues, optionally from 3 to 8 amino acid residues, optionally from 3 to 7 amino acid residues, optionally from 3 to 6 amino acid residues, optionally from 3 to 5 amino acid residues, and optionally from 3 to 4 amino acid residues. In exemplary embodiments, at least a portion, or each, of the plurality of peptides comprises 3 amino acid residues. In some of any of the aforementioned embodiments, each amino acid reside is an α-amino acid residue.

In any of the respective embodiments herein, a "peptide" may optionally be a linear peptide and/or a cyclic peptide, unless otherwise indicated. Specific peptide formulas described herein (e.g., "Pro-Phe-Phe") refer to a linear peptide, unless preceded by the prefix "cyclo-".

A cyclic peptide according to any of the respective embodiments described herein may optionally be a cyclic peptide obtainable by linking a peptide C-terminus to a peptide N-terminus by an amide bond, by linking two side-chains (e.g., cysteine side chains) by a disulfide (—S—S—) bond, by a lactam bridge, by a hydrocarbon-staple (optionally a chiral hydrocarbon staple), by a triazole bridge, by bio-Cys alkylation, or by an acetone Hcy linker, and/or by any form of peptide cyclization described in the art, e.g., in Hu et al. [*Angew Chem Int Ed* 55:8013-8017 (2016)], the contents of which are incorporated herein by reference in their entirety, especially with respect to types of cyclic peptides.

In exemplary embodiments, a cyclic peptide as described herein is a peptide in which a peptide's C-terminus is linked to its N-terminus by an amide bond.

In any of the respective embodiments herein, a cyclic peptide is a dipeptide, e.g., a substituted diketopiperazine. Exemplary cyclic dipeptides include cyclo-Phe-Phe, cyclo-Gly-Trp and cyclo-Phe-Trp. The skilled person will appreciate that an indicated "first" amino acid of a cyclic peptide (e.g., a cyclic peptide obtainable by linking a peptide C-terminus to a peptide N-terminus by an amide bond, such as a substituted diketopiperazine) may be arbitrary, such that, e.g., cyclo-Phe-Trp may also be considered as cyclo-Trp-Phe.

In any of the respective embodiments herein in which the chirality of one or more amino acid residues of a peptide is not explicitly defined, each of the amino acid residues may independently be an L-amino acid residue or a D-amino acid residue. In some such embodiments, each of the amino acid residues in the peptide is an L-amino acid residue or each of the amino acid residues in the peptide is a D-amino acid residue.

In any of the respective embodiments herein pertaining to a peptide, each of the amino acid residues of the peptide may independently be a coded amino acid residue or a non-coded amino acid residue. In some embodiments, the peptide(s) comprises at least one non-coded amino acid residue, for example, hydroxyproline (Hyp) and/or β,β-diphenylalanine (Dip).

Herein, a "coded" amino acid refers to any of the 20 "standard" amino acids encoded by the universal genetic code.

In some of any of the respective embodiments, at least one of the amino acid residues (in at least a portion, or each, of the plurality of peptides) comprises an aromatic moiety. In some embodiments, at least two adjacent amino acid residues (in at least a portion, or each, of the plurality of peptides) each comprise an aromatic moiety. In some such embodiments, the at least two adjacent amino acid residues comprising an aromatic moiety (in at least a portion, or each, of the plurality of peptides) include a C-terminal amino acid residue and/or do not include an N-terminal amino acid residue, optionally wherein the peptide is a linear tripeptide and the adjacent amino acid residues comprising an aromatic moiety are amino acid residues #2 and #3 (numbering from the N-terminus). Examples of amino acid residues comprising an aromatic moiety include, without limitation, residues of the coded amino acids phenylalanine (Phe), tyrosine (Tyr), tryptophan (Trp), and histidine (His), and of the non-coded amino acids β,β-diphenylalanine (Dip), naphthylalanine (Nal), and dihydroxyphenylalanine (DOPA).

As used herein, the phrase "aromatic moiety" describes a monocyclic or polycyclic moiety having a completely conjugated pi-electron system. The aromatic moiety can be an all-carbon moiety (aryl) or can include one or more heteroatoms such as, for example, nitrogen, sulfur or oxygen (heteroaryl). The aromatic moiety can be substituted or unsubstituted, whereby when substituted, the substituent can be, for example, one or more of alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano and amine. The aromatic moiety can include one or more aryl and/or heteroaryl groups, as defined herein below, which can be fused or non-fused to one another.

The phrase "aromatic amino acid residue", as used herein, refers to an amino acid residue that comprises an aromatic moiety in its side-chain.

Exemplary aromatic moieties include, but are not limited to, phenyl, biphenyl, naphthalenyl, phenanthrenyl, anthracenyl, [1,10]phenanthrolinyl, indoles, imidazoles, thiophenes, thiazoles and [2,2']bipyridinyl, each being optionally substituted. Thus, representative examples of aromatic moieties that can serve as the side chain within the aromatic amino acid residues described herein include, without limitation, substituted or unsubstituted naphthalenyl, substituted or unsubstituted phenanthrenyl, substituted or unsubstituted anthracenyl, substituted or unsubstituted [1,10]phenanthrolinyl, substituted or unsubstituted [2,2']bipyridinyl, substituted or unsubstituted biphenyl, and substituted or unsubstituted phenyl. The aromatic moiety can alternatively be substituted or unsubstituted heteroaryl such as, for example, indole, thiophene, imidazole, oxazole, thiazole, pyrazole, pyridine, pyrimidine, quinoline, isoquinoline, quinazoline, quinoxaline, and purine.

When substituted, the aromatic moiety includes one or more substituents such as, but not limited to, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine. Exemplary substituted phenyls may be, for example, pentafluoro phenyl, iodophenyl, biphenyl and nitrophenyl.

In some of any of the respective embodiments, at least one of the amino acid residues (in at least a portion, or each, of the plurality of peptides) comprises a plurality of non-fused aromatic moieties (e.g., two non-fused aromatic moieties). In some embodiments, at least two adjacent amino acid residues (in at least a portion, or each, of the plurality of peptides) each comprise a plurality of non-fused aromatic moieties (e.g., two non-fused aromatic moieties). In some such embodiments, the at least two adjacent amino acid residues comprising an aromatic residue (in at least a portion, or each, of the plurality of peptides) include a C-terminal amino acid residue, optionally wherein the peptide is a linear dipeptide. β,β-Diphenylalanine (Dip) is a non-limiting example of an amino acid whose residue comprises a plurality (two) of non-fused aromatic moieties.

Herein, "non-fused aromatic moieties" refers to two or more aromatic moieties which do not share two or more atoms of an aromatic ring (that is, two or more atoms which belong to an aromatic ring of each of the two or more moieties).

Examples of suitable (linear and cyclic) peptides include, without limitation, (L)Pro-(L)Phe-(L)Phe, (D)Pro-(D)Phe-(D)Phe, (L)Hyp-(L)Phe-(L)Phe, (D)Hyp-(D)Phe-(D)Phe, Boc-(L)Dip-(L)Dip, Boc-(D)Dip-(D)Dip, (L)Trp-(D)Trp, (D)Trp-(L)Trp, Gly-Trp, cyclo-(L)Phe-(L)Phe, cyclo-(D) Phe-(D)Phe, cyclo-Gly-(L)Trp, cyclo-Gly-(D)Trp, cyclo-(L)Phe-(L)Trp, and cyclo-(D)Phe-(D)Trp. In some of any of the respective embodiments, the peptides are the exemplary linear peptides (L)Pro-(L)Phe-(L)Phe, (D)Pro-(D)Phe-(D)Phe, Boc-(L)Dip-(L)Dip, Boc-(D)Dip-(D)Dip, (L)Trp-(D)Trp, and/or (D)Trp-(L)Trp; and/or the exemplary cyclic peptides cyclo-Gly-(L)Trp, cyclo-Gly-(D)Trp, cyclo-(L)Phe-(L)Trp, and/or cyclo-(D)Phe-(D)Trp.

In some of any of the embodiments described herein relating to a "portion" of peptides or plurality of peptides, the "portion" includes at least 50 weight percents of the indicated peptides (e.g., based on the total weight of all peptide molecules in a plurality of peptides according to any of the respective embodiments described herein), wherein the weight of a peptide is based on the weight of the free acid/free base (non-ionic) form. In some such embodiments, the "portion" includes at least 75 weight percents of the indicated peptides. In some embodiments, the "portion" includes at least 90 weight percents of the indicated peptides. In some embodiments, the "portion" includes at least 95 weight percents of the indicated peptides. In some embodiments, the "portion" includes at least 98 weight percents of the indicated peptides. In some embodiments, the "portion" includes at least 99 weight percents of the indicated peptides. In some embodiments, the "portion" includes at least 99.5 weight percents of the indicated peptides. In some embodiments, the "portion" includes at least 99.8 weight percents of the indicated peptides. In some embodiments, the "portion" includes at least 99.9 weight percents of the indicated peptides.

Embodiments of the present invention further relate to novel peptides which are usable, for example, in forming a piezoelectric transducer.

According to an aspect of some embodiments of the invention, there is provided a peptide having the amino acid sequence Hyp-Phe-Phe, optionally (L)Hyp-(L)Phe-(L)Phe and/or (D)Hyp-(D)Phe-(D)Phe.

According to an aspect of some embodiments of the invention, there is provided a peptide having the amino acid sequence Boc-Dip-Dip (wherein Boc is an N-terminal tert-butoxycarbonyl group), optionally Boc-(L)Dip-(L)Dip and/or Boc-(D)Dip-(D)Dip.

According to an aspect of some embodiments of the invention, there is provided a peptide having the amino acid sequence (L)Trp-(D)Trp or (D)Trp-(L)Trp.

In some of any of the embodiments described herein pertaining to a peptide, the peptide is in a three-dimensional structure (as defined herein) made of a plurality of the peptides, for example, a crystalline form according to any of the respective embodiments described herein (e.g., a triclinic, monoclinic or orthorhombic crystalline form).

According to an aspect of some embodiments of the invention, there is provided a three-dimensional structure made of a plurality of self-assembling peptides, wherein at least a portion, or each, of said plurality of peptides comprises the peptide Hyp-Phe-Phe (optionally (L)Hyp-(L)Phe-(L)Phe and/or (D)Hyp-(D)Phe-(D)Phe), Boc-Dip-Dip (optionally Boc-(L)Dip-(L)Dip and/or Boc-(D)Dip-(D)Dip), (L)Trp-(D)Trp and/or (D)Trp-(L)Trp, according to any of the respective embodiments described herein. In some embodiments, the three-dimensional structure is a piezoelectric structure, that is, a structure in which an electric charge accumulates in response to mechanical stress; optionally a structure characterized by non-centrosymmetric unit cell (e.g., according to any of the respective embodiments described herein).

Transducer:

According to an aspect of some embodiments of the invention, there is provided a piezoelectric transducer comprising a three-dimensional structure made of a plurality of peptides according to any of the embodiments described herein relating to peptides, the structure being piezoelectric (e.g., featuring piezoelectricity as defined herein). The peptides are preferably self-assembling peptides.

Herein, a "transducer" refers to a device or component of a device, which is configured for transforming one form of energy to another form of energy.

A piezoelectric transducer according to any of the respective embodiments described herein may optionally be configured to transform a mechanical input (optionally a sound wave) to an electronic output (e.g., current and/or voltage).

Alternatively or additionally, the transducer according to any of the respective embodiments described herein may optionally be configured to transform an electronic input (e.g., current and/or voltage) to a mechanical output (optionally a sound wave).

Without being bound by any particular theory, it is believed that peptide structures such as described herein are particularly suitable for use as piezoelectric materials in wearable devices (e.g., which contact the human body) and/or biological and/or medical applications, in view of the absence of lead (a common component of commercial piezoelectric materials) or other toxic substance and/or their ability to be readily metabolized (e.g., if they should leak from an implant). In addition, it is believed that the use of piezoelectric materials as a power source in biological and/or medical applications (e.g., implants) is particularly advantageous, in view of the undesirable bulk and/or potential toxicity of alternative power sources such as batteries.

In addition to a piezoelectric material (e.g., a peptide structure described herein), a piezoelectric transducer may comprise additional components, such as an electrical contact for collecting generated electronic output and/or for providing an electric input to a piezoelectric material.

The skilled person will be capable of constructing a piezoelectric transducer from a given piezoelectric material (e.g., according to any of the respective embodiments described herein).

Figure 41:
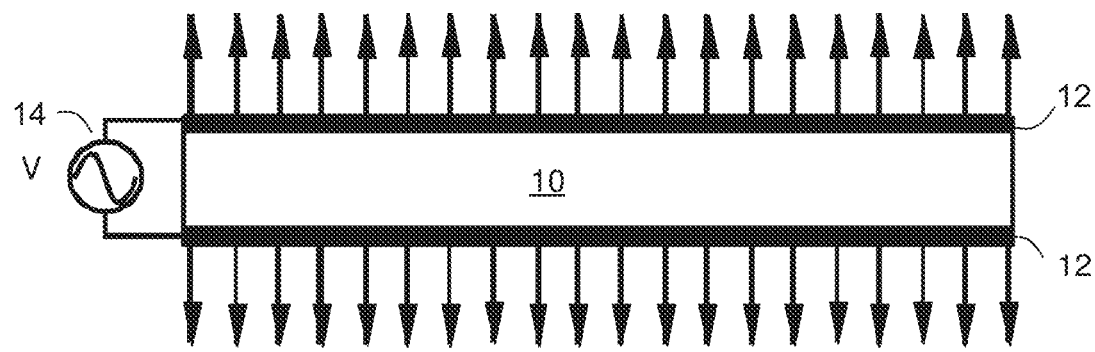
FIG. 41 presents a schematic depiction of a transducer utilizing a piezoelectric material according to some of the embodiments described herein.

Referring now to the drawings, FIG. 41 is a schematic illustration of a transducer comprising piezoelectric material 10 interposed between two surface electrodes 12.

Electrodes 12 are optionally electrically connected to a voltage source 14. When electrodes 12 are applied with voltage bias (e.g., due to voltage source 14), an electric field is generated within layer 10, and the thickness of layer 10 is changed via the inverse piezoelectric effect. The thickness change is illustrated in FIG. 41 by a series of up pointing and down pointing arrows. Voltage source 14 optionally serves as an electric input and the thickness change optionally serves as a mechanical output according to any of the respective embodiments described herein.

Alternatively or additionally, an electric charge may be induced in piezoelectric material by mechanical stress via the piezoelectric effect. In such a case, a mechanical stress induces a mechanical strain in piezoelectric material 10, illustrated in FIG. 41 by a series of up pointing and down pointing arrows, which induces a voltage bias between electrodes 12. Electrodes 12 may or may not be in electric communication (e.g., voltage source 14 is optionally absent). The voltage bias between electrodes 12 optionally serves as an electric output and the mechanical stress optionally serves as a mechanical input according to any of the respective embodiments described herein.

Electric charge in a piezoelectric material may be induced by an external electric field, or by a stress via the piezoelectric effect. Similarly the mechanical strain in a piezoelectric material may be induced by an electric field via the inverse piezoelectric effect, or by an external stress via Hooke's law. Thus, an electric field generated in a piezoelectric layer results in a longitudinal strain parallel to the field. When the layer is under compressive stress, the resulting longitudinal strain is the sum of the piezoelectric strain, and the opposing mechanical strain. Within the working range in which the piezoelectric effect is reversible, the relation between the longitudinal strain and the electric field is generally linear.

In some embodiments, a stack actuator is formed of a plurality of layers like layers of piezoelectric material 10 stacked along their thickness direction such that two adjacent layers in the stack are separated by a surface electrode like one of electrodes 12. In traditional stack actuators, all surface electrodes are electrically coupled, such that the same bias is applied to all electrodes and the same electric field is generated to all the active layers in the stack. The overall stroke of the actuator equals the sum of displacements of all the layers. In a traditional stack actuator with several hundreds of layers, the displacement of one layer is of the order of 0.1% of the thickness of the layer. Typical layer thickness may vary from 0.1 millimeter to 0.25 millimeter. The overall stroke of a traditional stack actuator is therefore no more that 0.1% of its length.

According to an aspect of some embodiments of the invention, there is provided an electronic device (i.e., a device which uses and/or generates electricity) comprising a transducer according to any of the respective embodiments described herein. In some such embodiments, the transducer functions as an energy source for the device (e.g., enabling mechanical energy to power an electronic device).

In some of any of the respective embodiments, the electronic device is a medical implant. The medical implant may have an electric power source and/or may generate an electric signal as an output, for example, to stimulate nerve and/or muscle tissue (e.g., as in a pacemaker and/or ear implant).

Herein, a transducer is considered to be an energy source when it transforms the mechanical energy of ordinary motion and/or pressure into a readily usable form of energy (e.g., electric power), such that there is no need for an additional energy source to provide the mechanical energy transformed to electronic energy.

In some of any of the respective embodiments, a transducer (according to any of the respective embodiments described herein) in the electronic device is configured to function as an energy source (e.g., according to any of the respective embodiments described herein), a sensor, a monitor, and/or a cell and/or tissue regenerator. For example, a sensor and/or monitor may comprise a transducer which translates data (e.g., mechanical data) into an electronic signal comprising the data, which may optionally be processed, displayed and/or saved on a storage medium, according to any suitable technique known in the art. In addition, a cell and/or tissue regenerator may optionally generate an electronic signal of a type (e.g., voltage and/or frequency) which enhances cell and/or tissue regeneration.

Examples of devices which may comprise a piezoelectric transducer according to any of the respective embodiments described herein include, without limitation, a generator (e.g., configured to produce electric power from mechanical energy); a pacemaker (optionally a self-powered pacemaker); a vital-signs monitor (optionally a heart monitor), e.g., in which mechanical signal (e.g., a pulse) is converted by the transducer to an electronic signal; an ultrasound wand (e.g., in which the transducer generates ultrasound waves from an electronic input, and/or senses ultrasound waves by converting them to an electronic signal); artificial skin (e.g., in which the transducer is configured to function as a power source, and/or for providing a sense of touch by generating an electronic signal in response to slight pressure); a temperature sensor (optionally a palm temperature sensor), e.g., in which the transducer is configured to function as a power source; and an ear implant (e.g., in which the transducer senses sound waves by converting them to an electronic signal which stimulates a nerve).

It is expected that during the life of a patent maturing from this application many relevant uses of piezoelectric materials will be developed and the scope of the terms "transducer" and "device" is intended to include all such new technologies a priori.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein, the term "alkyl" refers to a saturated aliphatic hydrocarbon including straight chain and branched chain groups. Preferably, the alkyl group has 1 to 20 carbon atoms. The alkyl group may be substituted or unsubstituted. When substituted, the substituent group can be, for example, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine. Representative examples are piperidine, piperazine, tetrahydrofuran, tetrahydropyran, morpholino and the like.

A "hydroxy" group refers to an —OH group.

A "thio", "thiol" or "thiohydroxy" group refers to and —SH group.

An "azide" group refers to a —N=N≡ group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to and —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "halo" or "halide" group refers to fluorine, chlorine, bromine or iodine.

A "trihaloalkyl" group refers to an alkyl substituted by three halo groups, as defined herein. A representative example is trihalomethyl.

An "amino" group refers to an —NR'R" group where R' and R" are hydrogen, alkyl, cycloalkyl or aryl.

A "nitro" group refers to an —NO$_2$ group.

A "cyano" group refers to a —C≡N group.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:

Fluorenylmethyloxycarbonyl (Fmoc) protected amino acids (Fmoc-phenylalanine-OH, Fmoc-proline-OH and Fmoc-hydroxyproline-OH) were obtained from GL Biochem (Shanghai) Ltd. 2-(1H-benzotriazole-1-yl)-1,1,3,3-tetramethyluronium hexafluorophosphate (HBTU), 1-hydroxybenzotriazole anhydrous (HOBt anhydrous), diisopropyl ethylamine (DIEA) and Wang resin solvents were obtained from Sigma.

Preparation of Peptides:

Uncapped peptides such as Pro-Phe-Phe, Hyp-Phe-Phe and (L)Trp-(D)Trp were synthesized using a standard Fmoc solid-phase synthesis strategy. After the deprotection of the resin with a 20% piperidine and 0.1 M HOBt in DMF solution, Fmoc-phenylalanine-OH was introduced and coupled with resin, followed by Fmoc deprotection and coupling with another Fmoc-phenylalanine-OH. The cycle of Fmoc deprotection and coupling was repeated based on the designed peptide sequences. All coupling reactions were affected by treatment with HBTU/HOBt/DIEA. Finally, cleavage was performed with a mixture of trifluoroacetic acid, triisopropylsilane and H$_2$O in a ratio of 95:2.5:2.5. The cleavage mixture was filtered into a round-bottomed flask and rotary evaporated to a concentrated solution that was subsequently dropped into cold ethyl ether for precipitation. The ether solution was centrifuged for 20 min at 4° C. and 10000 rpm, followed by the collection of solid product. The cold ethyl ether precipitation was repeated three times to remove TFA potential by-products [Tao et al., *Langmuir* 27:2723-2730 (2011)]. The final collected product was dissolved/dispersed in water and lyophilized for 2 days and then subjected to reverse-phase HPLC, mass spectrometry and NMR for purity analyses.

Preparation of Peptide Assemblies:

The synthesized peptides were purified to more than 95%, followed by mass spectrometry confirmation of their identity. All peptides were stored at −20° C. For assembly, peptides in the required concentration were dissolved in phosphate buffer at pH 7.4 by vigorous vortexing for 2 minutes. The peptide solutions were then incubated at 18° C. for two weeks with frequent shaking before examination.

Scanning Electron Microscopy (SEM):

Peptide assemblies were prepared as described hereinabove, and then a 5 μl sample was allowed to dry on a microscope glass cover slip at ambient conditions overnight and coated with Au. SEM images were recorded using a JSM-6700F FE-SEM apparatus (JEOL, Japan) operating at 10 kV.

Atomic Force Microscopy (AFM):

Peptide assemblies were prepared as described hereinabove, and then a 5 μl sample was deposited onto freshly cleaved V1 grade mica (Ted Pella, USA). The samples were allowed to dry under ambient conditions overnight. Images were obtained with AIST-NT Smart AFM system in non-contact (tapping) mode using 100 mm long silicon nitride cantilevers (OMCL-RC800PSA-W, Olympus, Japan) with resonance frequency of 70 kHz. The images were analyzed and visualized using the WSxM imaging software (Nanotec Electronica S.L, Spain) as described by Horcas & Fernandez. [*Rev Sci Instrum* 78:013705 (2007)].

Circular Dichroism (CD) Spectroscopy:

Peptides were dissolved in phosphate buffer at pH 7.4 to a final concentration of 5 mg/ml. The samples were incubated at 18° C. for two weeks with frequent shaking, and the experiments were performed without further dilution. CD spectra were collected using a Chirascan spectrometer (Applied Photophysics, UK) fitted with a Peltier temperature controller set to 25° C., using quartz cuvettes with an optical path length of 0.1 mm (Hellma Analytics, Germany). Absorbance of the sample was kept within the linear range of the instrument during measurement. Data acquisition was performed in steps of 1 nm at a wavelength range of 190 to 240 nm with a spectral bandwidth of 1.0 nm and an averaging time of 3 seconds. The spectrum of each sample was collected three times and averaged. Baseline was similarly recorded for phosphate buffer and subtracted from the samples spectra. Data processing was performed using Pro-Data Viewer software (Applied Photophysics, UK).

ThT Binding Assay:

For ThT binding analysis, 5 μl of peptide solution was drop casted over a microscope glass slide. 5 μl of 40 μM ThT was then immediately added and the sample was covered with a coverslip. The stained samples were visualized using an inverted LSM 510 META confocal laser scanning microscope (Carl Zeiss Jena, Germany) at excitation and emission wavelengths of 458 nm and 486-593 nm, respectively. The fluorescence images were edited using the Carl Zeiss AIM software. The ThT bound peptide fibers were represented using FITC fluorescence filter cube in green color. Peptide fibers without ThT under similar experimental conditions did not show any significant fluorescence. Peptide fibers after completion of ThT fluorescence kinetics also showed similar bright field emission.

Thioflavin T (ThT) Fluorescence Kinetic Assay:

Peptide assemblies were prepared as described hereinabove, and then an aged peptide sample was added to 40 μM ThT in water to a final concentration of 20 μM ThT. Data was measured in a Greiner bio-one black 96 well flat-bottom plate, immediately covered with a silicone sealing film (ThermalSeal RTS). The plate was incubated in a plate reader (CLARIOstar, BAAG LABTECH) at 37° C., with 100 rpm 5 second shaking before each cycle and data was collected for 250 cycles of 5 minute interval between each cycle. Upon excitation at 438 nm, ThT fluorescence emission spectra at 485 nm were recorded over time. Measurements were performed in triplicates. All triplicate values were averaged and plotted against time, and the standard error of means was represented as error bars. Phosphate buffer without any peptide was used as a control.

Fourier-Transform Infrared (FTIR) Spectroscopy:

Peptides were dissolved in phosphate buffer at pH 7.4 to a final concentration of 5 mg/ml. The samples were incubated at 18° C. for two weeks with frequent shaking. A 30 μl aliquot of the peptide solution was deposited onto disposable KBr infrared sample cards (Sigma-Aldrich, Israel), which were then allowed to dry under vacuum. The samples were saturated twice with 30 μl of $D_2O$ and vacuum dried. FTIR spectra were collected using a nitrogen purged Nicolet Nexus 470 FTIR spectrometer (Nicolet, Germany) equipped with a deuterated triglycine sulfate (DTGS) detector. Measurements were performed using a 4 $cm^{-1}$ resolution and by averaging 64 scans. The absorbance maxima values were determined using an OMNIC analysis program (Nicolet). The background was subtracted using a control spectrum.

Powder X-Ray Diffraction (XRD):

Lyophilized powder of peptide was dissolved in double distilled water and allowed to self-assemble by incubating at 18° C. for four weeks. The sample was then centrifuged for 10 minutes at 6000 rpm and the solution was decanted to remove non-assembled peptide molecules. The assembled fibers were lyophilized and poured inside a glass capillary 0.5 mm in diameter. X-ray diffraction was collected using a Bruker D8 Discover theta/theta diffractometer with liquid-nitrogen-cooled intrinsic Ge solid state linear position detector. The cell parameters were determined using the GSAS-II software, according to procedures such as described in Toby et al. [*J Appl Cryst* 46:544-549 (2013)]. Due to lower peak intensities, the Rietveld refinement of the Pro-Phe-Phe powder diffraction patterns did not result in an adequate fit. The diffraction patterns were therefore analyzed using the whole profile fitting method with a final Rwp=1.1%, according to procedures such as described in Pawley [*J Appl Cryst* 14:357-361 (1981)]. The peaks for Pro-Phe-Phe were indexed by monoclinic unit cell with a=5.330(2) Å, b=11.946(4) Å, c=34.36(1) Å and β=92.17(3°).

Crystal Preparation and Data Collection:

Crystals used for data collection were grown using the vapor diffusion method. Dry peptide was first dissolved in water, at a concentration of 5 mg/ml. Then, 50 μl of peptide solution was deposited into a series of 8×40 mm vessels. Each tube was sealed with Parafilm® film, in which a single small hole was pricked using a needle. The samples were placed inside a larger vessel filled with 2 ml of acetonitrile. The systems were ultimately capped and incubated at 18° C. for several days. Needle-like crystals grew within 7-8 days. For data collection, crystals were coated in paratone oil (Hampton Research), mounted on a MiTeGen cryo-loop and flash frozen in liquid nitrogen. Diffraction data were collected at 100 K on a Rigaku XtaLabPro apparatus with a Dectris 200K detector using CuKα radiation (λ=1.54184 Å).

Processing and Structural Refinement of Crystal Data:

Obtained diffraction data were processed using CrysAlisPro 1.171.39.22a software. The structure was solved by direct methods in SHELXT-2014/5, according to procedures such as described in Sheldrick [SHELXL-2013 University of Göttingen, Göttingen, Germany (2013)]. The refinements were performed with SHELXL-2016/4 and weighted full-matrix least-squares against $|F^2|$ using all data. Atoms were refined independently and anisotropically, with the exception of hydrogen atoms, which were placed in calculated positions and refined in a riding mode. The crystallographic data have been deposited in the CCDC with no. 1565666, 1823367, 1862583 and 1834550 for Pro-Phe-Phe, Hyp-Phe-Phe, Ala-Phe-Phe and Ala-Phe-Ala respectively.

Young's Modulus:

AFM experiments were carried out using a Nanowizard™ H AFM apparatus (JPK, Germany). The force curves were obtained using the commercial software from JPK and analyzed by a custom written procedure based on Igor pro 6.12 (Wavemetrics Inc.). Silica cantilevers (SSS-SeIHR-50, Nanosensor Company, with the half-open angle of the pyramidal face of θ<10°, tip radius: 2-10 nm, frequency in air: 96~175 kHz) were used in all experiments. The spring constant of the cantilevers was in the range of 7~35 N/meter. The maximum loading force was set to 368 nN for the Pro-Phe-Phe and Hyp-Phe-Phe crystals. All AFM nano-indentation experiments were carried out at room temperature. In a typical experiment, the peptide crystals were spread over the surface of a freshly cleaved mica substrate. Then, the cantilever was moved over a crystal with the help of an optical microscope at a constant speed of 15 μm/second and held on the crystal surface at a constant force of 368 nN. The cantilever was then retracted and moved to another spot for the next cycle. The indentation fit was performed using a custom-written Igor program and manually checked after the fitting was complete. Each approaching force-deformation curve in the range of 20 nm was fitted, or from the contact point to the maximum indentation depth, if the maximum indentation depth was less than 20 nm. By fitting the approaching curve to the Hertz model (Equation (1) below), the Young's modulus of the crystals was obtained. Typically, 4-5 such regions (3 μm×3 μm, 600 pixels) were randomly selected for each sample to construct the elasticity histogram.

$$F(h) = \frac{2}{\pi} \tan\alpha \frac{E}{1-v^2} h^2 \qquad (1)$$

where F is the force acting on the cantilever, h is the indentation depth of the crystal by the cantilever tip, α is the half angle of the tip, E is the Young's modulus of the sample and v is the Poisson ratio. v=0.3 was used in the calculation.

Computational Prediction of Piezoelectric Properties:

Calculations were performed using VASP with a 3×4×2 k-point sampling grid [Kresse et al., *Comput Mater Sci* 1996, 6:15-50 (1996)], Gaussian smearing with width 0.2 eV, and energy cut-off of 600 eV throughout all calculations. Geometry optimization was first performed with only ionic degrees of freedom allowed to relax, followed by a full relaxation of ions and lattice.

Static dielectric tensor as well as piezoelectric stress constants were calculated using finer k point grids of 4×6×5 and smearing width of 0.05 eV keeping an energy cut-off of 600 eV. The finite difference method was applied to calculate the electronic and ionic contributions to the piezoelectric tensor.

Example 1

Exemplary Helical Tripeptides

The self-assembly of Pro-Phe-Phe was explored using high resolution scanning electron microscopy (HRSEM) and atomic force microscopy (AFM).

As shown in FIGS. 1A-4B, the peptide adopted an elongated and unbranched helical fiber network morphology, with high aspect ratio in phosphate buffer at pH 7.4 above critical aggregation concentration.

The amyloidogenic nature of the fibers was examined using a Thioflavin-T (ThT) binding assay, an amyloid-specific fluorescent dye.

As shown in FIGS. 5A-8, staining the fibers with ThT resulted in high fluorescence levels, as well as a typical amyloid-binding emission signal, thus establishing their amyloidogenic nature.

Figure 7:
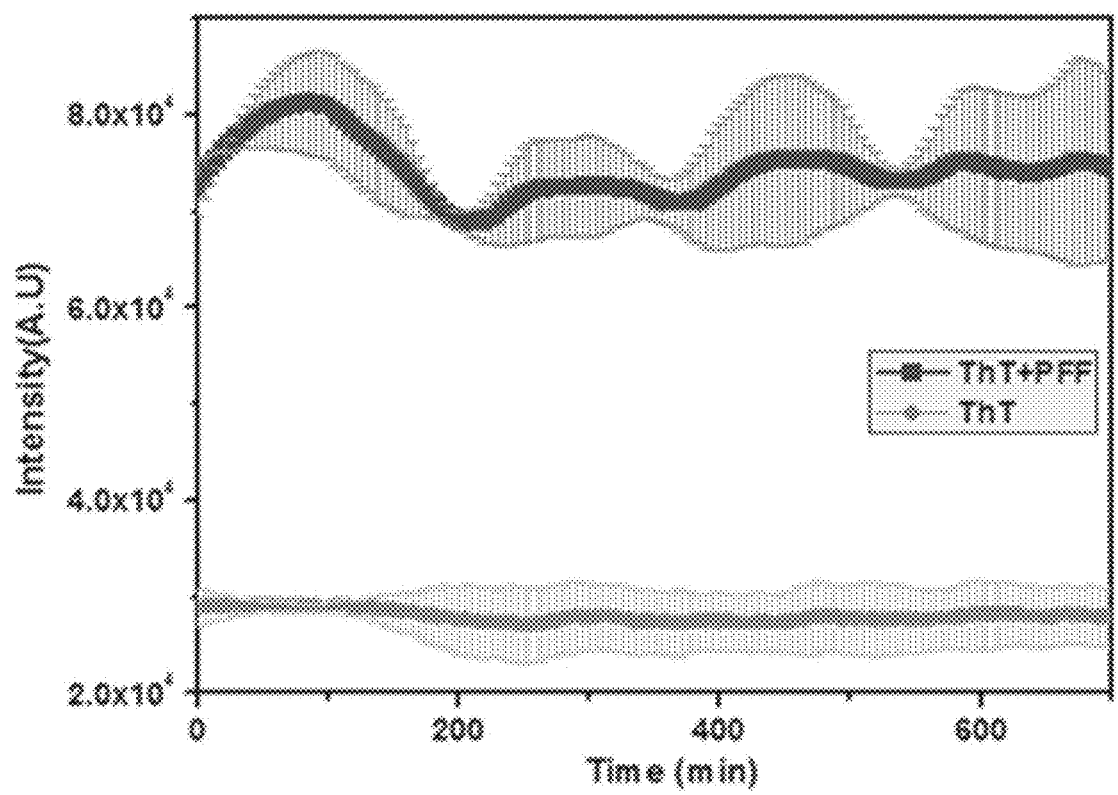
FIG. 7 presents a graph showing ThT fluorescence emission intensity at 485 nm as a function of time, upon incubation of 20 µM ThT with and without 20 mM Pro-Phe-Phe (PFF) (standard errors are indicated by error bars).
Figure 8:
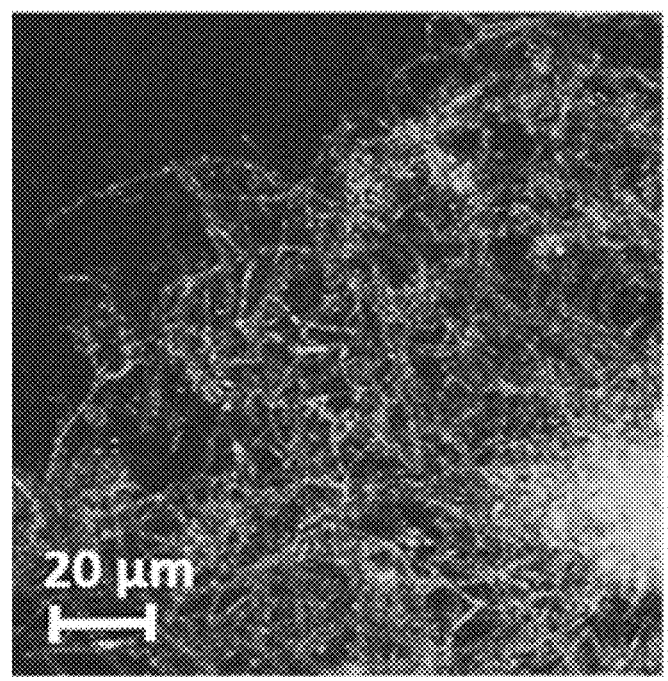
FIG. 8 presents a confocal fluorescence microscopy image of Pro-Phe-Phe fibers following a 12-hour incubation with ThT (using 20 mM peptide and 20 µM ThT).

As further shown in FIG. 7, mature fibers exhibited high fluorescence emission spectrum of final plateau regime upon ThT binding, resembling a characteristic kinetic profile of amyloid assemblies.

Circular dichroism (CD) spectroscopy was used to study the secondary structure of the peptide in solution.

Figure 9:
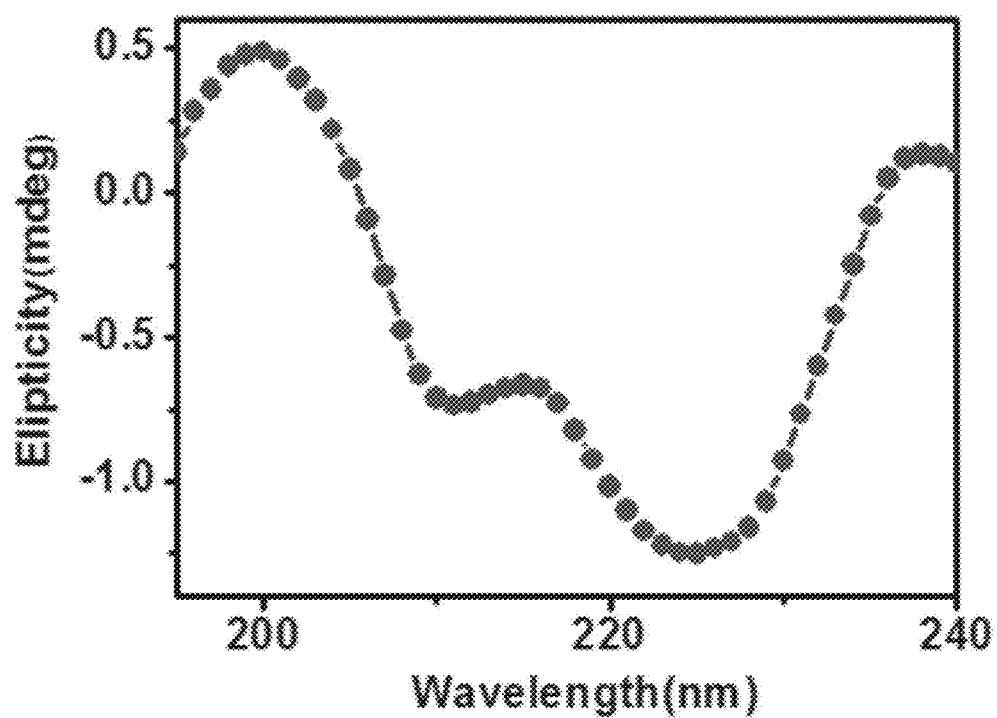
FIG. 9 presents a circular dichroism spectrum of Pro-Phe-Phe tripeptide in solution.
Figure 10:
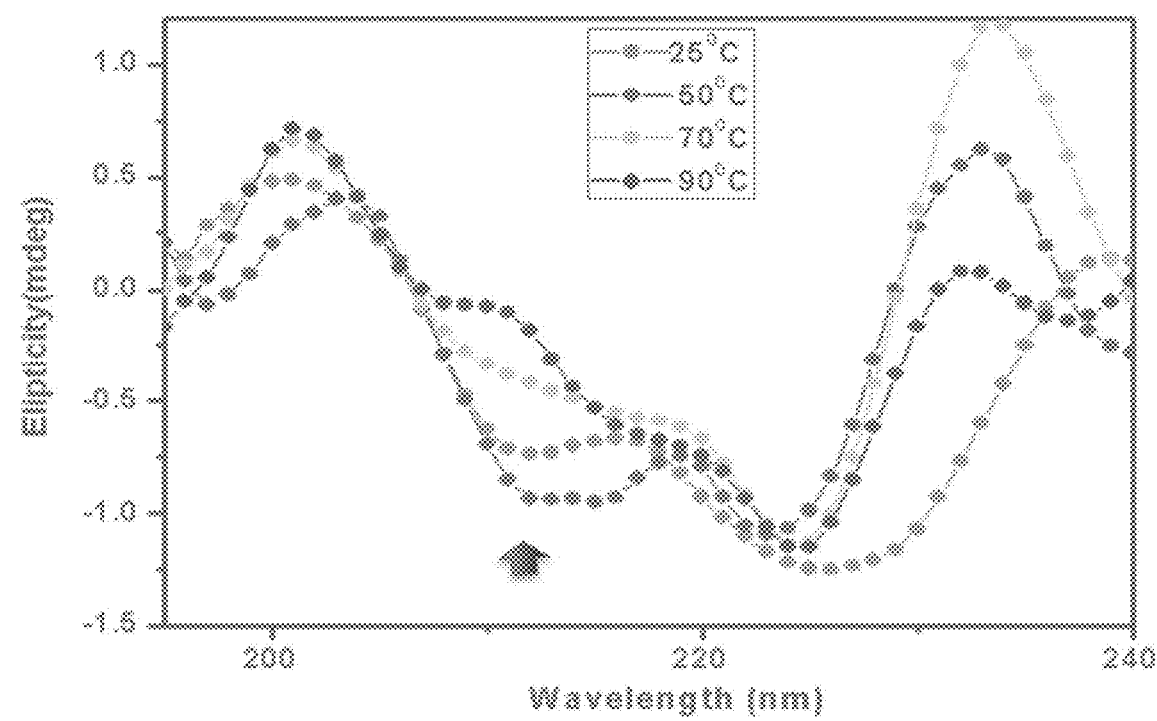
FIG. 10 presents circular dichroism spectra of Pro-Phe-Phe structures, at a concentration of 5 mg/ml in phosphate buffer, at temperatures of 25° C., 50° C., 75° C. and 90° C.

As shown in FIGS. 9 and 10, the tripeptide assemblies of Pro-Phe-Phe exhibited a double-negative-maxima CD signal, at 210 nm and 224 nm, with a positive maximum at around 198 nm.

The abovementioned signal is characteristic of short peptide helical conformation. [Chin et al., Proc. Natl Acad. Sci. USA 99:15416-15421 (2002)], and surprisingly dissimilar to the signal of self-assembling nanostructures formed by Phe-Phe and other building blocks from this structural family.

As further shown in FIG. 10, the helical conformation was stable at a wide range of temperatures (25-90° C.), with partial unfolding observed at elevated temperatures, as indicated by the temperature-dependent decrease in molar ellipticity at 210 nm.

Figure 11:
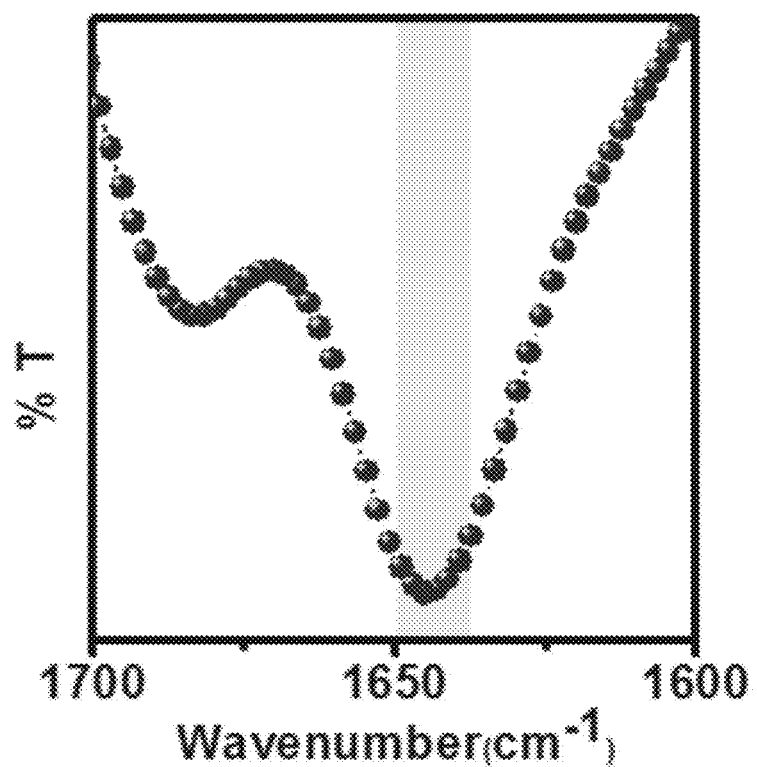
FIG. 11 presents a Fourier transform infrared (FTIR) transmission spectrum of Pro-Phe-Phe tripeptide.

As shown in FIG. 11, the Fourier transform infrared (FTIR) spectrum of Pro-Phe-Phe exhibited a sharp amide I band at 1647 cm$^{-1}$ with a shoulder at 1682 cm$^{-1}$.

These FTIR results indicate the presence of a predominant helical conformation [Haris & Chapman, *Biopolymers* 37:251-263 (1995); Cabiaux et al., *J Biol Chem* 264:4928-4938 (1989)].

To gain further information about the molecular spacing of the Pro-Phe-Phe assemblies, X-ray diffraction of the dried fibers was performed.

Figure 12:
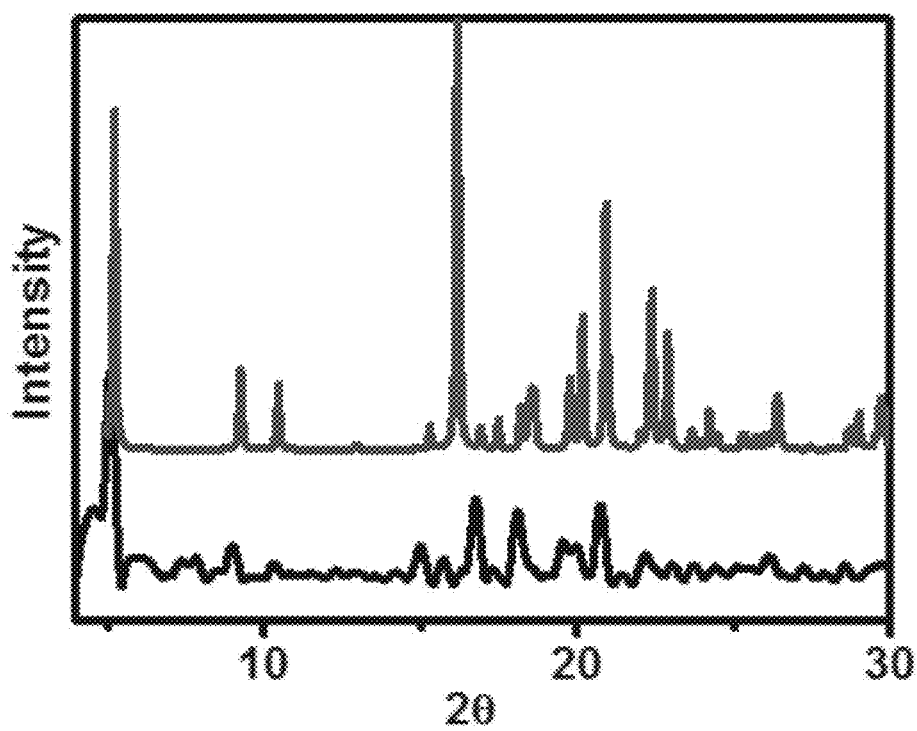
FIG. 12 presents an X-ray diffraction pattern of a Pro-Phe-Phe fiber (lower pattern) and simulated powder pattern obtained for a Pro-Phe-Phe single crystal (upper pattern).
Figure 13:
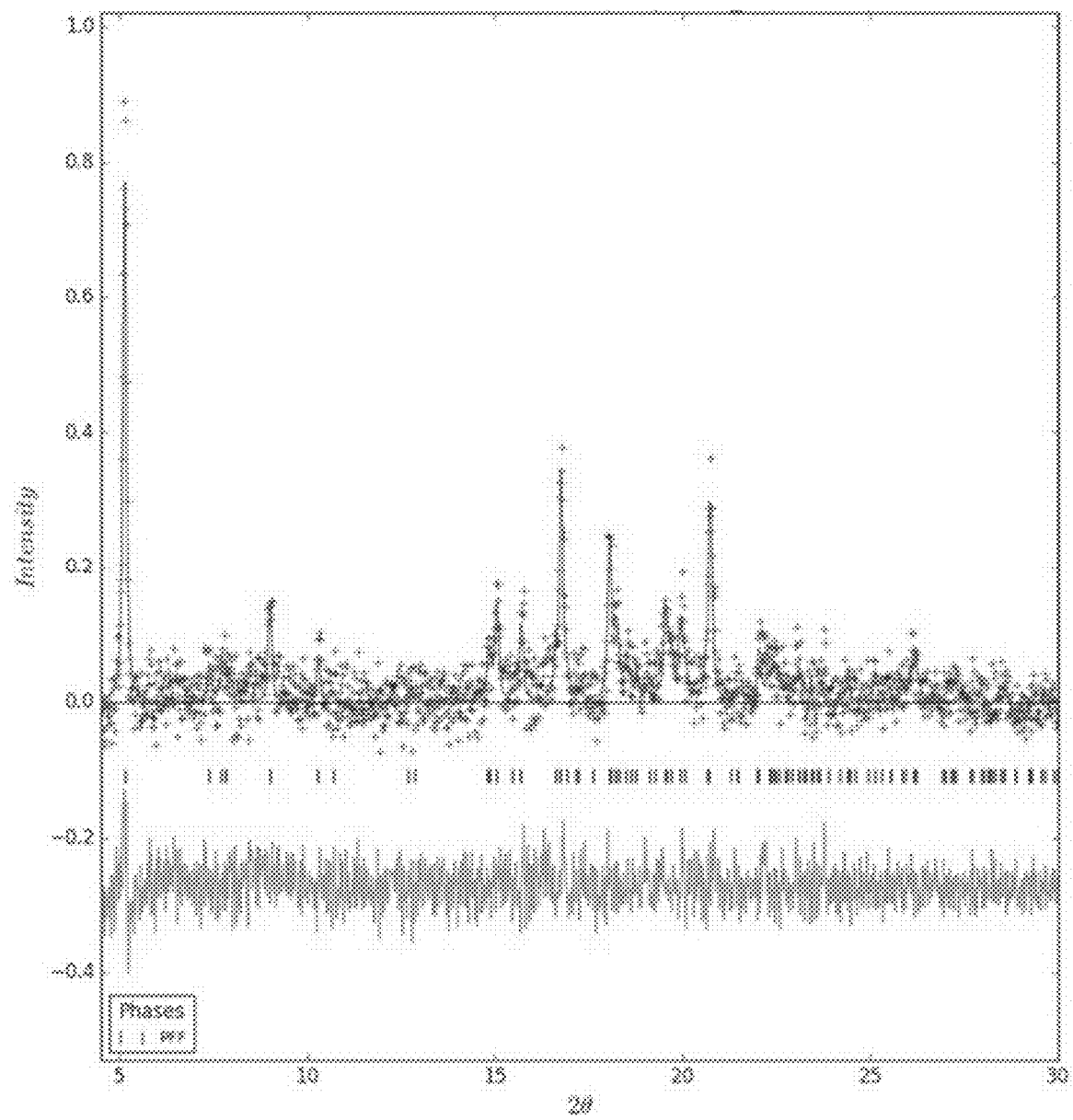
FIG. 13 presents a diffractogram for Pro-Phe-Phe fibers, including observed diffractogram (points marked by +), calculated diffractogram (line fitted to points), and the difference between observed and calculated data (line at bottom).

As shown in FIGS. 12 and 13, the X-ray diffraction powder pattern of Pro-Phe-Phe suggested monoclinic unit cells with a=5.330 Å, b=11.946 Å, c=34.360 Å and β=92.17°, which are considerably different from the typical diffraction of cross-β amyloids.

These results indicate stacking of distinctive units rather than β-strands, as also suggested by the secondary structure analysis.

To examine the molecular basis of fiber formation other than the canonical cross-β structure, Pro-Phe-Phe was crystallized.

As further shown in FIG. 12, the space group and unit cell parameters of the formed Pro-Phe-Phe crystals strongly resembled those of the Pro-Phe-Phe fibers, indicating a similar molecular organization.

The tripeptide crystalized in the $P2_1$ space group, with one tripeptide molecule in the asymmetric unit.

Figure 14:
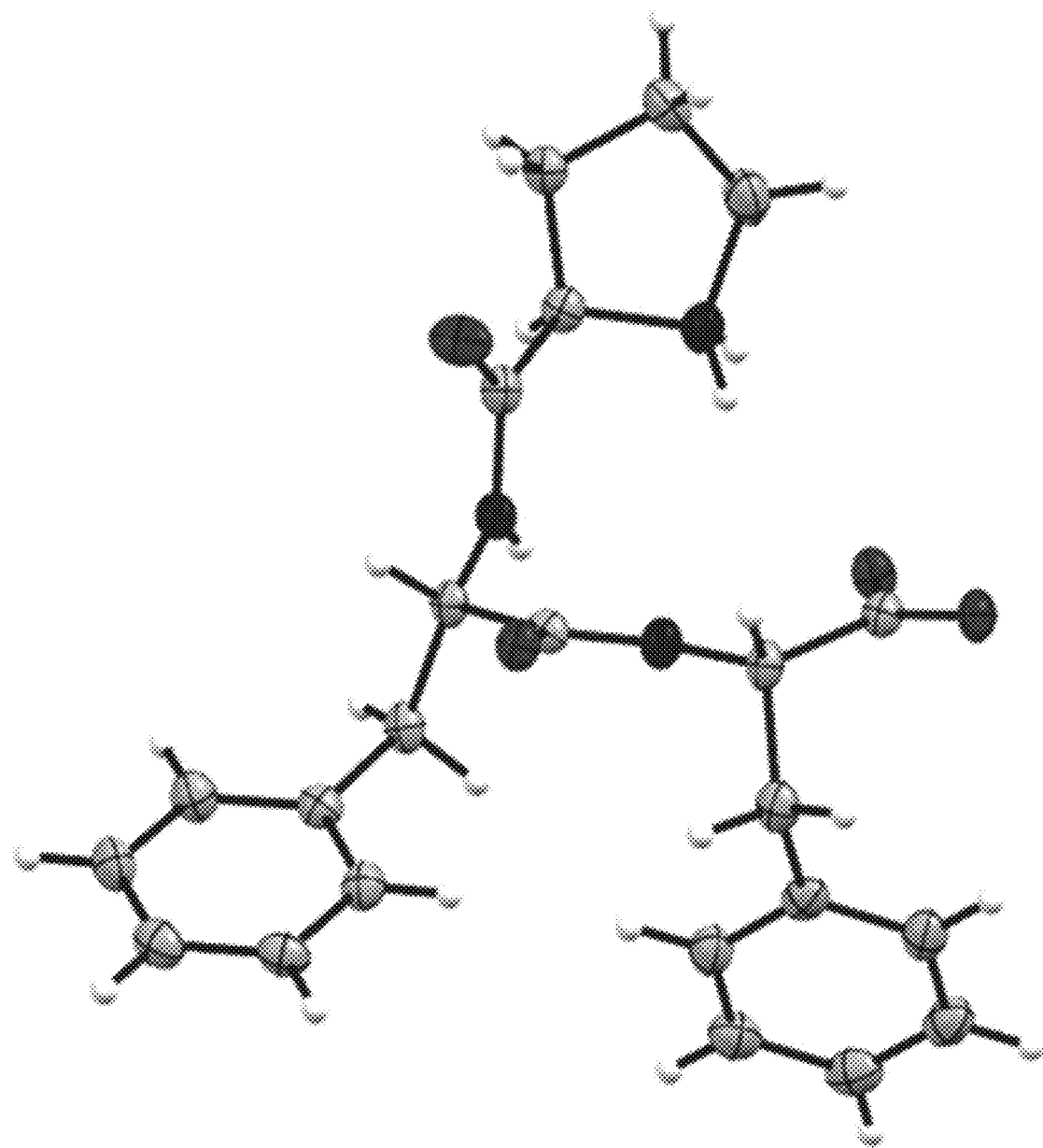
FIG. 14 presents the configuration of Pro-Phe-Phe in single crystal structure ($P2_1$ space group) as an ORTEP diagram of the asymmetric unit in 50% probability displacement ellipsoids.

As shown in FIG. 14, the two aromatic side chains of Pro-Phe-Phe arranged in the same face relative to the peptide backbone, creating a hydrophobic region, with the charged termini on the opposite site of the peptide backbone.

This result indicates that the Pro-Phe-Phe overall adopted an amphiphilic conformation with net segregation of hydrophobic and hydrophilic components on opposite sides of the backbone [Garcia et al., *Chem* 4:1-15 (2018)]. The torsion angles around the $Phe_2$ residue appeared to play a pivotal role in dictating the overall structural features.

As shown in FIG. 15, the allowed torsion angles of the $Phe_2$ residue of Pro-Phe-Phe were found to be localized within the right-handed helical region of the Ramachandran plot, with $\varphi_2$ and $\psi_2$ values of −78.5° and −38.9°, respectively.

As shown in FIGS. 16 and 17, two types of hydrogen bonds facilitated the crystal packing of Pro-Phe-Phe, head-to-tail interactions involving terminal amine and carboxylic acid groups (FIG. 16) and side-by-side stacking involving the amide groups (FIG. 17).

Figure 18:
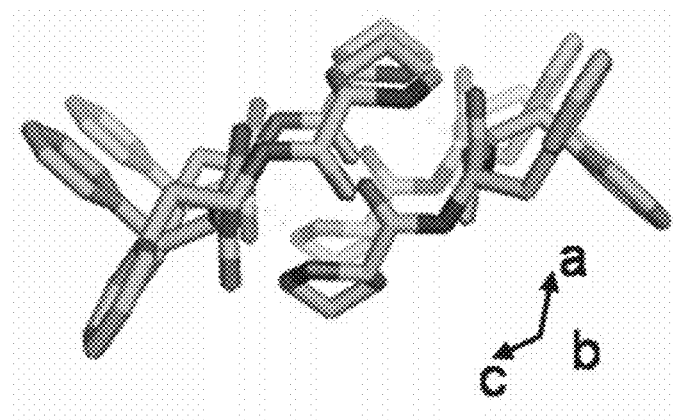
FIG. 18 presents a top view of a Pro-Phe-Phe helix in a single crystal structure.
Figure 19:
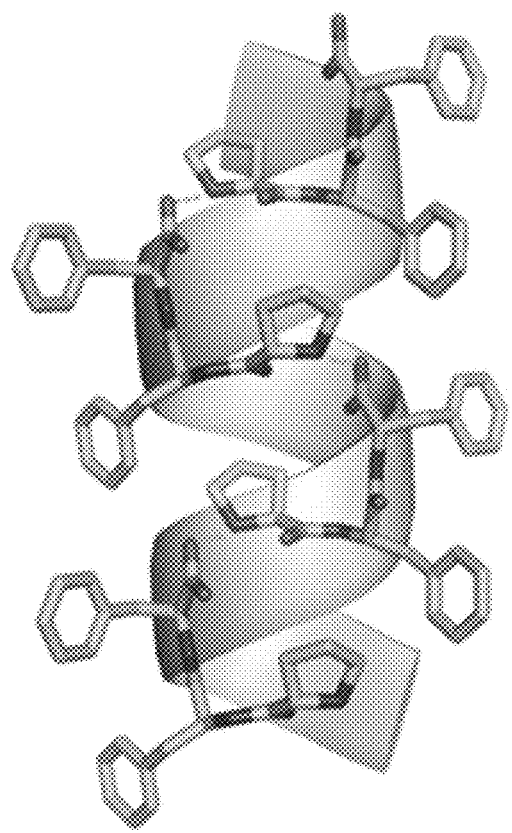
FIG. 19 presents a side view of a Pro-Phe-Phe helix in a single crystal structure (peptide helix is superimposed over an ideal helical model).

As shown in FIGS. 16, 18 and 19, in the crystallographic b-direction, Pro-Phe-Phe propagated through head-to-tail intermolecular hydrogen bonds, generating a helical arrangement of the peptide backbone.

As further shown in FIG. 18, a void space inside the helical framework is observable in top view presentation.

Tripeptides constituted from canonical amino acids and organized in helical assemblies have only very rarely been reported [Parthasarathy et al., *Proc Nat Acad Sci USA* 87:871-875 (1990)]. Moreover, the three residues in such tripeptides were not sufficient to complete a helical turn, and at least one water molecule was required as an additional residue to link the translationally related peptide segments along the helical axis.

In contrast, the Pro-Phe-Phe tripeptide forms a helical assembly without any additional solvent molecules in the crystal, making it a highly unique organization. It is believed that this is the first report of a supramolecular helical tripeptide composed only of natural amino acids. The fourth residue required to complete a single helical turn is fulfilled by the terminal H-bonded addition of the next peptide molecule. As a result, the directionality of the amide groups essential for internal i+4→i H-bond parallel to the α-helix axis is changed. Instead, the amide H-bonds are oriented in the perpendicular direction of the helix. Thus, although the torsion angle of $Phe_2$ was found to be localized within the right-handed helical region of the Ramachandran plot, the H-bonding network produced a unique structural arrangement, not previously observed in any biological system.

Figure 20A:
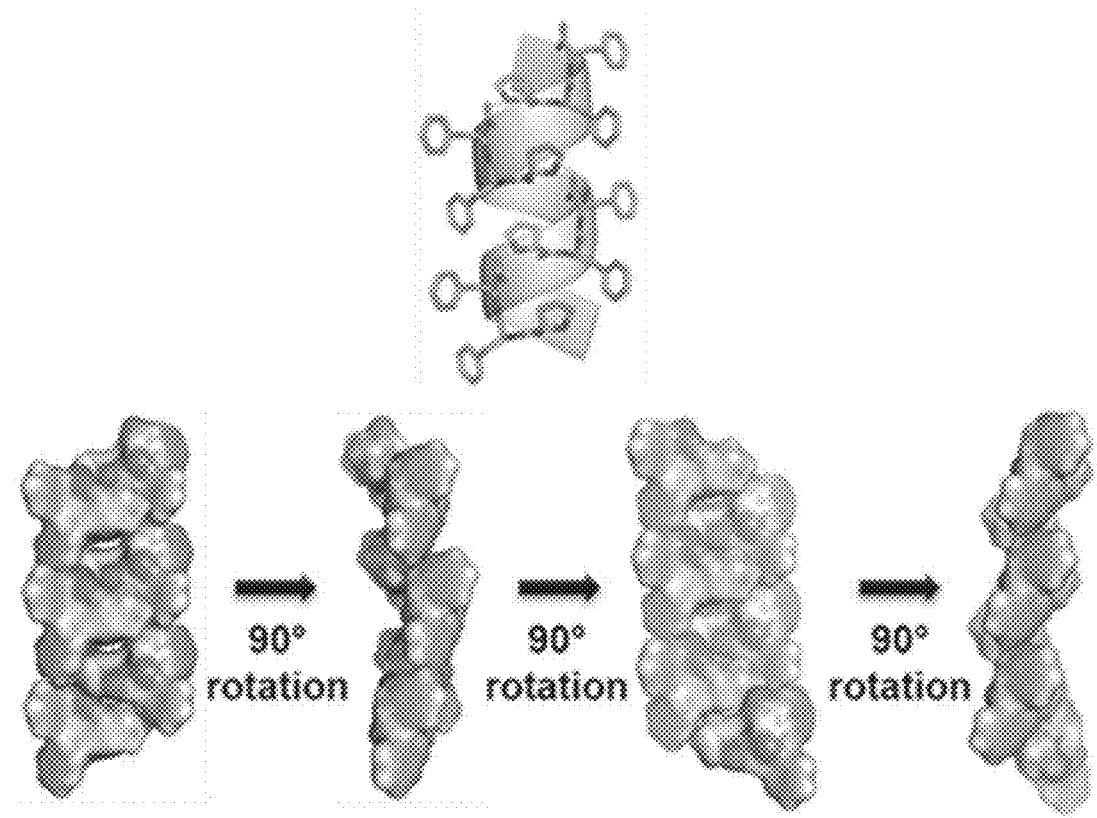
FIGS. 20A-20C present images depicting a crystal structure of Pro-Phe-Phe, wherein surfaces of a single helix are shown by 90° rotations (FIG. 20A), indicating that the two faces of the helix are hydrophobic in nature by exposing aromatic rings of Phe residues and the other two faces are hydrophilic in nature by extending the amide groups; crystal packing of Pro-Phe-Phe down the elongated axis (left) exhibits stacking of helical sheets through hydrophobic interaction (FIG. 20B), and rotation of 90° (right) shows hydrophilic interactions among the helical stands inside an individual sheet; and a unit cell measurement of the crystal with respect to crystal morphology, in which a single crystal is mounted on a MiTeGen loop (FIG. 20C), the crystal is highlighted in white box and the respective cell axes are further depicted (the morphological long axis of the crystal is aligned along the crystallographic an axis of the unit cell).
Figure 20B:
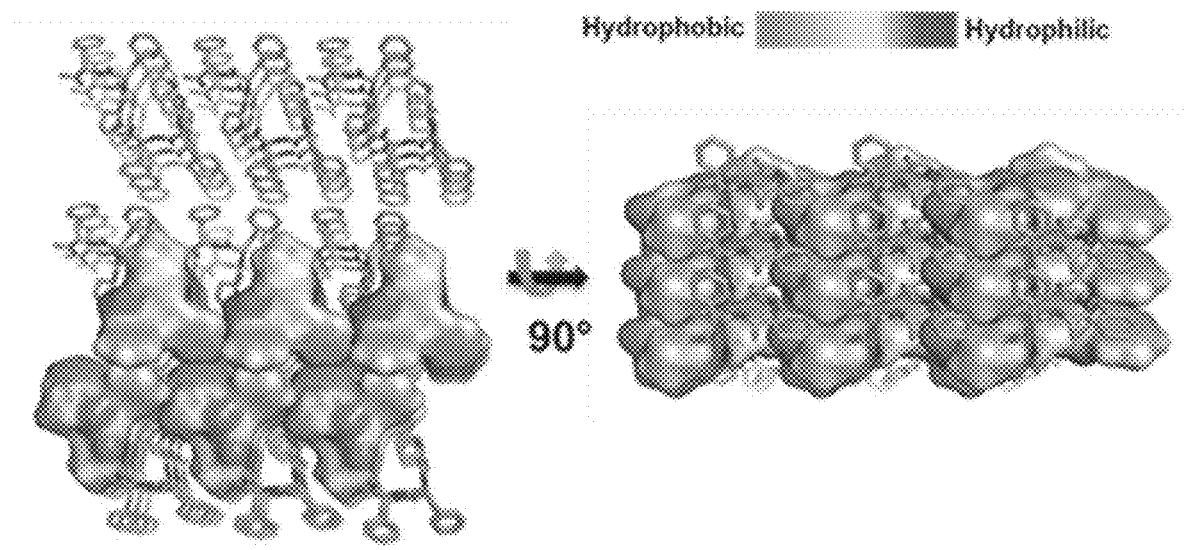
Figure 20C:
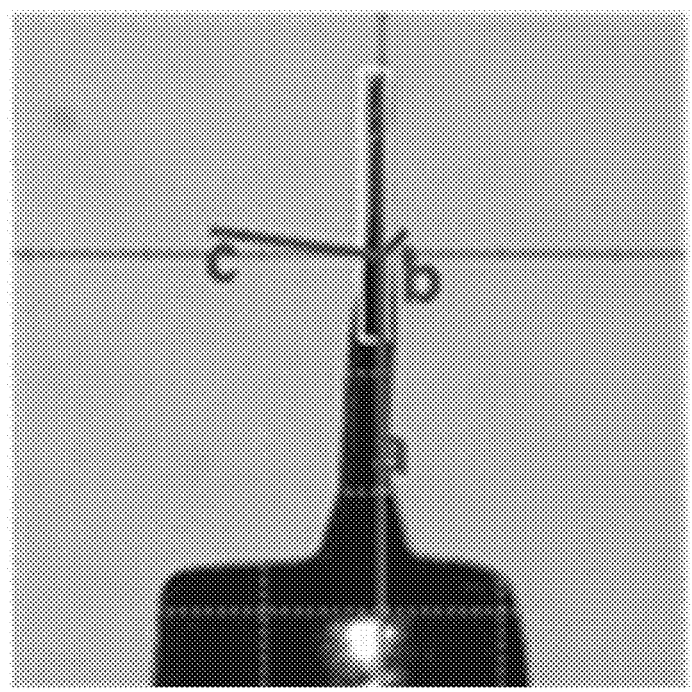

As shown in FIGS. 20A-20C, in the resulting helical structure, the center of the helix is composed of a hydrophilic segment and the surface of the helix comprises hydrophobic Phe residues, as observed in the be plane.

As shown in FIG. 21, adjacent helices run laterally with respect to each other in the c-direction, with their interface stabilized by intermolecular interactions between the aromatic moieties of Phe residues arranged in an approximate T-shape, as commonly observed in helical peptide and protein crystals.

These results indicate that the amphipathic conformations of Pro-Phe-Phe formed a dry "aromatic zipper" arrangement, which can hold the superstructures together and stabilize the helical assemblies [Garcia et al., *Chem* 4:1-15 (2018)]. In the perpendicular direction (a-direction), nearby helices interacted in a parallel pattern by alternatively incorporating amide NH and CO groups in H-bonding, stacking into a closely packed helical-sheet [Lampel et al., *Science* 356:1064-1068 (2017)].

As shown in FIGS. 20A-20C and 22, as the helical strands run perpendicular to the stacking axes, addition of hydrogen-bonded Pro-Phe-Phe molecules in the growing sheet accounted for the formation of elongated fiber structures.

Several previous studies have explored the self-assembly of longer helical peptides into coiled coil nanofibers in which helices were orientated parallel to the fiber axis

[Pandya et al., *Biochemistry* 39:8728-8734 (2000); O'Leary et al., *Nat. Chem.* 3:821-828 (2011)]. Longitudinal propagation of the coiled coil bundles was reported to lead to formation of the fibers. A recent study reported the self-assembly of a range of tripeptides, Phe-Xaa-Phe (with alternating stereochemistry), displaying β-sheet structures and organized into a parallel-to-fiber arrangement [Garcia et al., *Chem* 4:1-15 (2018)].

Figure 23A:
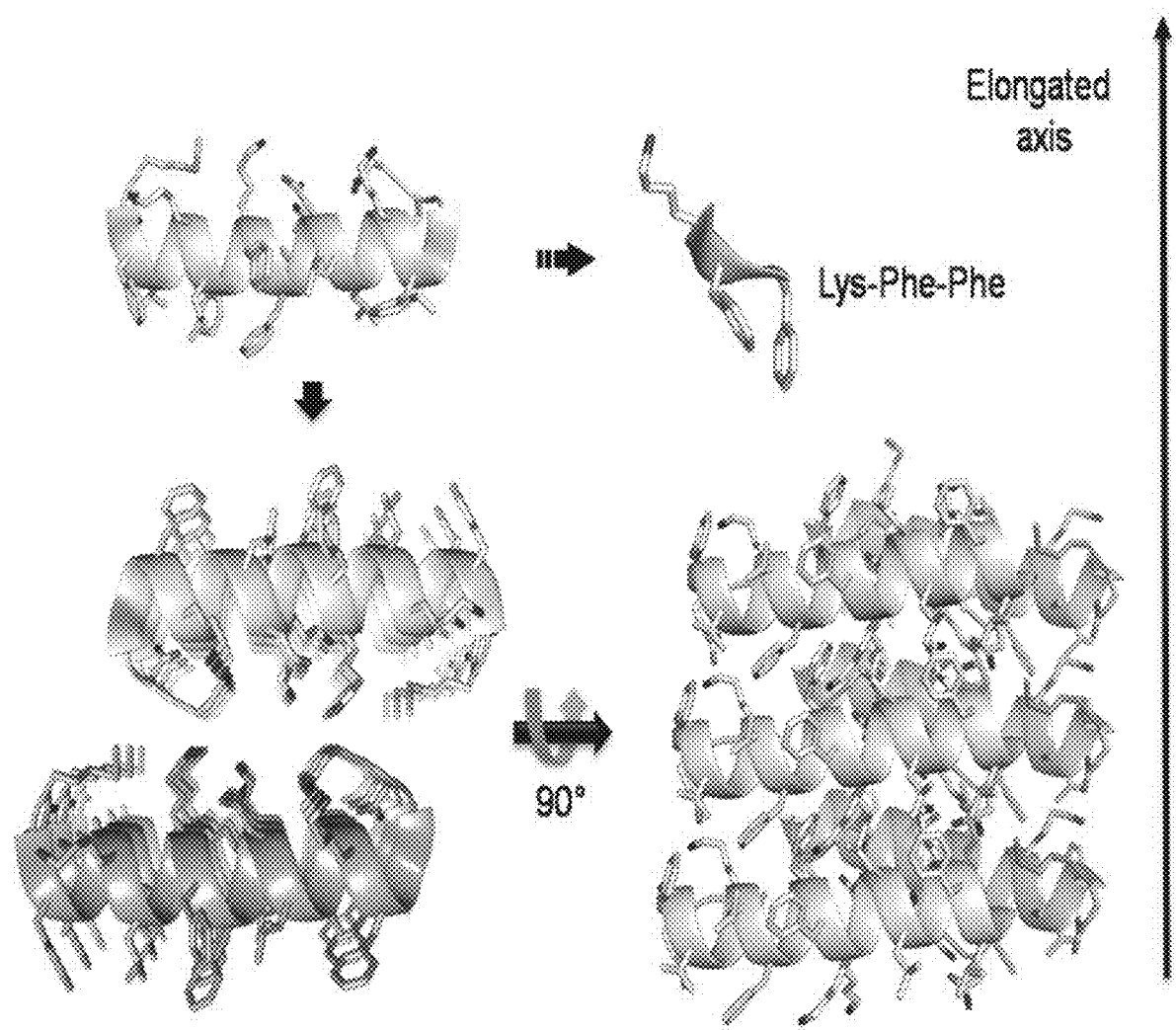

However, with the exception of the direction of the internal amide H-bonds, fiber formation by the tripeptide Pro-Phe-Phe, comprising a helical arrangement perpendicular to the fiber axis, more closely resembles the fiber formation by the 22-amino acid PSMα3 peptide, as described by Tayeb-Fligelman et al. [*Science* 355:831-833 (2017)]. The orientation of the PSMα3 peptide and its comparison to that of Pro-Phe-Phe are shown in FIGS. 23A-23C. The allowed torsion angle around Phe$_2$ of the central core Lys-Phe-Phe residues in PSMα3 is also in the right handed helical region of the Ramachandran plot, confirming the Pro-Phe-Phe tripeptide as a minimalistic model for the newly defined structural motif.

In comparison, as shown in FIGS. 22 and 23B, the helical sheets of the Pro-Phe-Phe tripeptide run parallel to the elongated axes. Hydrophobic dry steric zipper interactions between aromatic rings create a continuous row of combined sheets composed of helices, forming a cross-helical architecture, with nearby sheets oriented parallel to each other. As these dry steric zipper assemblies of sheets expose bulky phenyl rings on both sides, the inter-sheet distance is 11.5 Å.

The inter-strand distance of 5.3 Å resembles the characteristic meridional diffraction for cross-β structure of 4.9 Å [Nelson et al., *Nature* 435:773-778 (2005)], resulting in an overall cross-helical packing arrangement (e.g., as depicted in FIGS. 23B and 23C). An important aspect of this cross-helix structure is the perpendicular orientation of the amide bond relative to the helix axis, a counterintuitive packing compared to conventional helices and the PSMα3 cross-helix.

Without being bound by any particular theory, this configuration may be explained by analyzing the conventional helical folding pathway of disordered polypeptides, which follows a nucleation and growth model. The nucleation event, which is rate-limiting and energetically unfavorable, is dominated by short stretches of the amino acid (preferably 3-4 residues long), which have a very strong preference for φ, ψ angles corresponding to the helical region of the Ramachandran plot, with minimal contribution of intra-helix H-bonding. Accordingly, the backbone dihedral angles and direction of the peptide chain are more significant than H-bonding direction in determining the helical axis of short nucleating tripeptides.

To understand whether this cross-helical conformation is unique to the Pro-Phe-Phe tripeptide or a robust structure which represents a more generic conformation, the tripeptide sequence was modified by replacing proline with hydroxyproline (Hyp). The hydroxylation of proline plays an important role in the stabilization of collagen triple helix, a central structural element in connective tissues, underlying its well-adapted physical properties [Bella et al., *Science* 266:75-81 (1994)]. Structural modifications of short peptide sequences are often reported to abrogate the backbone conformation, as well as the higher order packing of the relevant peptide building blocks [Pellach et al., *Chem. Mater.* 28:4341-4348 (2016)].

As shown in FIGS. 15 and 24A-24C, Hyp-Phe-Phe exhibited remarkable similarity to Pro-Phe-Phe, in both backbone conformation and supramolecular organization, in spite of the additional H-bonding site, as determined by X-ray single crystal analysis.

As further shown in FIGS. 24A-24C, the formation of helical sheet and cross-helical architecture in Hyp-Phe-Phe was also found to be similar to Pro-Phe-Phe.

Figure 25A:
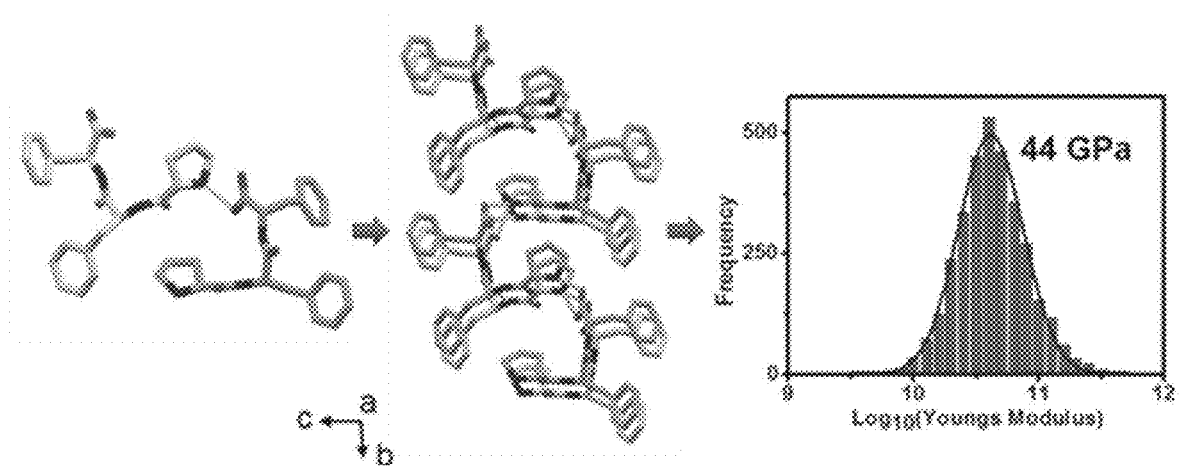
FIGS. 25A and 25B present schematic images depicting inter-strand H-bonding in the crystal packing of tripeptides (left) and histograms showing Young's modulus of tripeptides (right), for Pro-Phe-Phe (FIG. 25A) and Hyp-Phe-Phe (FIG. 25B) tripeptides.
Figure 25B:
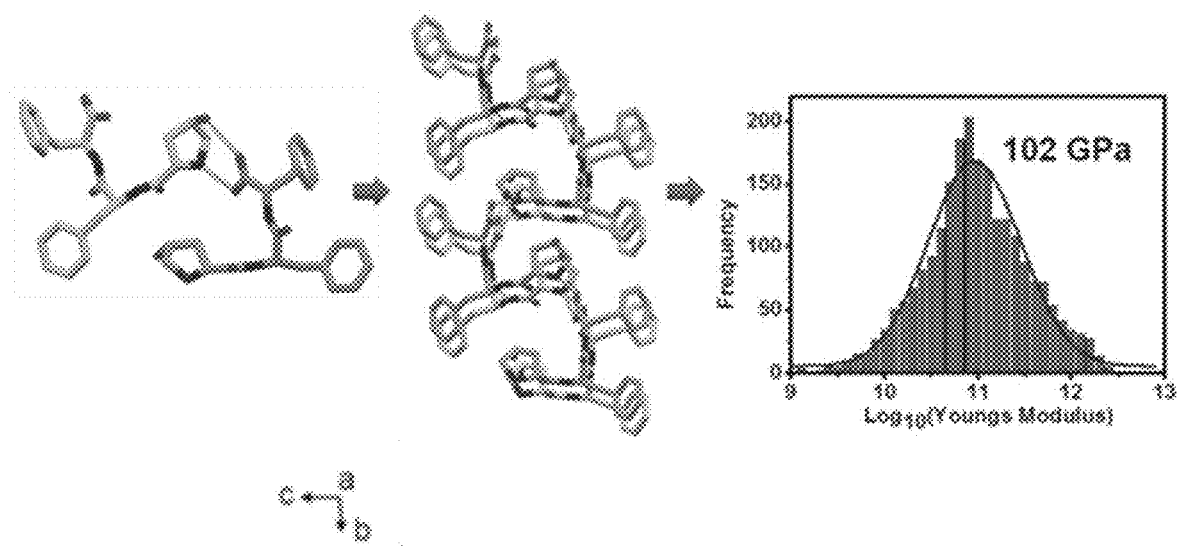

As shown in FIGS. 25A and 25B, the additional H-bonding site of hydroxyproline in Hyp-Phe-Phe was utilized through H-bond formation between adjacent strands, suggesting that helical sheets of Hyp-Phe-Phe are more tightly packed than those of Pro-Phe-Phe.

This result clearly indicates that the helical conformation and supramolecular cross-helical assembly of Pro-Phe-Phe are indeed characteristics of the peptide backbone, which are not affected by side chain modifications.

The experimental data for Pro-Phe-Phe and Hyp-Phe-Phe are summarized in Table 1 below.

TABLE 1

Data and refinement statistics for Pro-Phe-Phe and Hyp-Phe-Phe

| Crystal data | Pro-Phe-Phe | H-Phe-Phe |
|---|---|---|
| Chemical formula | C23 H27 N3 O4 | C23 H27 N3 O5 |
| Mr | 409.47 | 425.47 |
| Crystal system | Monoclinic | triclinic |
| Space group | P2$_1$ | P1 |
| a (Å) | 5.3214(1) | 5.4321(9) |
| b (Å) | 11.5689(1) | 11.891(1) |
| c (Å) | 17.0398(1) | 16.765(2) |
| α (°) | 90 | 84.57(1) |
| β (°) | 97.2170(10) | 83.00(1) |
| γ (°) | 90 | 89.867(1) |
| V (Å$_3$) | 1040.71(2) | 1070.0(3) |
| Z, Z' | 2 | 2 |
| μ (mm$^{-1}$) | 0.096 | 0.771 |
| Temperature (K) | 100(2) | 100(2) |
| Data collection | | |
| Diffractometer | Rigaku XtaLAB Pro: Kappa dual home/near | Rigaku XtaLAB Pro: Kappa dual home/near |
| Crystal size (mm) | 0.27/0.10/0.20 | 0.262/0.090/0.016 |
| Absorption correction | multi-scan | multi-scan |
| Tmin, Tmax | 0.826, 0.985 | 0.684, 1.000 |
| N$_{measured}$ | 17218 | 9432 |
| N$_{observed}$ [I > 2σ(I)] | 4446 | 4441 |
| R$_{int}$ | 0.0373 | 0.0782 |
| θ$_{max}$ (°) | 79.898 | 52.852 |
| Refinement | | |
| R[F2 > 2σ(F2)] | 0.0383 | 0.0834 |
| wR(F2) | 0.0957 | 0.2247 |
| Goodness-of-fit | 1.105 | 1.040 |
| No. of reflections | 4446 | 4441 |
| No. of parameters | 271 | 561 |
| No. of restraints | 1 | 1 |
| H-atom treatment | H-atom parameters constrained | H-atom parameters constrained |

In view of the unique cross-helical organization of both Pro-Phe-Phe and Hyp-Phe-Phe, and specifically the further reinforcement of the inter sheet interaction by the additional H-bond in the latter tripeptide, the macroscopic manifestation of such a packing module was investigated, using an indentation-type AFM experiment.

As further shown in FIG. 25A, the Young's modulus of the Pro-Phe-Phe crystals was found to be about 44 GPa, indicating a remarkable stiffness of the cross-helical conformation.

Figure 27:
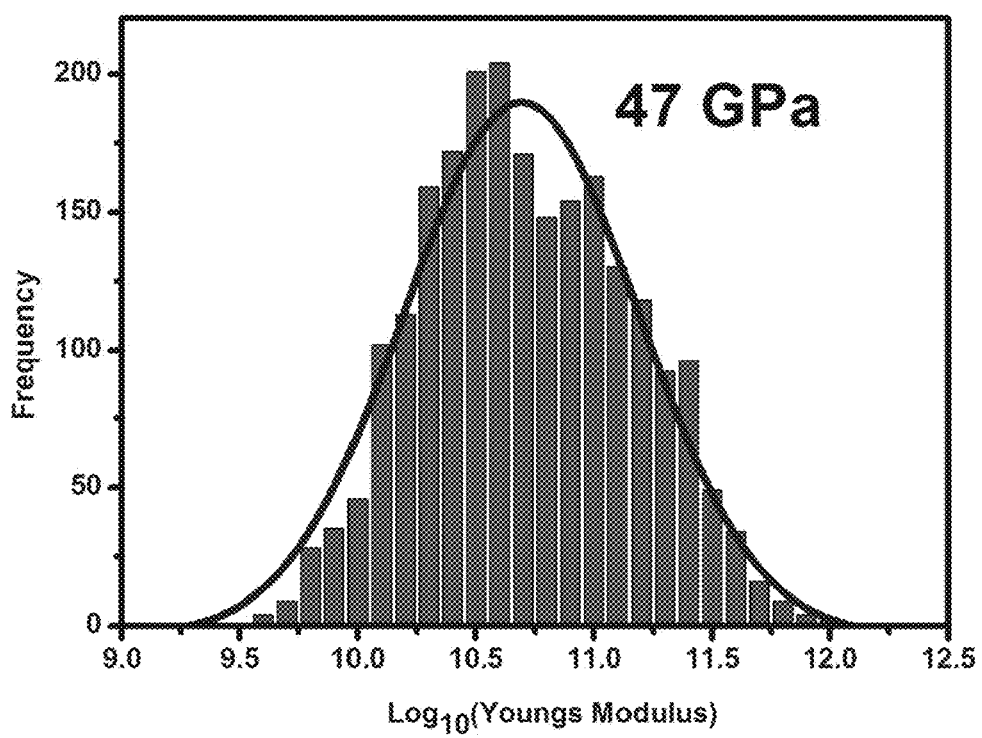
FIG. 27 presents a histogram showing a distribution of Young's modulus of Pro-Phe-Phe self-assembled fibers.

As shown in FIG. 27, the Young's modulus of self-assembled Pro-Phe-Phe fibers was about 47 GPa, similar to that of the crystal state.

These results indicate similar molecular arrangement and robustness in Pro-Phe-Phe crystals and fibers.

Figure 26:
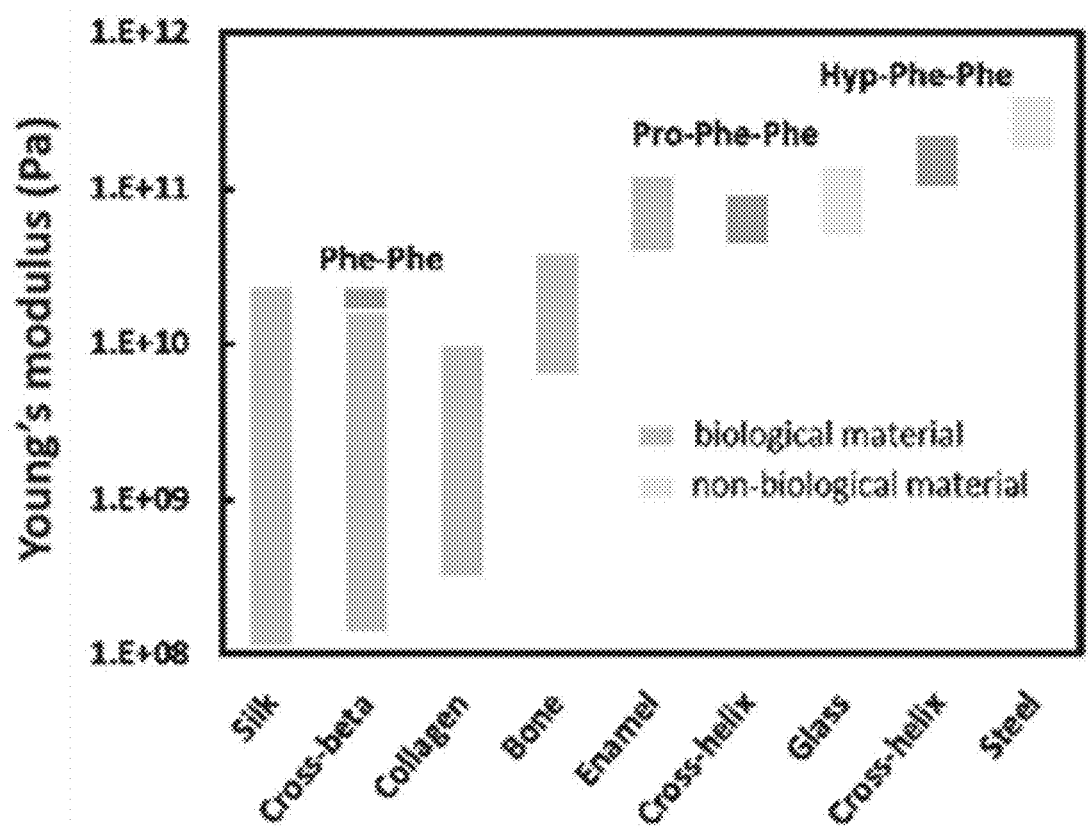
FIG. 26 presents a graph showing ranges of Young's moduli of Phe-Phe, Pro-Phe-Phe and Hyp-Phe-Phe (dark gray), and of various biological and non-biological materials for comparison.

In comparison, as shown in FIG. 26, nanotubes of the Phe-Phe dipeptide, the minimal core recognition motif of amyloid-β and one of the shortest and stiffest β-sheet based proteinaceous structures, was reported to exhibit a Young's modulus of only 19 GPa [Kol et al., Nano Lett 5:1343-1346 (2005)].

Moreover, as shown in FIG. 25B, incorporation of the hydroxyl group into the side chain to generate Hyp-Phe-Phe significantly increased the stiffness, resulting in a Young's modulus of 102 GPa.

As further shown in FIG. 26, the Young's modulus of Hyp-Phe-Phe is comparable to that reported for the mechanically rigid collagen matrix [Knowles & Buehler, Nat Nanotechnol 6:469-479 (2011)].

Figure 28:
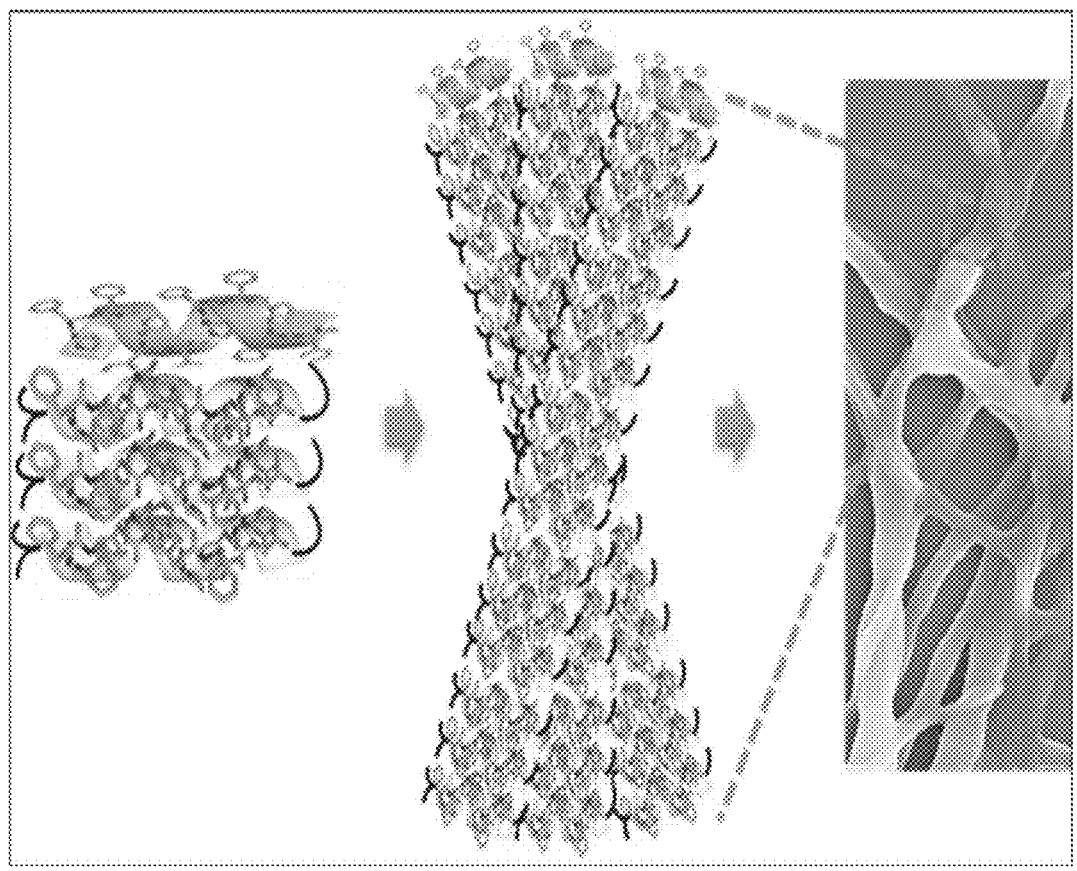
FIG. 28 presents a schematic model of a fibrillar assembly composed of cross-helical units.

FIG. 28 shows a proposed correlation between cross-helical units and observed fibrillar morphology.

Without being bound by any particular theory, it is believed the increase in stiffness associated with hydroxyproline is due to stabilization through additional H-bonds along the long axis.

Taken together, these results indicate that the cross-helical organization of the tripeptides afforded one of the stiffest biological materials. Importantly, even in such a short sequence, it was possible to modulate the robustness of the higher order assemblies in a predictable manner through side-chain modification.

Atomic level understanding of supramolecular peptide assembly is critical not only for the design of functional biomaterials, but also for uncovering the role of the core recognition motifs in physiological self-organizing systems. The short interdigitated dry steric zipper represents a fundamental structural motif conferring exceptional stability to cross-β amyloids [Nelson et al., Nature 435:773-778 (2005)]. The cross-helical domain stabilized by dry steric zipper is common to the packing of both the minimal Pro-Phe-Phe tripeptide and the much longer PSMα3 peptide. Thus, the organization into cross-helical structural elements emerges as an additional major paradigm for peptide aggregation, analogous to the cross-β architectural design. Furthermore, unlike many cross-β modules, the minimal cross-α motif described here allowed the rationally designed modulation of the structural features at the molecular level, resulting in higher order organization with predictable sequence-structure relationship. Thus, this minimal motif can be manipulated to display unique biophysical characteristics at the bulk state. Finally, the single crystal X-ray analysis presented here could pave the way for the future design of modular cross-helical self-assembling nanostructures by incorporating Pro-Phe-Phe or its variants in peptide sequences.

Example 2

Effect of Sequence on Helical Configuration of Tripeptides

The generic nature of the helical conformation of the Pro-Phe-Phe tripeptide backbone (as described in Example 1) was further investigated by sequentially mutating the terminal residues with an intrinsic helix stabilizing amino acid, Ala, while conserving the central Phe, which adopted dihedral angles characteristic of helical conformation. The conformations of the modified sequences, Ala-Phe-Phe and Ala-Phe-Ala, were analyzed in atomic details by single crystal X-ray crystallography.

In addition, the effect of sequence shuffling of the Pro-Phe-Phe tripeptide was examined by studying the tripeptides Phe-Pro-Phe and Phe-Phe-Pro.

Figure 29A:
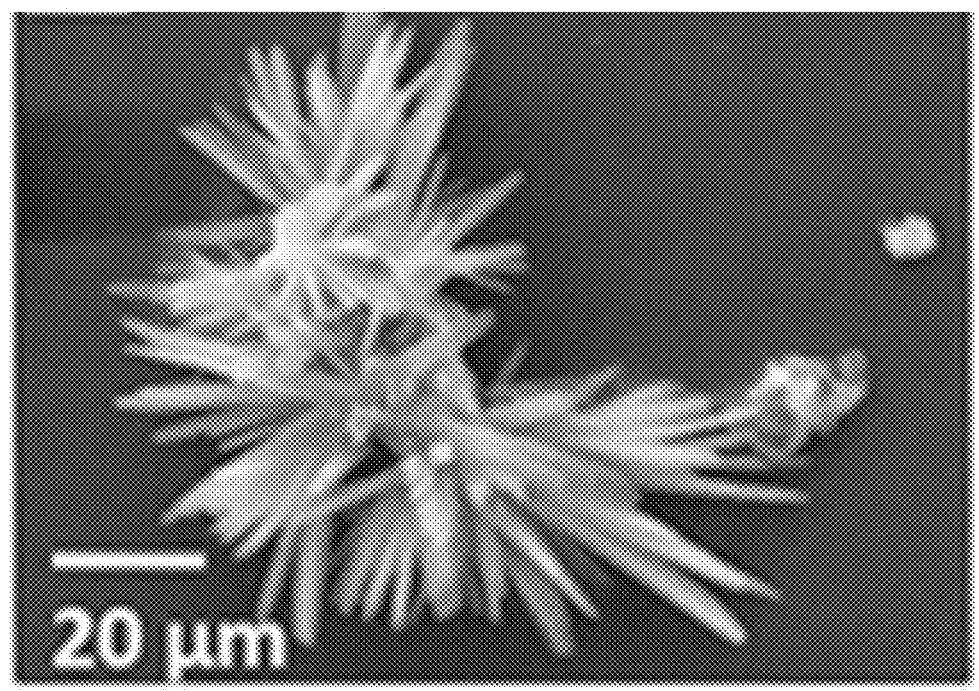
FIGS. 29A-29F present a HR-SEM micrograph of Ala-Phe-Phe tripeptide flakes prepared in phosphate buffer at pH 7.4 (FIG. 29A), an FTIR spectrum of Ala-Phe-Phe (FIG. 29B), a CD spectrum of Ala-Phe-Phe in solution (FIG. 29C), and images depicting asymmetric unit (FIG. 29D), antiparallel β-sheet structure of the tripeptide through intermolecular N—H . . . O hydrogen bonds along the a-direction (FIG. 29E), and cross-β structure (FIG. 29F) of Ala-Phe-Phe single crystals.

As shown in FIG. 29A, Ala-Phe-Phe self-assembled in phosphate buffer at pH 7.4, resulting in flake-like morphologies, which were completely different from the helical fibers of Pro-Phe-Phe.

The secondary conformation of the Ala-Phe-Phe assembled structures was analyzed by FTIR and CD spectroscopy.

Figure 29B:
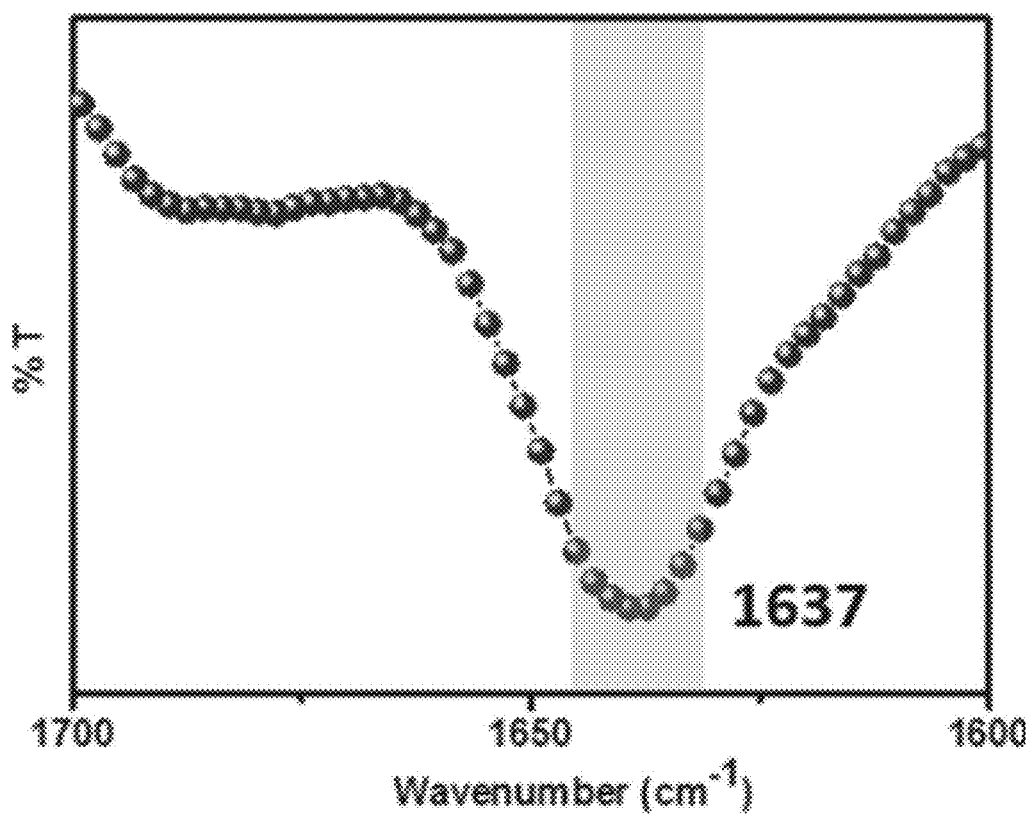

As shown in FIG. 29B, the FTIR spectrum for Ala-Phe-Phe exhibited a sharp amide I band at 1637 cm$^{-1}$, in contrast to the band at 1647 cm$^{-1}$ observed for Pro-Phe-Phe.

This result indicates the presence of a β-sheet structure in Ala-Phe-Phe [Yang et al., Nat Protoc 10:382-396 (2015); Miyazawa & Blout, J Am Chem Soc 83:712-719 (1961)].

Figure 29C:
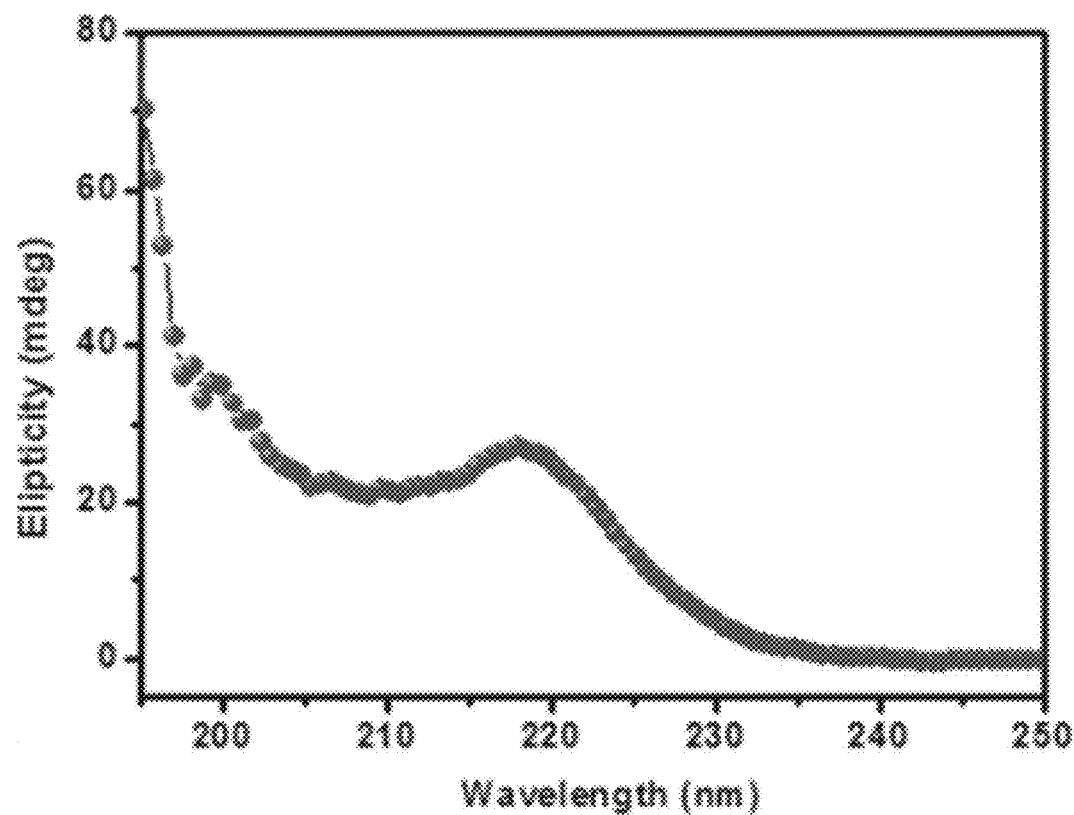

As shown in FIG. 29C, the CD spectrum of the Ala-Phe-Phe self-assemblies exhibited positive peaks near 220 nm.

Such peaks are believed to be associated with the presence of aromatic residues [Handelman et al., J Pept Sci 20:487-493 (2014); Castelletto et al., Sci Rep 7:43637 (2017)].

The conformation and self-assembly at the atomic level were further confirmed by X-ray crystallography of the tripeptide. Single crystals suitable for X-ray diffraction were obtained by slow evaporation of the methanol-water solution. Two tripeptide molecules were crystalized with one molecule of trifluoroacetic acid and one water molecule in the asymmetric unit in P1 space group. No intramolecular H-bond was detected. The two Phe side chains were arranged in opposite direction with respect to the peptide backbone. The torsion angles around the Phe$_2$ residue appeared to play a pivotal role in determining the overall structural features.

Figure 29D:
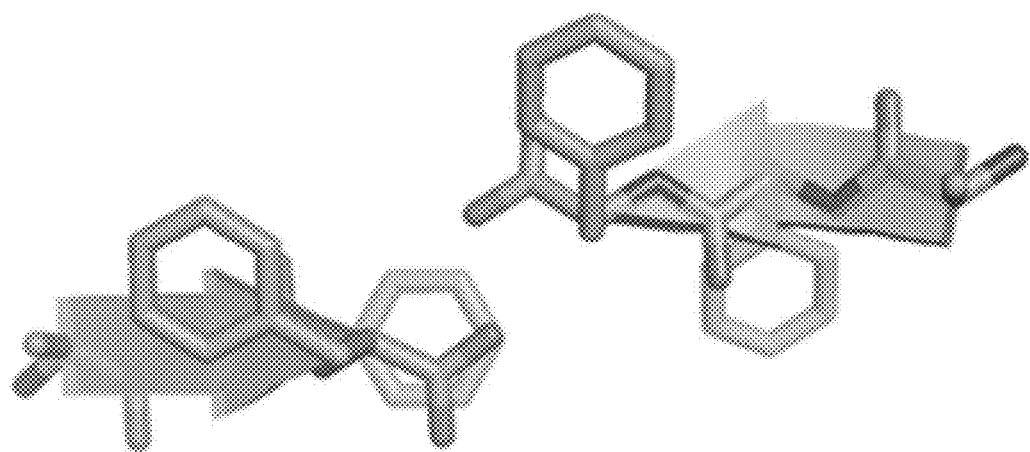

As shown in FIGS. 15 and 29D, the allowed torsion angles of the Phe$_2$ residue in the modified peptides were constrained within the β-sheet region of the Ramachandran plot, with $\varphi_2$ and $\psi_2$ values of −144.20° and 150.81°, respectively, for molecule A of Ala-Phe-Phe, and −127.95° and 135.10°, respectively, for molecule B of Ala-Phe-Phe.

Figure 29E:
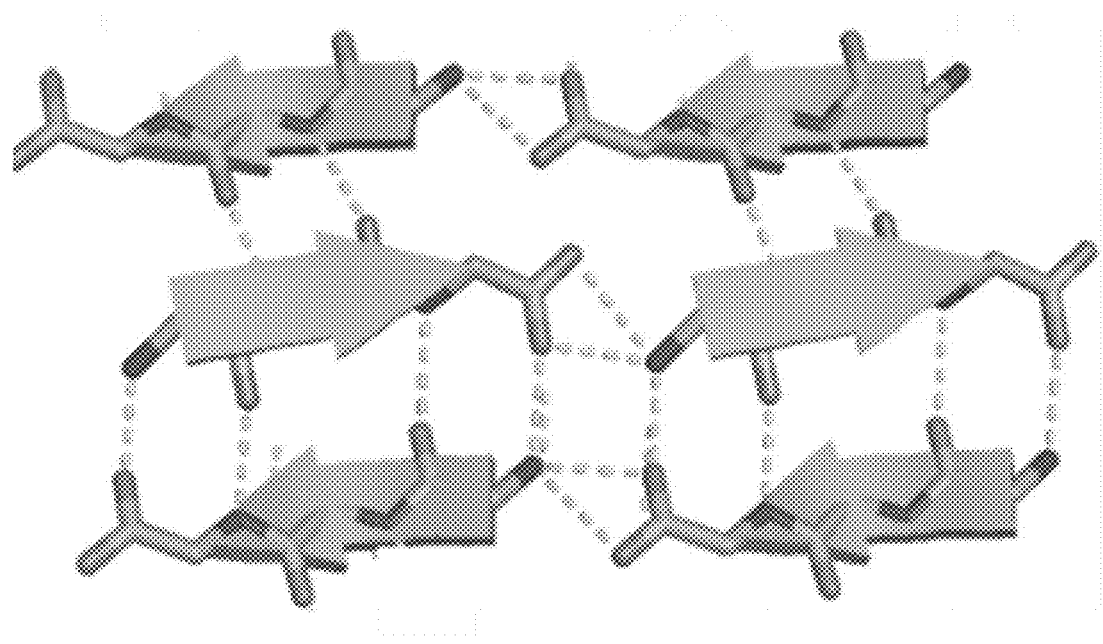

As shown in FIG. 29E, in the crystallographic a-direction, β-strands interacted with adjacent strands through intermolecular H-bonds and stacked in antiparallel manner, thereby producing an antiparallel β-sheet conformation.

Figure 29F:
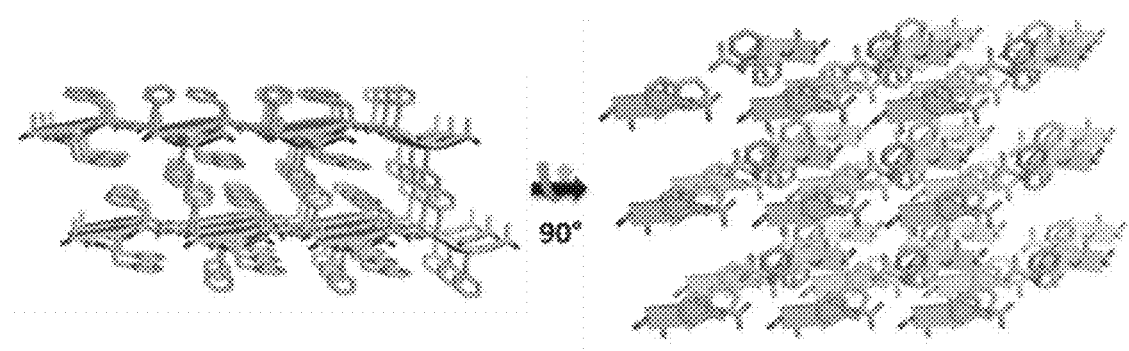

As shown in FIG. 29F, adjacent β-sheets were stabilized through π-π interactions of aromatic residues and produced an aromatic zipper-like structure.

These results indicate that overall arrangement of Ala-Phe-Phe is a cross-β structure, a fundamental secondary structural module commonly observed in self-assembled nanostructures formed by short peptide sequences [Sawaya et al., Nature 447:453-457 (2007); Colletier et al., Proc Nat Acad Sci USA 108:16938-16943 (2011); Sikorski et al., Structure 11:915-926 (2003); Ye et al., PLoS One 7:e36382 (2012); Ilawe et al., Phys Chem Chem Phys 20:18158-18168 (2018)]. Thus, modification of Pro-Phe-Phe to Ala-Phe-Phe changes the secondary structure of the tripeptide from cross-helical to cross-β.

Further modification of the backbone was performed by replacing the terminal Phe residue with Ala, resulting in the Ala-Phe-Ala modified tripeptide.

Figure 30A:
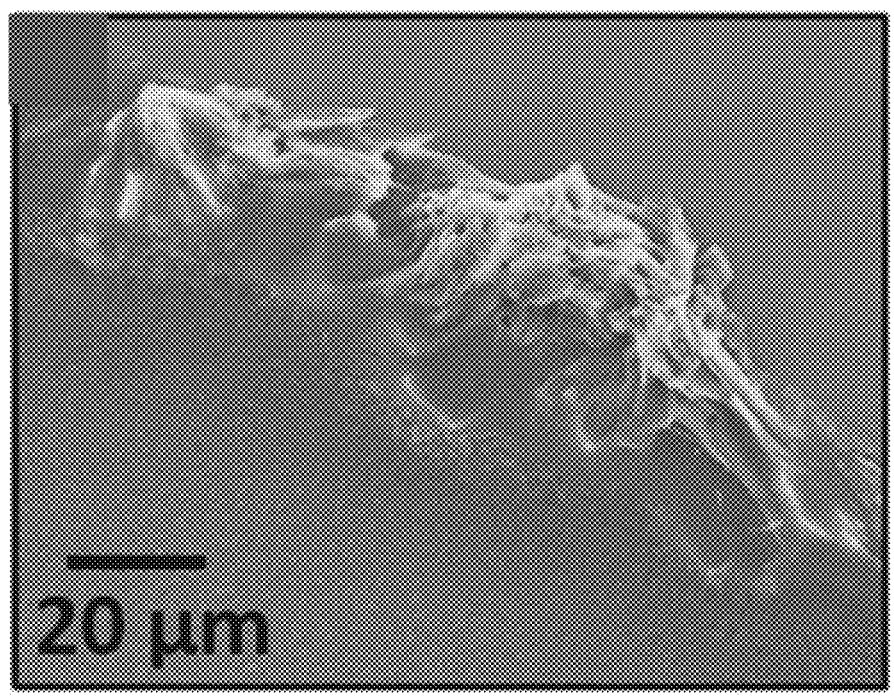
FIGS. 30A-30G present a HR-SEM micrograph of Ala-Phe-Ala tripeptide flakes prepared in phosphate buffer at pH 7.4 (FIG. 30A), an FTIR spectrum of Ala-Phe-Ala (FIG. 30B), a CD spectrum of Ala-Phe-Ala in solution (FIG. 30C), and images depicting asymmetric unit (FIG. 30D), β-strand (FIG. 30E), antiparallel β-sheet structure of the tripeptide through intermolecular N—H . . . O hydrogen bonds along the a-direction (FIG. 30F), and cross-β structure (FIG. 30G) of self-assembled Ala-Phe-Ala.

As shown in FIG. 30A, Ala-Phe-Ala failed to exhibit any apparent well-ordered morphology in phosphate buffer at pH 7.4, as observed by HRSEM imaging.

Figure 30B:
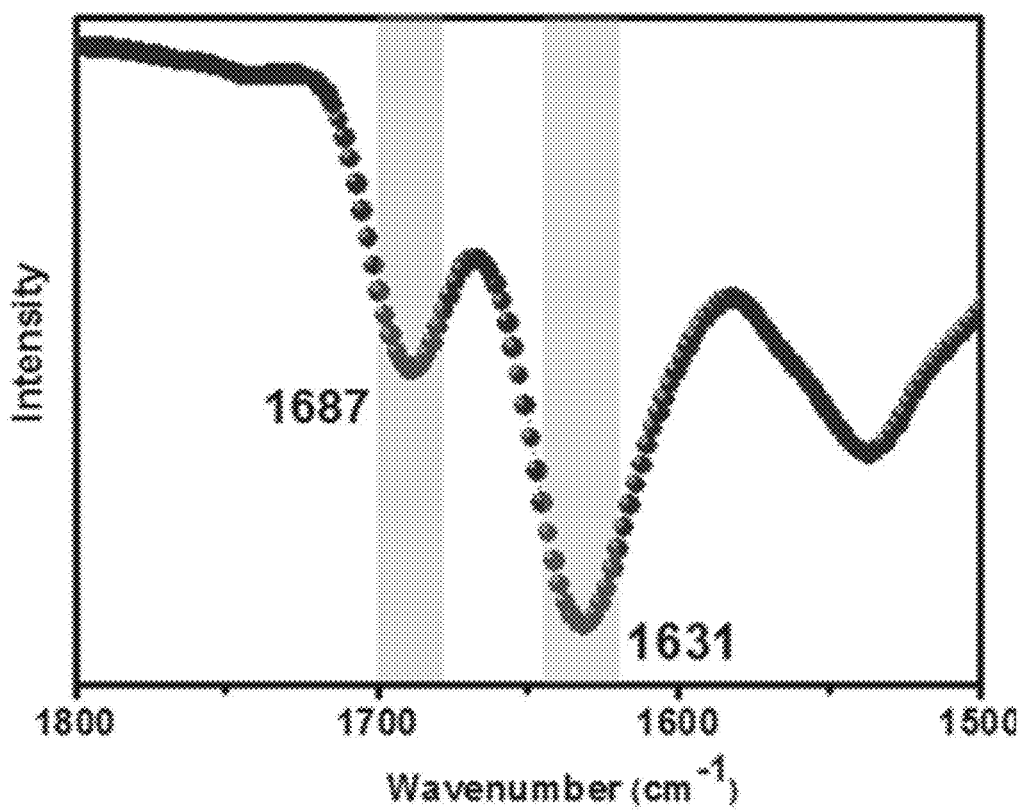

As shown in FIG. 30B, the FTIR spectrum of Ala-Phe-Ala exhibited a sharp amide I band at 1631 cm$^{-1}$ along with a shoulder at 1687 cm$^{-1}$.

This result indicates the predominant presence of a β-sheet structure in Ala-Phe-Ala [Yang et al., *Nat Protoc* 10:382-396 (2015); Miyazawa & Blout, *J Am Chem Soc* 83:712-719 (1961)].

Figure 30C:
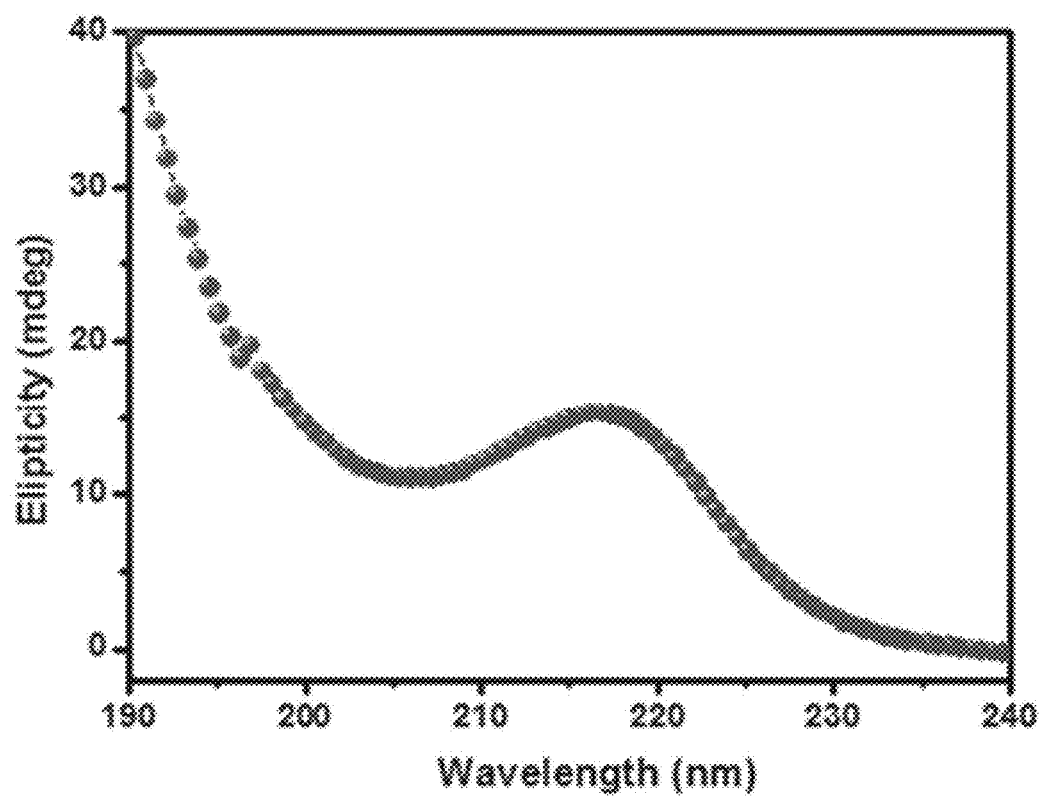

As shown in FIG. 30C, the CD spectrum of Ala-Phe-Ala tripeptide assemblies exhibited positive peaks near 220 nm, as did the CD spectrum of Ala-Phe-Phe.

Atomic level conformation was investigated by single crystal structure analysis. Single crystals suitable for X-ray diffraction were obtained by slow evaporation of a 9:1 methanol/water solution.

Figure 30D:
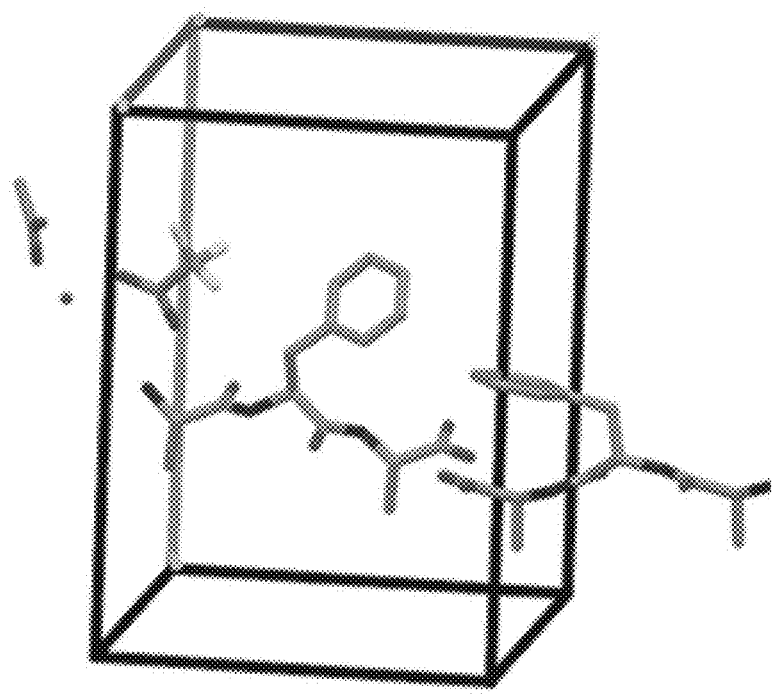

As shown in FIG. 30D, the asymmetric unit of Ala-Phe-Ala was found to consist of two tripeptide molecules along with one molecule of trifluoroacetic acid, acetic acid and water in the $P2_1$ space group. The two tripeptide molecules adopted a similar backbone conformation, except for a slight variation in the torsion angle. No intramolecular hydrogen bond was observed inside either of the two molecules.

Figure 30E:
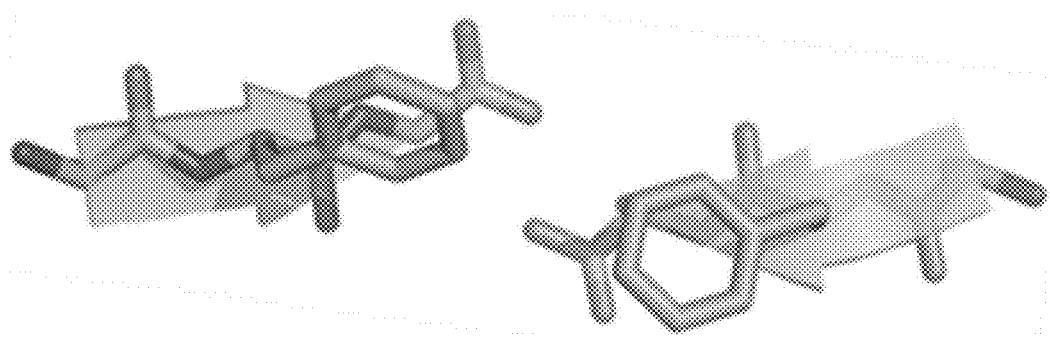

As shown in FIG. 30E, the allowed torsion angles of the $Phe_2$ residue in Ala-Phe-Ala were constrained within the β-sheet region of the Ramachandran plot, with $\varphi_2$ and $\psi_2$ values of −141.77° and 144.12°, respectively, for molecule A and −140.72° and 130.43°, respectively, for molecule B.

Previously reported conformational analysis of Ala-Phe-Ala based on both experimental and molecular dynamics studies also predicted torsion angles of an extended-β structure similar to those shown here [Motta et al., *Biochemistry* 44:14170-14178 (2005); Eker et al., *Proc Nat Acad Sci USA* 101:10054-10059 (2004); Pizzanelli et al., *J Phys Chem B* 114:3965-3978 (2010)].

Figure 30F:
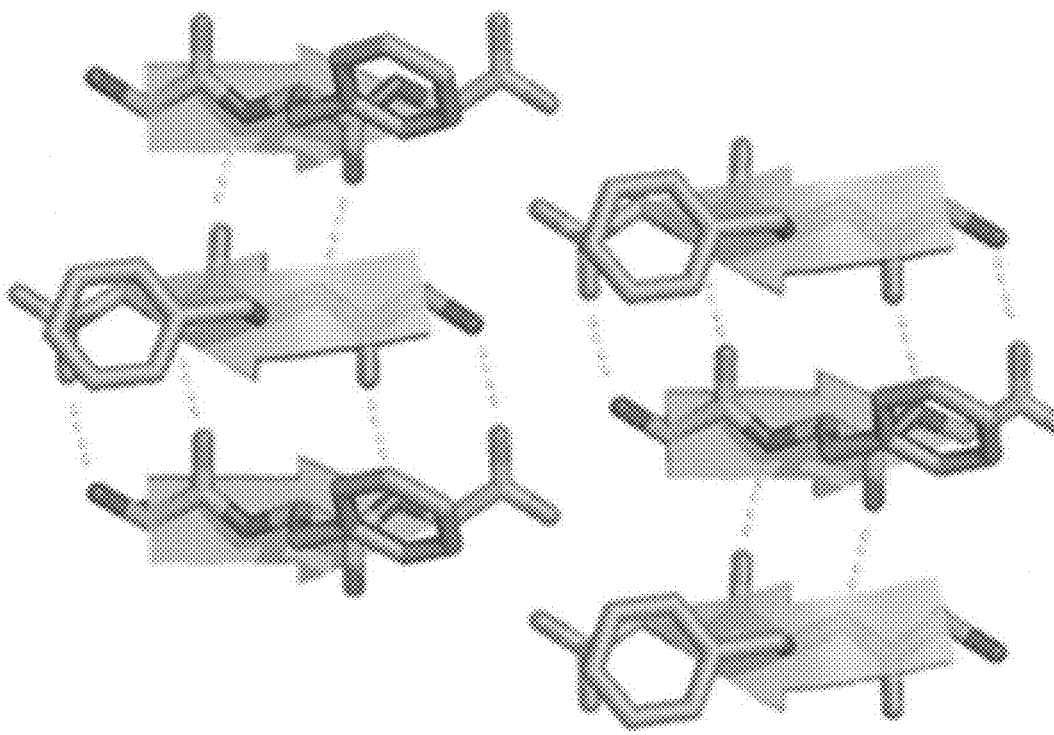

As shown in FIG. 30F, in the crystallographic a-direction, the β-strands of Ala-Phe-Ala were stacked in an antiparallel manner, interacting with the adjacent strands through intermolecular hydrogen bonds incorporating both terminal polar groups and internal amide groups, thereby producing an antiparallel β-sheet conformation.

The tripeptide exhibited two conventional $NH3^+$ ... $^-OOC$ head-to-tail hydrogen bonds, with the third amine hydrogen involving the acetic acid or trifluoroacetic acid moiety. Nearby sheets were connected through head-to-tail H-bonds between polar head groups, generating a 1D layer where all Phe residues are positioned on the same side of the layer. The individual layers stacked to afford a layer-by-layer structure of Ala-Phe-Ala stabilized through van der Waals interactions.

Figure 30G:
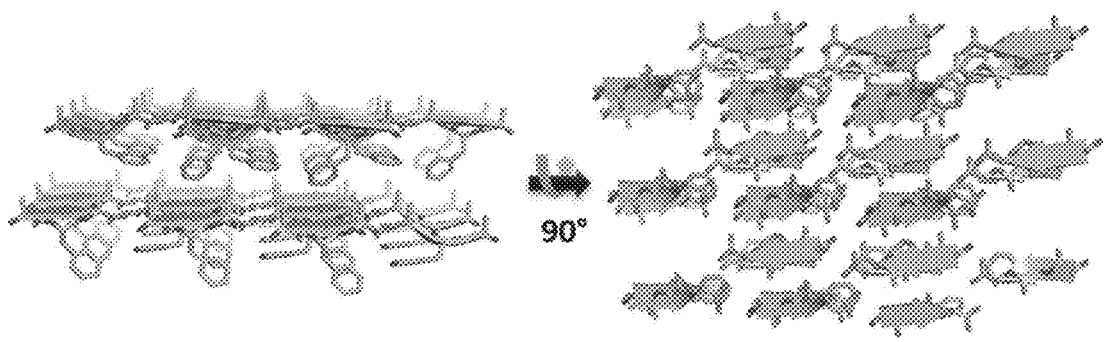

As shown in FIG. 30G, the overall molecular packing of Ala-Phe-Ala comprised a cross-β structure.

Notably, no π-π interactions between Phe residues were observed, neither within cross-strands along the a-direction nor within cross-sheets along the b-direction.

In conclusion, both modified tripeptides, Ala-Phe-Phe and Ala-Phe-Ala, organized into a cross-β structure rather than a cross-helix structure such as in Pro-Phe-Phe.

The experimental data for Ala-Phe-Phe and Ala-Phe-Ala are summarized in Table 2 below.

TABLE 2

Data and refinement statistics for Ala-Phe-Phe and Ala-Phe-Ala

| Crystal data | Ala-The-The | Ala-Phe-Ala |
|---|---|---|
| CCDC | | |
| Diffractometer | Rigaku XtaLabPro | Rigaku XtaLabPro |
| Empirical formula | 2(C21 H25 N3 O4), C2F3O2, O | 2(C15 H21 N3 O4), C2F3O2, C2H4O2, H2O |
| Crystal description | 895.90 | 805.78 |

TABLE 2-continued

Data and refinement statistics for Ala-Phe-Phe and Ala-Phe-Ala

| Crystal data | Ala-The-The | Ala-Phe-Ala |
|---|---|---|
| Formula weight (g/mol) | Colourless wedge prism | Colourless plate |
| Temperature (K) | 100 | 100 |
| Wavelength (Å) | 1.54184 | 1.54184 |
| Crystal system | Triclinic | Monoclinic |
| Space group | P1 | $P2_1$ |
| a (Å) | 9.49980(10) | 9.5010(1) |
| b (Å) | 10.9522(2) | 17.5658(1) |
| c (Å) | 11.9932(2) | 12.1344(1) |
| α (°) | 111.088(2) | 90 |
| β (°) | 99.231(1) | 99.183(1) |
| γ (°) | 90.369(1) | 90 |
| Volume (Å³) | 1146.38(3) | 1999.19(3) |
| Z | 1 | 4 |
| Density calculated (Mg/m³) | 1.298 | 1.339 |
| Absorption coefficient ($mm^{-1}$) | 0.860 | 0.958 |
| F(000) | 471 | 850 |
| Crystal size (mm³) | 0.12 × 0.04 × 0.01 | 0.131 × 0.040 × 0.031 |
| Theta range for data collection (°) | 4.68 to 79.410 | 4.468 to 80.206 |
| Reflection collected (Unique) | 31351(9083) | 44321(8641) |
| R int | 0.0397 | 0.0389 |
| Completeness | 96.9% | 95.5 |
| Data\restraints\parameters | 9083/3/581 | 8641/4/521 |
| Goodness-of-fit on $F^2$ | 1.052 | 1.027 |
| Final R [I > 2σ(I)] | R1 = 0.0505, wR2 = 0.0819 | R1 = 0.339, wR2 = 0.0863 |
| R (all data) | R1 = 0.0814, wR2 = 0.0908 | R1 = 0.0345, wR2 = 0.0867 |
| Largest diff. peak and hole (e · Å⁻³) | 0.757 and −0.385 | 0.333 and −0.223 |

In addition, the self-assembled morphology and secondary structures of the modified tripeptides Phe-Pro-Phe and Phe-Phe-Pro were studied by HRSEM, CD, FTIR and PXRD analysis.

Figure 31A:
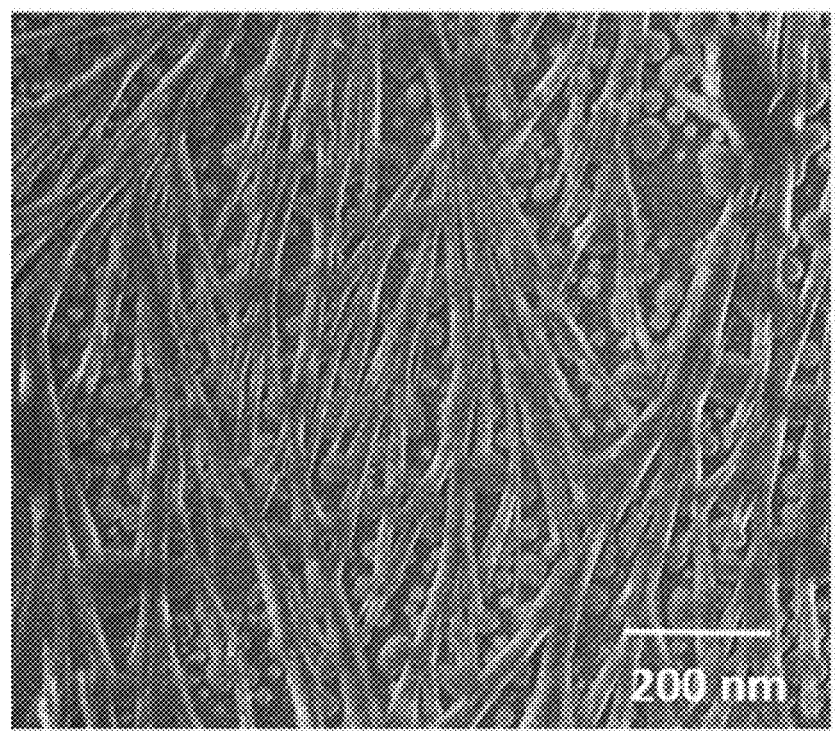
FIGS. 31A-31H present HR-SEM micrographs of Phe-Pro-Phe (FIG. 31A) and Phe-Phe-Pro (FIG. 31E) self-assembled structures (in phosphate buffer at pH 7.4), FTIR spectra of Phe-Pro-Phe (FIG. 31B) and Phe-Phe-Pro (FIG. 31F), CD spectra (in solution) of Phe-Pro-Phe (FIG. 31C) and Phe-Phe-Pro (FIG. 31G), and X-ray diffraction patterns of Phe-Pro-Phe (FIG. 31D) and Phe-Phe-Pro (FIG. 31H).

As shown in FIG. 31A, Phe-Pro-Phe assembled in phosphate buffer at pH 7.4 to produce thin fibers along with spherical morphologies. The length and width of the fibers were much smaller than those of the Pro-Phe-Phe helical fibers.

Figure 31B:
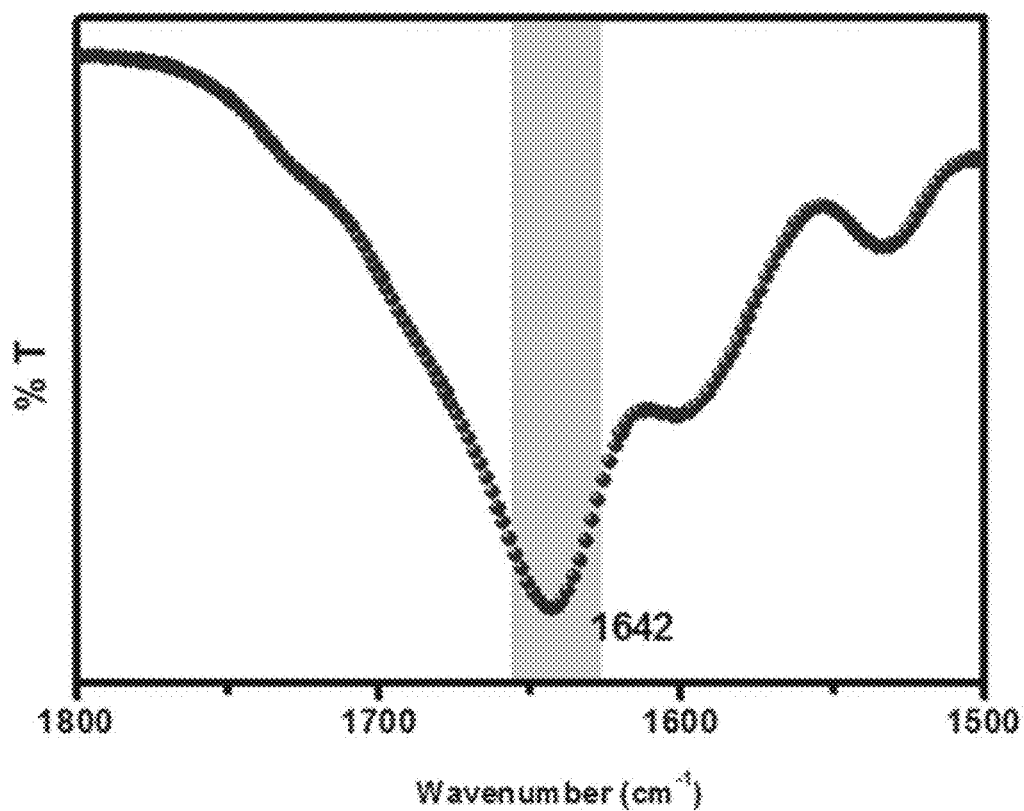

As shown in FIG. 31B, the FTIR spectrum of Phe-Pro-Phe exhibited a sharp amide I band at 1642 $cm^{-1}$.

This result indicates the predominant presence of a β-sheet structure [Cabiaux et al., *J Biol Chem* 264:4928-4938 (1989); Kong & Yu, *Acta Biochim Biophys Sin* 39:549-559 (2007)].

CD analysis was employed to further confirm the secondary structure.

Figure 31C:
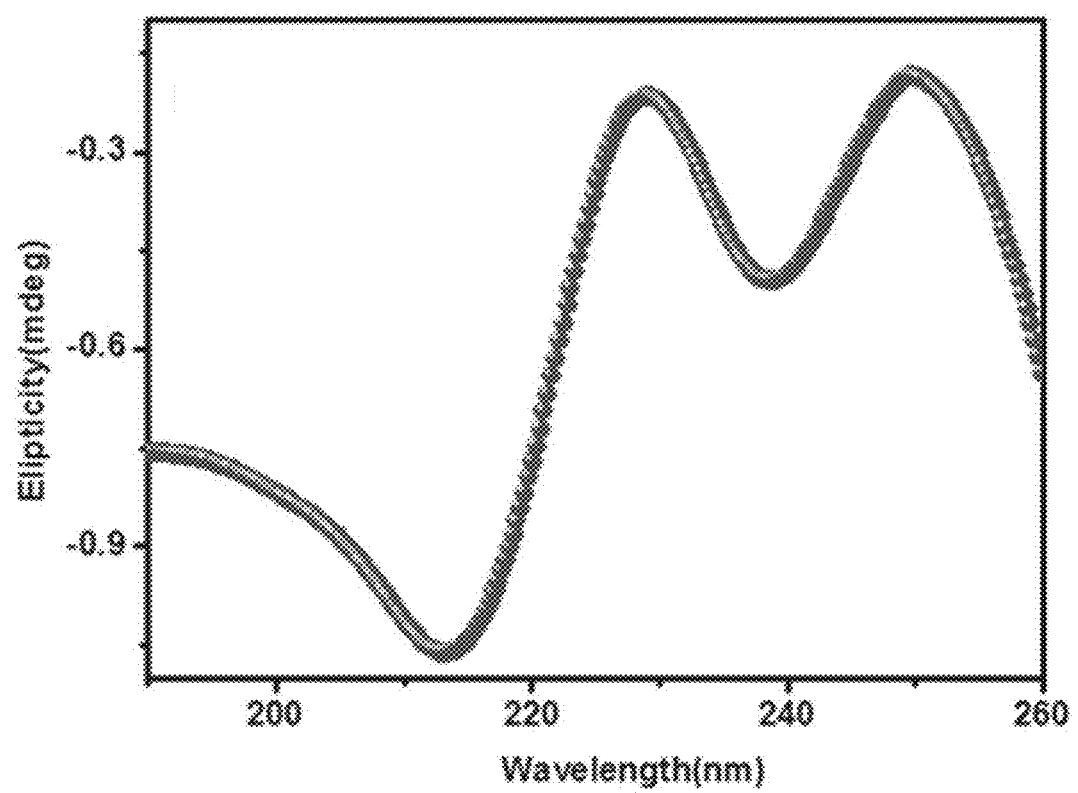

As shown in FIG. 31C, Phe-Pro-Phe self-assemblies exhibited positive peaks near 228 nm, along with a negative maximum at 212 nm.

The positive CD band near 225-235 nm generally arises from the contribution of aromatic residues [Handelman et al., *J Pept Sci* 20:487-493 (2014)]. Previous studies on Phe-Phe-based nanostructures designated these patterns as β-turn structures. The negative CD band indicates the presence of a typical β-sheet signature [Fasman, G. D., *Circular dichroism and the conformational analysis of biomolecules* Plenum Press: New York (1996)].

Thus, both the FTIR and CD analyses clearly indicate the absence of a helical conformation for Phe-Pro-Phe, in contrast to Pro-Phe-Phe.

Figure 31D:
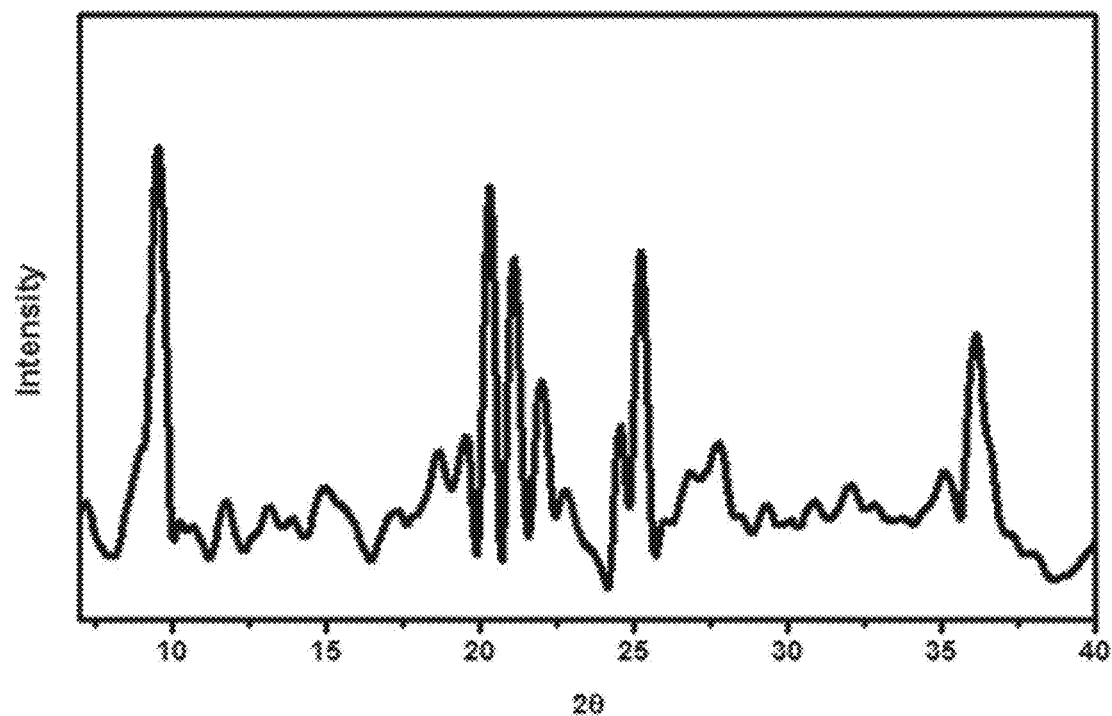

As shown in FIG. 31D, the X-ray diffraction of the dried assembled samples of Phe-Pro-Phe also exhibited a distinctly different pattern from that of Pro-Phe-Phe.

Figure 32:
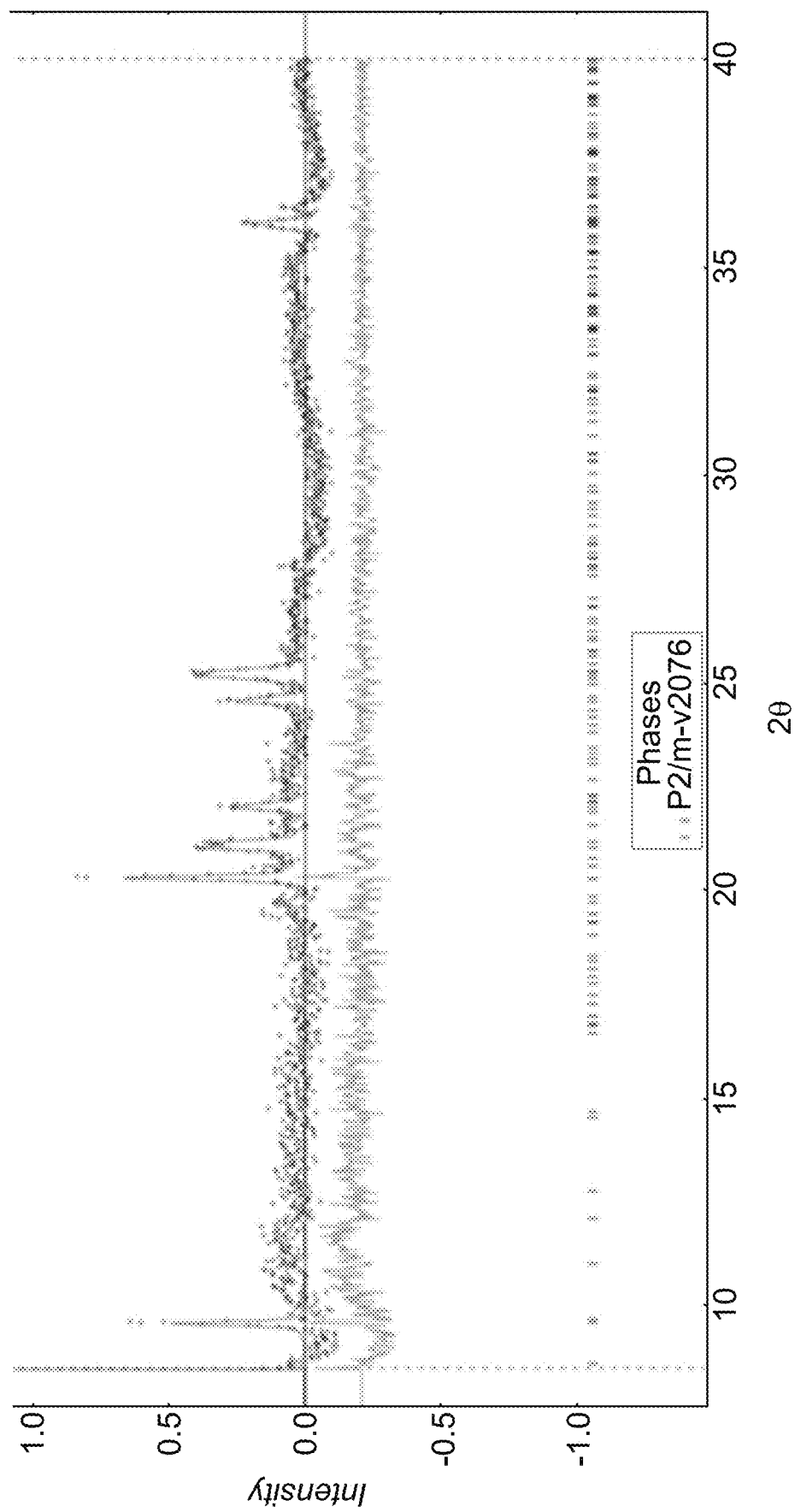
FIG. 32 presents a diffractogram for Phe-Pro-Phe fibers, including observed diffractogram (points marked by +), calculated diffractogram (line fitted to points), and the difference between observed and calculated data (line at bottom).

As shown in FIG. 32, the best match of the powder pattern suggested monoclinic unit cells with a=5.316 Å, b=36.530 Å, c=10.777 Å and β=97.34°, indicating the assembly of distinctive units rather than helices.

Figure 31E:
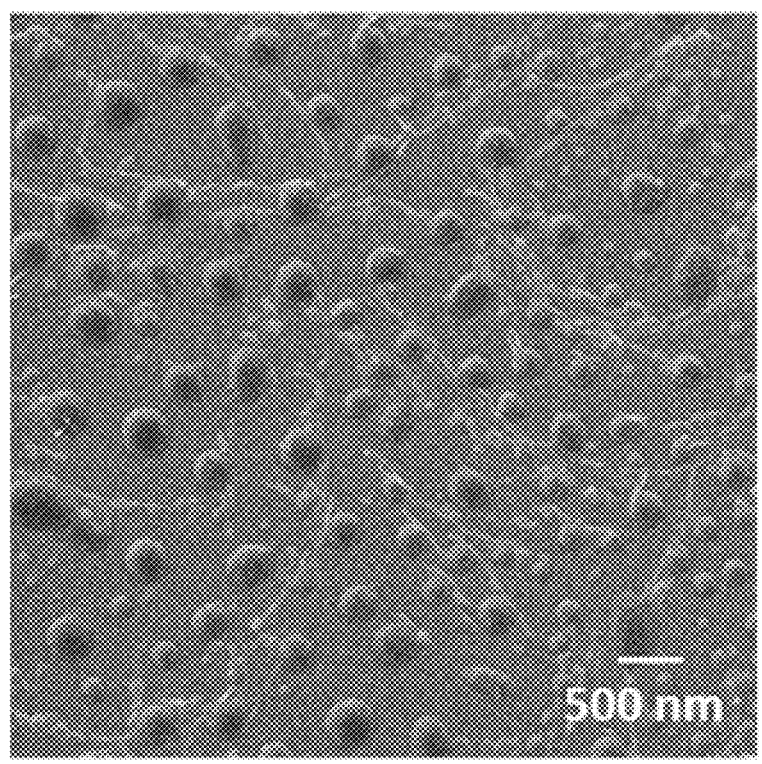

As shown in FIG. 31E, the other modified tripeptide, Phe-Phe-Pro, self-assembled into a spherical nanostructure in phosphate buffer at pH 7.4.

Figure 31F:
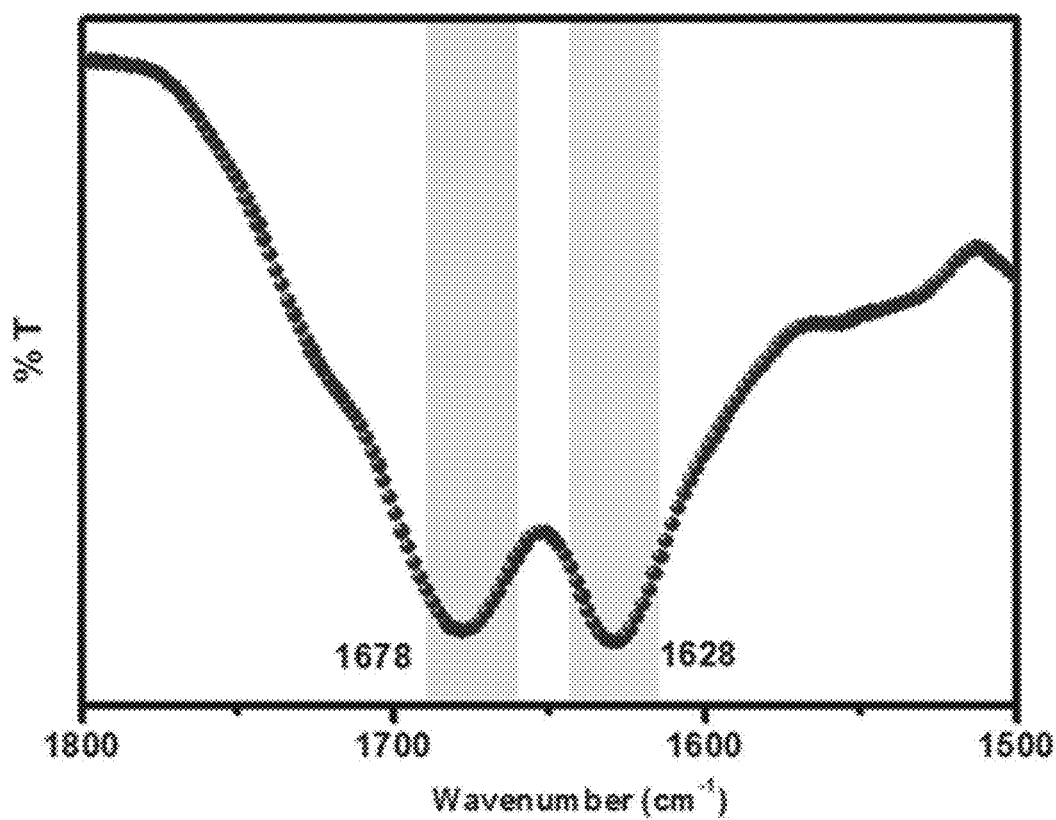

As shown in FIG. 31F, the FTIR spectra of Phe-Phe-Pro exhibited a sharp amide I band at 1628 cm$^{-1}$ along with a peak at 1678 cm$^{-1}$.

This result indicates the predominant presence of a β-sheet secondary structure [Kong & Yu, *Acta Biochim Biophys Sin* 39:549-559 (2007)].

Figure 31G:
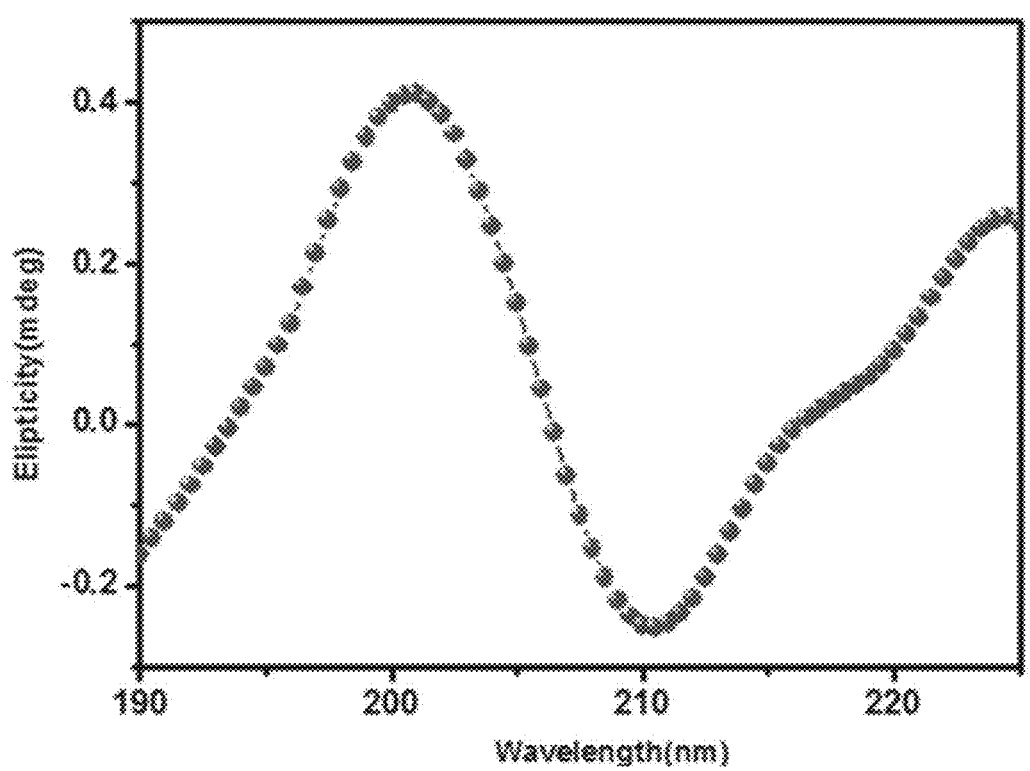

As shown in FIG. 31G, the CD spectra of Phe-Phe-Pro exhibited a negative maximum at 211 nm along with a positive peak at 200 nm, which is typical of a β-sheet like pattern [Nesloney & Kelly, *J Am Chem Soc* 118:5836-5845 (1996)].

Figure 31H:
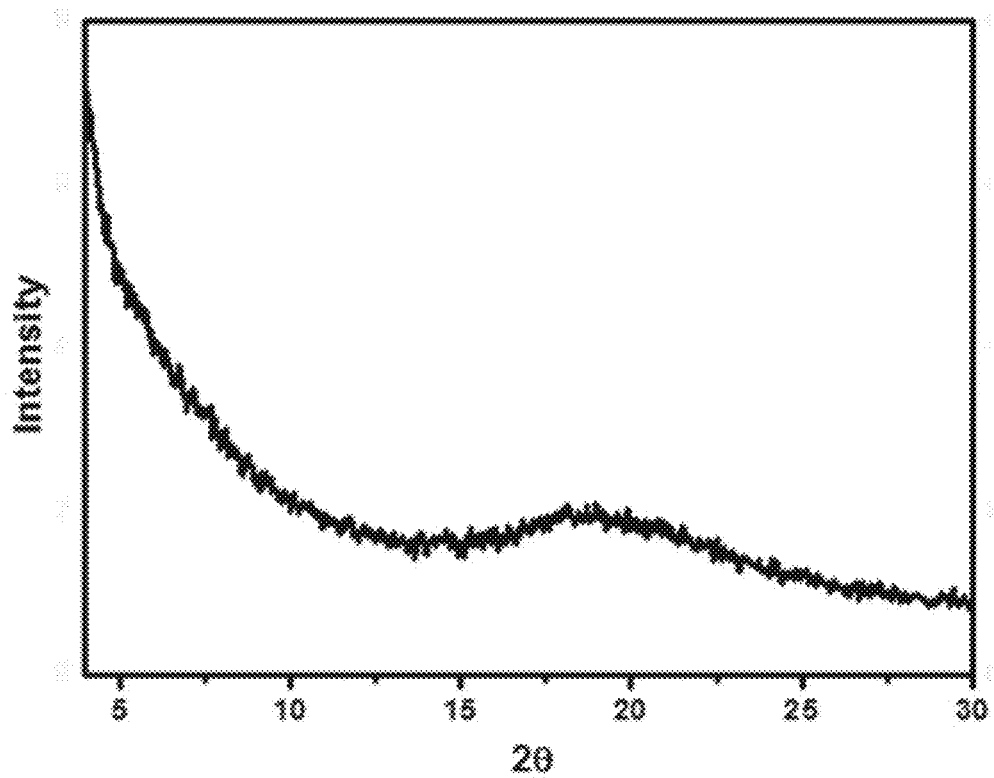

As shown in FIG. 31H, the presence of amorphous materials was determined by PXRD study of the dried sample.

These results indicate that both Phe-Pro-Phe and Phe-Phe-Pro failed to form a cross-helical structure such as that of Pro-Phe-Phe.

Taken together, the above results indicate that modest modifications of Pro-Phe-Phe completely altered the secondary conformation to a β-sheet structure. Moreover, all of the four aforementioned modified peptides are not among the top 400 high aggregation-prone tripeptides as reported by Frederix et al. [*Nat Chem* 7:30-37 (2015)], and show a cross-β organization.

Taken together, these results are consistent with cross-helix secondary structure being associated with high aggregation of short peptides.

Example 3

Piezoelectric and Other Properties of Exemplary Piezoelectric Short Peptides

Pro-Phe-Phe and Hyp-Phe-Phe were prepared as described hereinabove, and their self-assembled structures were calculated (according to procedures described hereinabove) as exhibiting the following electric and mechanical properties:

The dielectric constants (unitless) of Pro-Phe-Phe were $\varepsilon_1$=3.03, $\varepsilon_2$=3.04, $\varepsilon_3$=3.18, and $\varepsilon_r$=3.08; whereas the dielectric constants of Hyp-Phe-Phe were $\varepsilon_1$=2.89, $\varepsilon_2$=3.05, $\varepsilon_{33}$=3.97, and $\varepsilon_r$=3.30.

The elastic stiffness constants of Pro-Phe-Phe were $c_{11}$=11.39 GPa, $c_{22}$=6.33 GPa, $c_{33}$=9.72 GPa, $c_{44}$=−49.43 GPa, $c_{55}$=2.54 GPa, and $c_{66}$=−14.57 GPa; whereas the elastic stiffness constants of Hyp-Phe-Phe were $c_{11}$=9.52 GPa, $c_{22}$=1.35 GPa, $c_{33}$=10.63 GPa, $c_{44}$=−1.69 GPa, $c_{55}$=−3.56 GPa, and $c_{66}$=−0.30 GPa.

The piezoelectric tensors (charge tensor, strain tensor, and voltage tensor) of Pro-Phe-Phe are presented in FIG. 33A and those of Hyp-Phe-Phe are presented in FIG. 33B. Low charge tensor components of up to 22 mC/m$^2$ result in moderate $d_{ij}$ values of up to 3.5 pC/N (picocoloumb per newton).

As with most biomaterials, low dielectric constants of ~3 give significant voltage constants of up to 130 mV m/N ($g_{22}$).

Comparison of the data for Pro-Phe-Phe and Hyp-Phe-Phe indicates that hydroxylation of the proline residue (in Hyp-Phe-Phe) lowers the symmetry of the unit cell (monoclinic to triclinic), thus increasing the number of non-zero piezoelectric constants; results in a five-fold increase in the highest charge tensor value ($e_{33}$=0.1 C/m$^2$); generally decreases individual elastic constants ($c_{ij}$) but within the same range, with the notable exception of $c_{44}$, which decreases by an order of magnitude; and switches $c_{55}$ from positive to negative.

Due to a general increase in $e_{ij}$ values and decrease in $c_{ij}$ values, the predicted piezoelectric strain constant increases significantly, with a $d_{max}$ ($d_{35}$) of −30.34 pC/N, and $d_{22}$ of 19.30 pC/N.

Similarly, as $\varepsilon_r$ values are similar (increased by approximately 7% in Hyp-Phe-Phe), a high voltage constant on the order of 1 Vm/N was calculated, with a $g_{max}$ ($g_{16}$) of 1.043 Vm/N, and $g_{22}$ of −0.715 Vm/N. For comparison, PZT-based ceramics have exhibited voltage constants of 0.250 Vm/N, and values of up to 0.540 Vm/N have been reported for a single crystal of $BiB_3O_6$.

In addition to the abovementioned Pro-Phe-Phe and Hyp-Phe-Phe, additional peptides were found to exhibit a significant piezoelectric effect.

The linear dipeptide (L)Trp-(D)Trp self-assembles into needle-like crystals.

Piezoelectric force microscopy experiments revealed that these supramolecular structures exhibit high piezoelectric properties, with a $d_{33}$ coefficient of 48.1 pC/N (picocoloumb per newton). Poling was not necessary for piezoelectricity.

The (L)Trp-(D(Trp) was rigid and bendable, with a Young's modulus of 10.5 GPa.

Power generators were fabricated using (L)Trp-(D)Trp crystals, deposited over a 0.6×0.6 cm area on a silver substrate. Upon application of a force of 25 N (over a long-term period), a maximal open-circuit voltage of 2.95 V and a maximal short-circuit current of 75 nA were obtained.

In comparison, the capacity of a commercial AA dry cell battery is 1.5 V.

Figure 34:
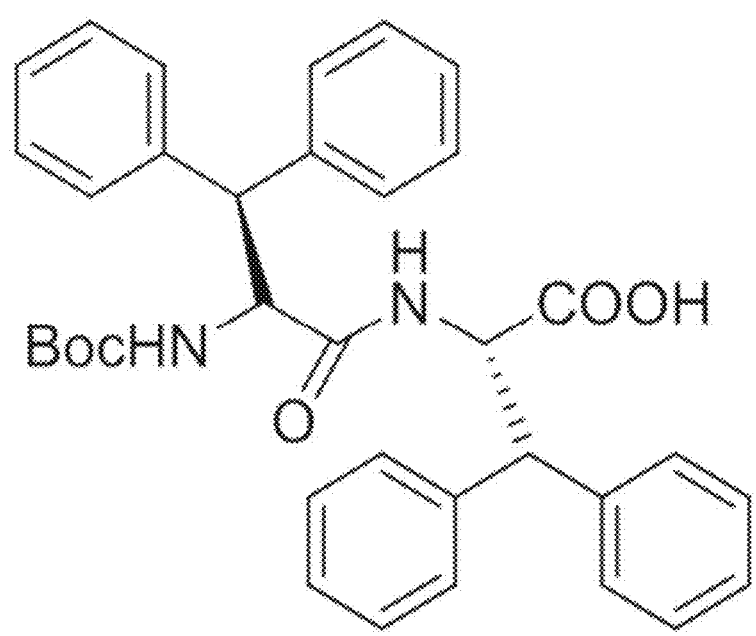
FIG. 34 presents the structure of the exemplary Boc-Dip-Dip peptide.
Figure 35A:
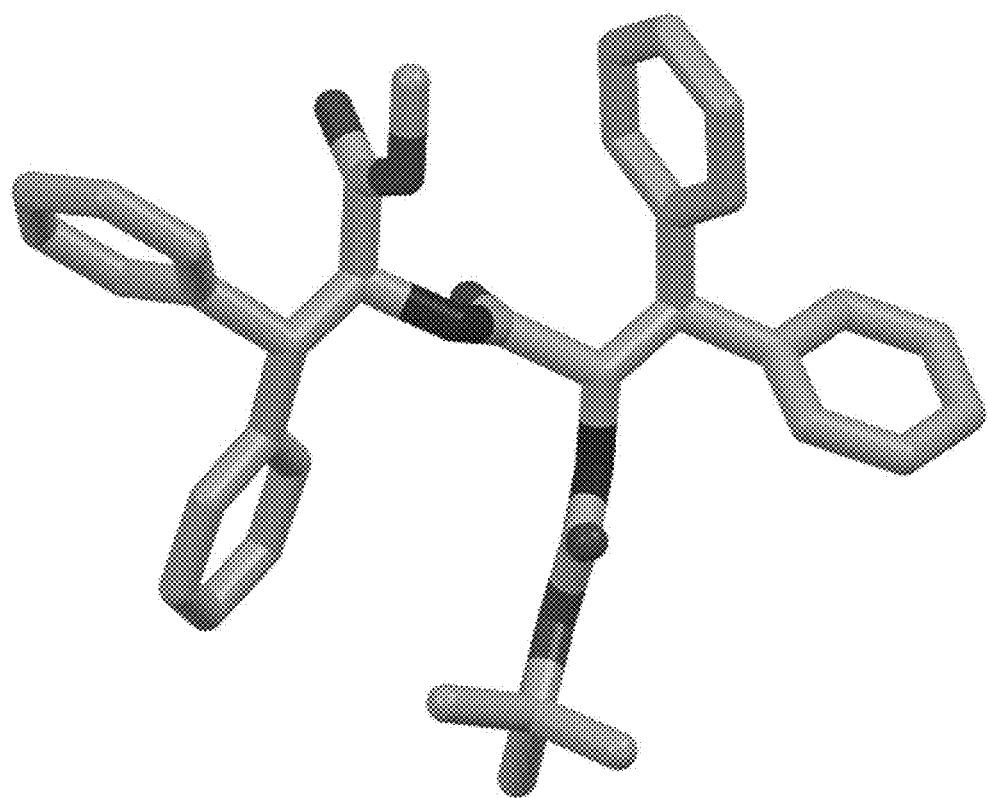
FIGS. 35A-35D presents depictions of the configuration of an asymmetric unit (FIG. 35A), distance of 5,308 Å for π-π interactions (FIG. 35B), and parallel β-sheet organization (FIGS. 35C and 35D) in Boc-Dip-Dip.
Figure 35B:
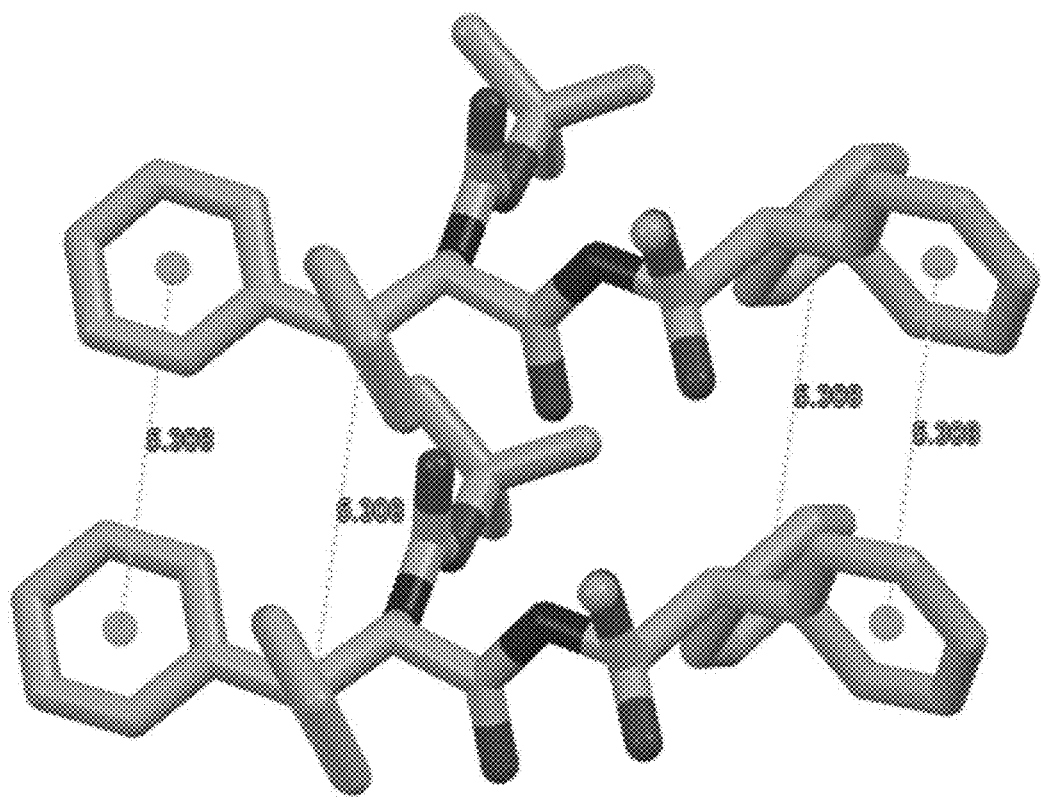
Figure 35C:
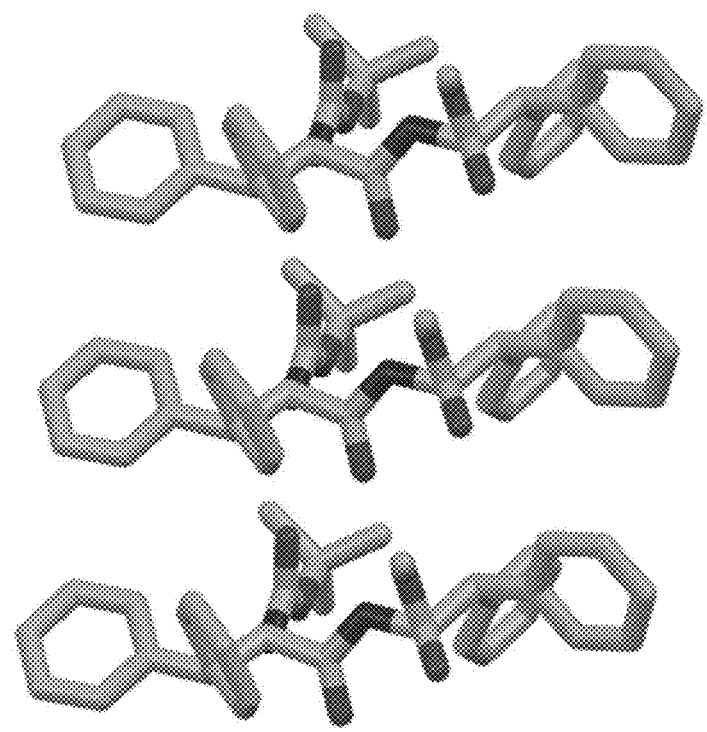
Figure 35D:
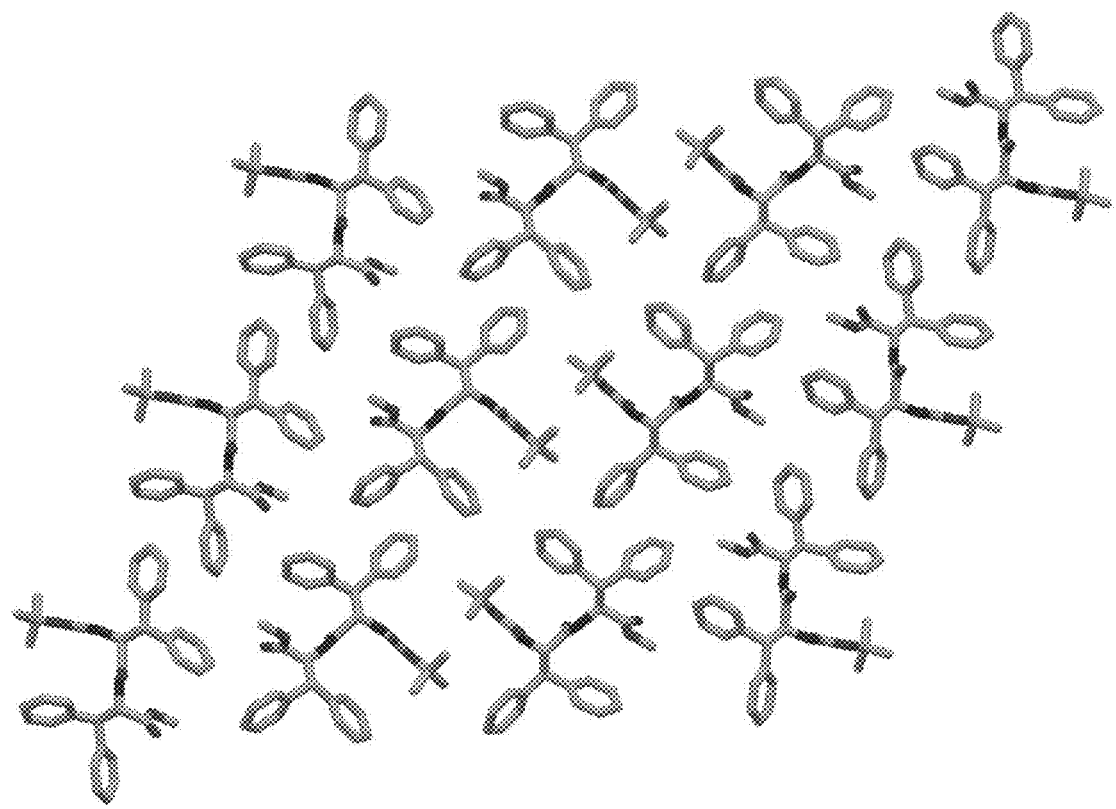

In addition, the highly aromatic (N-terminal-protected) peptide Boc-Dip-Dip (Dip=β,β-diphenyl-alanine), whose structure is depicted in FIG. 34, was prepared. Boc-Dip, NHS and EDC were dissolved in water, then sealed and stirred for ester-activation. After a 24-hour incubation, the concentrated product was washed with water and vacuum dried. The activated Boc-Dip and Dip were dissolved in sodium acetate buffer (pH 5.0, 6.0 mM), sealed and then stirred for a coupling reaction. After a 72-hour incubation, the final product was purified and collected using preparative HPLC, and purity was verified using analytical HPLC, mass spectrometry and NMR, according to procedures such as described by Tao et al. [*Scientific Reports* 5:17509 (2015)].

The Boc-Dip-Dip dipeptide self-assembles into spheres, fibrils and tubes.

As shown in FIGS. 35A-35D, the crystal packing of Boc-Dip-Dip exhibited parallel β-sheet organization stabilized to a considerable extent via π-π interaction of the four aromatic rings of the peptide.

Using indentation-type atomic force microscopy experiments, the Young's modulus of these structures was determined to be 52 GPa, over 3-fold higher than the Young's modulus of superficially similar structures formed by Boc-Phe-Phe (16 GPa).

Figure 36:
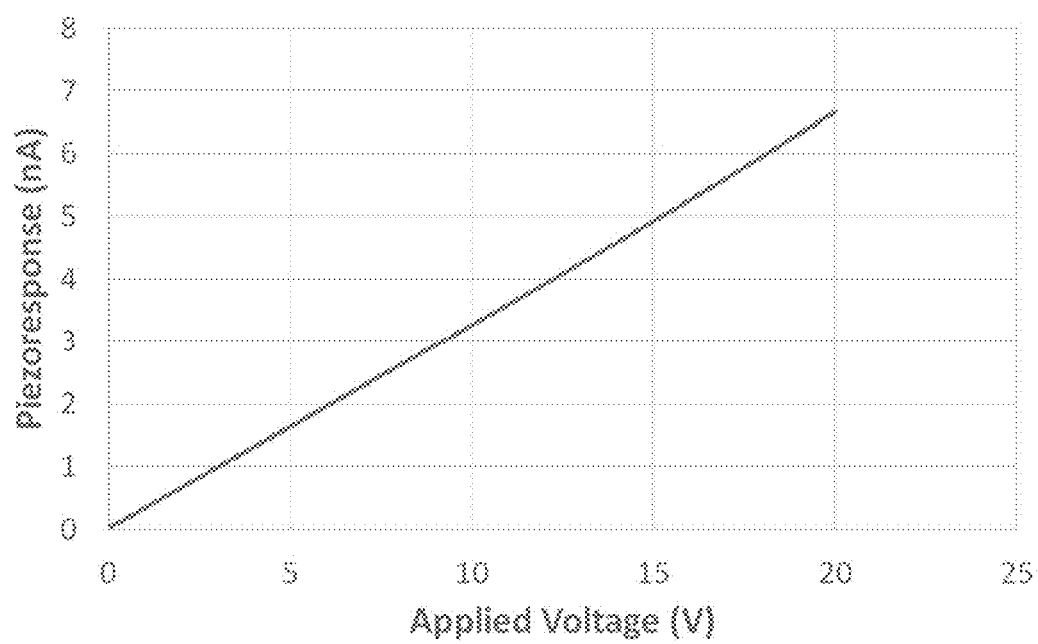
FIG. 36 presents a graph showing the piezoresponse of Boc-Dip-Dip as a function of applied voltage.

As shown in FIG. 36, Boc-Dip-Dip crystals exhibited a linear piezoelectric response (in terms of current per applied voltage), as determined by force microscopy experiments.

Such piezoelectric force microscopy experiments revealed that Boc-Dip-Dip crystals exhibit strong piezoelectric properties, with a $d_{33}$ coefficient of 73.1 pC/N. This value is considerably higher than the $d_{33}$ coefficient of Boc-Phe-Phe (17.9 pC/N) reported by Nguyen et al. [*Nature Commun* 7:13566 (2016)].

These results indicate that the extra aromatic group incorporated into Boc-Dip-Dip (as compared to Boc-Phe-Phe) provides a large increase in both mechanical strength and piezoelectric properties.

Example 4

Exemplary Piezoelectric Short Cyclic Peptides

Figure 37:
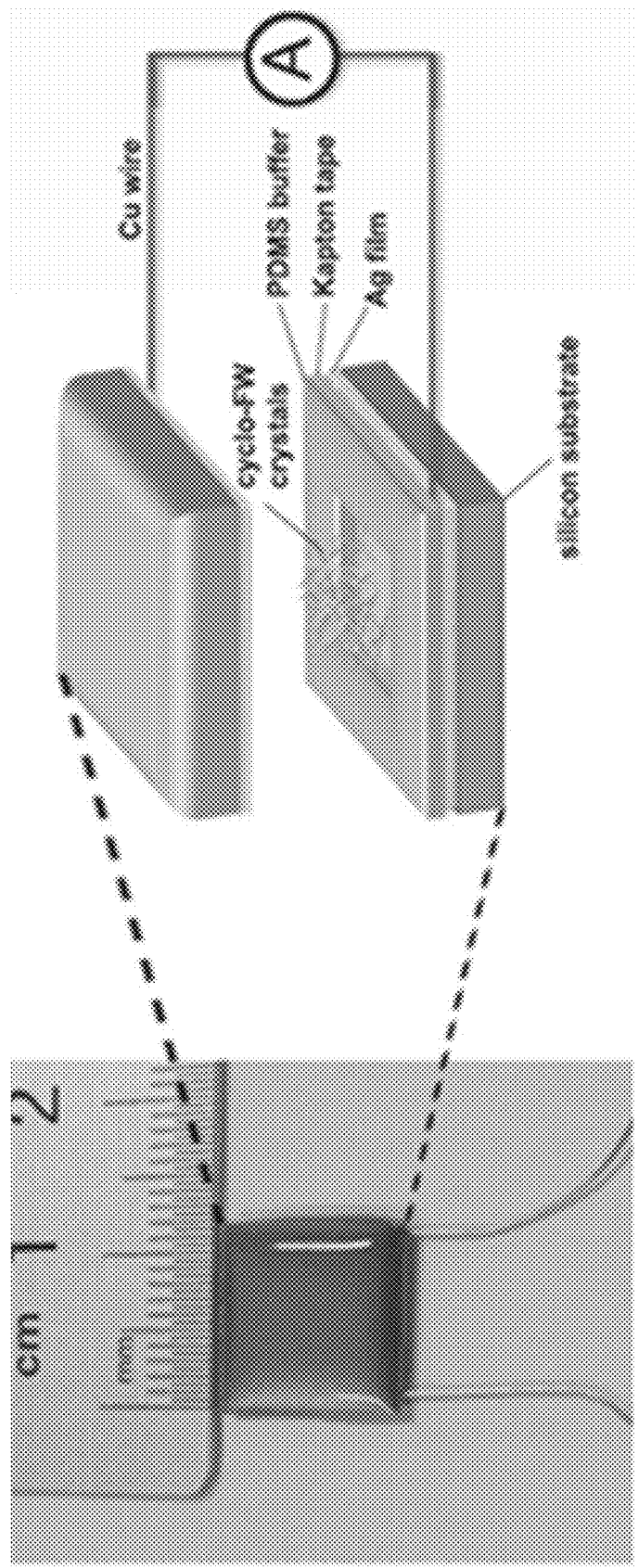
FIG. 37 presents a photograph (right) and schematic depiction (left) of an exemplary generator which functioned as a direct power source, using cyclo-Phe-Trp crystals as the active piezoelectric element.

Cyclo-Phe-Trp crystals were prepared and determined to be characterized by a $P2_12_12_1$ (orthorhombic) space group with parameters a=6.1599(3) Å, b=14.9276(10) Å, c=18.855 (2) Å, V=1733.76(23) Å$^3$, Z=4. In view of the non-centrosymmetric nature of such crystals, the piezoelectric properties of the crystals were assessed by fabricating a minimized power generator comprising cyclo-Phe-Trp as a piezoelectric element, as depicted in FIG. 37. Briefly, as shown therein, the cyclo-Phe-Trp crystals were sandwiched between two silver-coated silicon substrates that connected to an external measuring instrument.

Figure 38A:
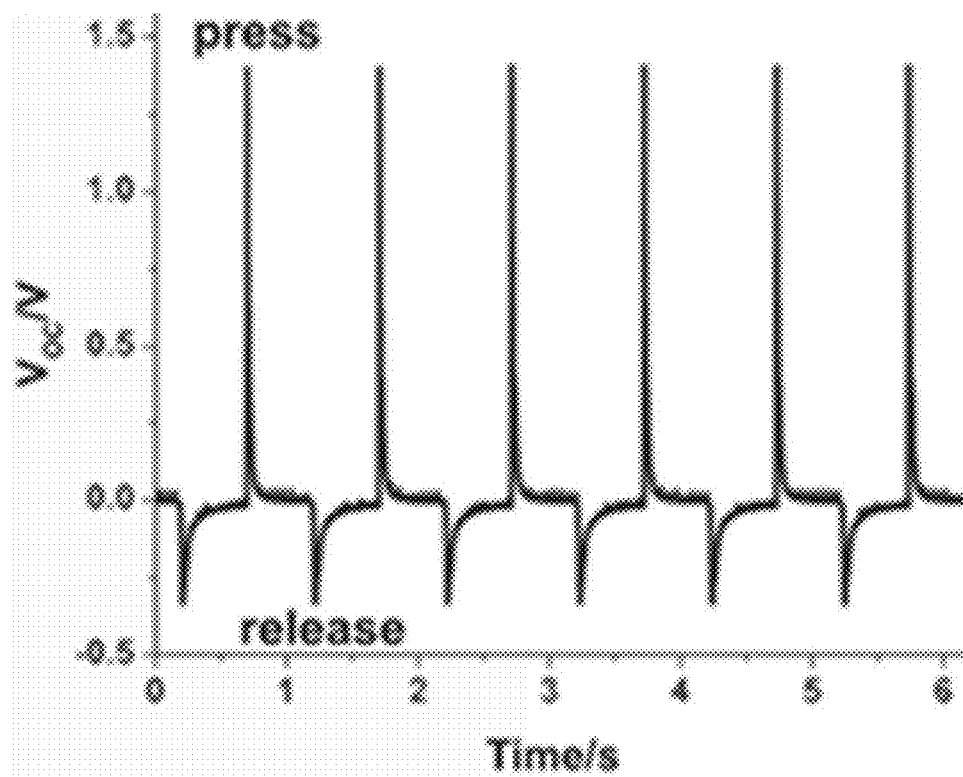
FIGS. 38A and 38B present graphs showing the open-circuit voltage (FIG. 38A) and short-circuit current (FIG. 38B) of the generator shown in FIG. 37 as a function of time (including cycles of pressure and release).

As shown in FIG. 38A, when a periodic compressive force was loaded to the power generator under an applied force of 56 N, the output open-circuit voltage ($V_{oc}$) after offset calibration reached up to 1.4 V.

This value is similar to the value (1.4 V) reported for Phe-Phe microrod arrays [Nguyen et al., *Nature Commun* 7:13566 (2016)] and significantly higher than the reported value (0.45 V) for glycine crystals [Guerin et al., *Nat. Mater.* 17:180-186 (2018)] and M13 bacteriophage (0.4 V) [Lee et al., *Nat Nanotechnol* 7:351-356 (2012)] based piezoelectric power generators.

Figure 38B:
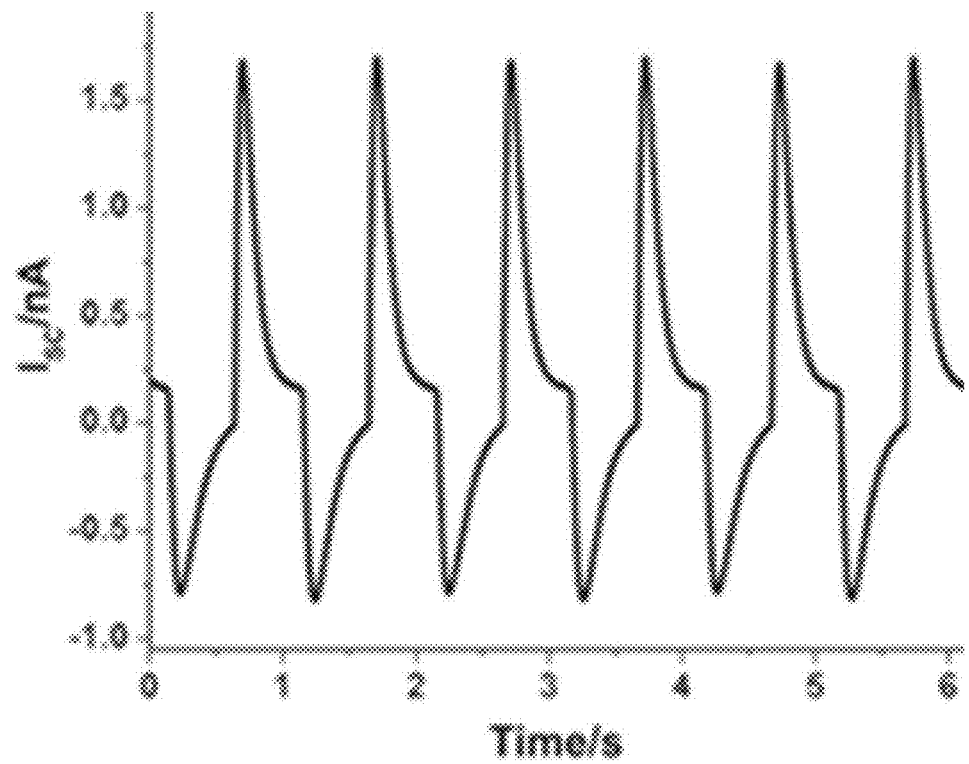

In addition, as shown in FIG. 38B, the short-circuit current ($I_{sc}$) of the cyclo-Phe-Trp-based generator reached 1.75 nA.

Figure 39A:
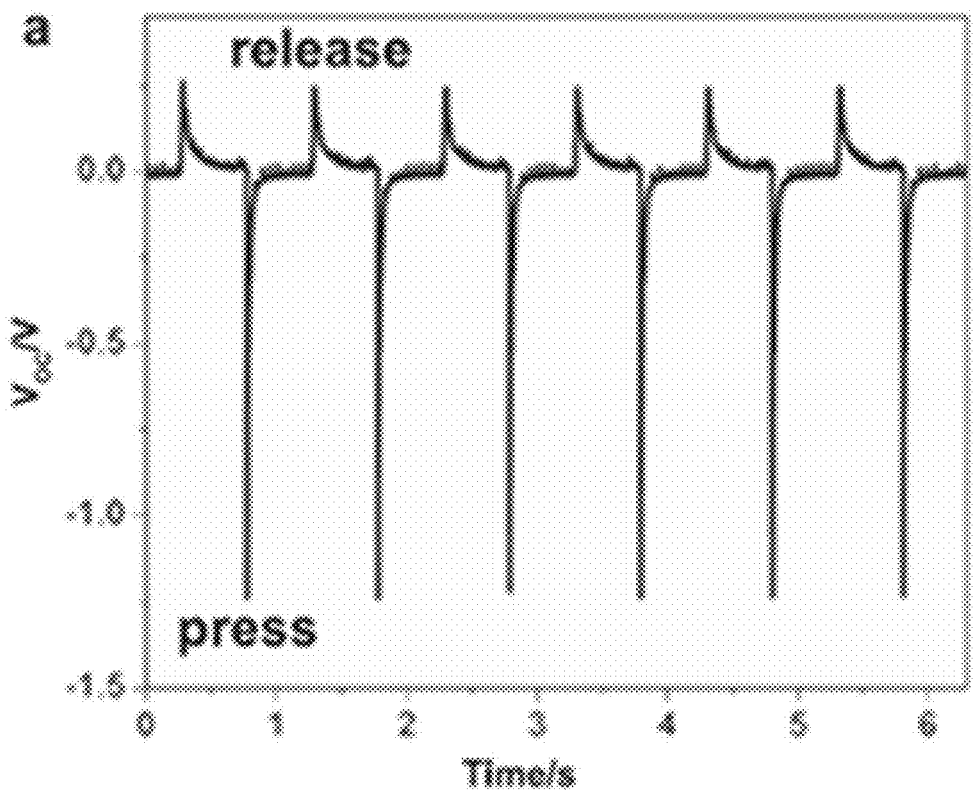
FIGS. 39A and 39B present graphs showing the open-circuit voltage (FIG. 39A) and short-circuit current (FIG. 39B) of the generator shown in FIG. 37 after reversing the connections, as a function of time (including cycles of pressure and release).
Figure 39B:
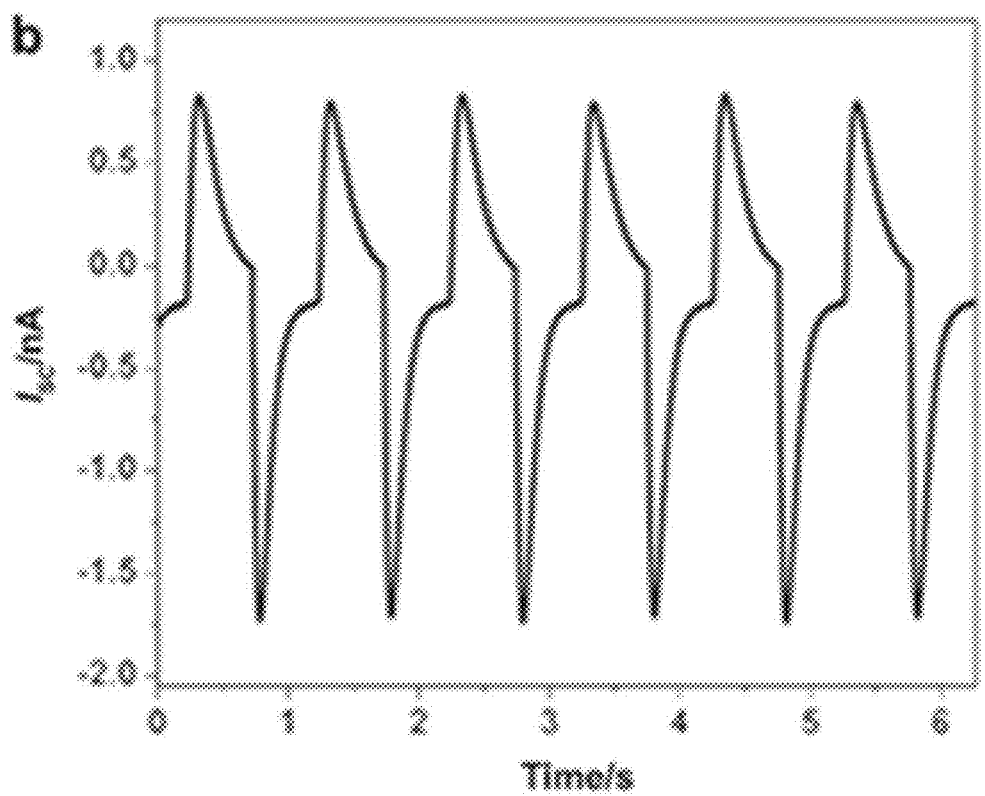

As shown in FIGS. 39A and 39B, opposite output signals were achieved as the connection to the measurement instrument was reversed.

These results exclude possible errors from the variation of contact resistance or parasitic capacitance and confirm that the detected electrical signal indeed emanated from the piezoelectric cyclo-Phe-Trp crystals.

Figure 40:
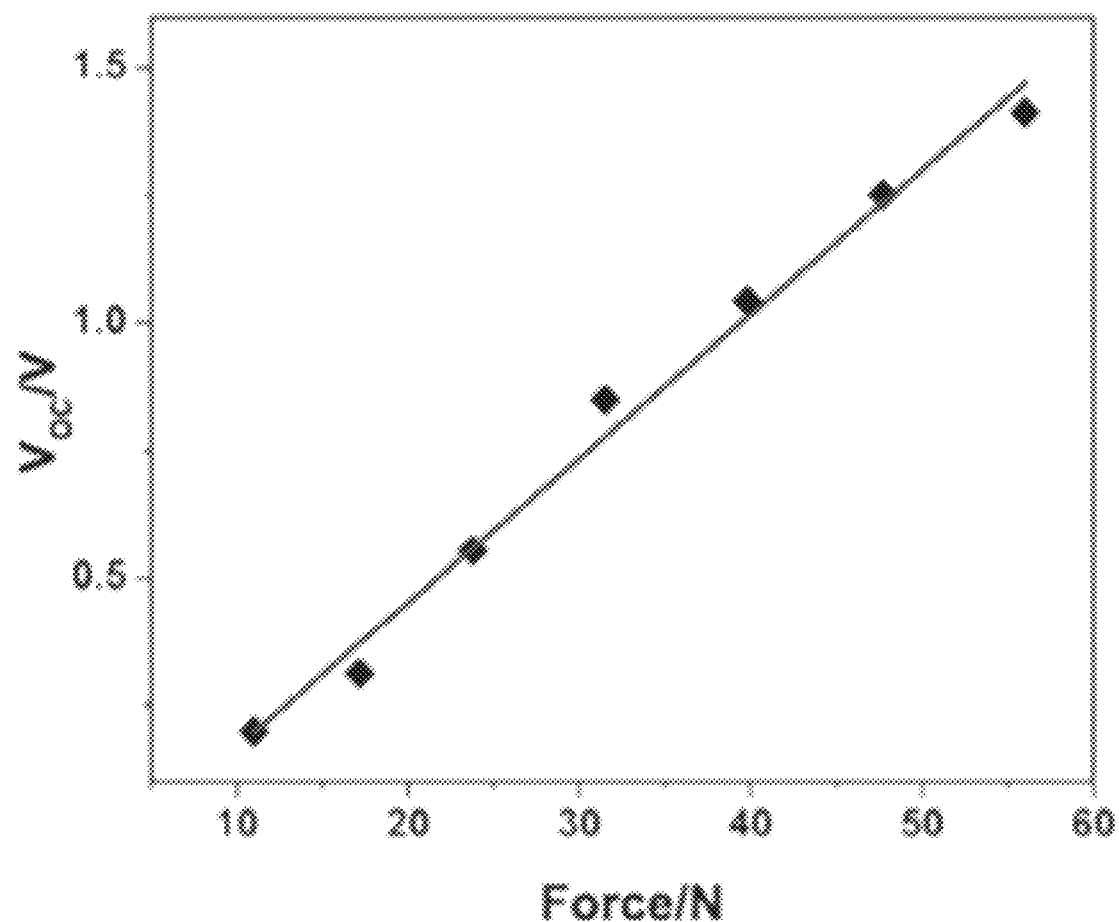
FIG. 40 presents a graph showing the open-circuit voltage of the generator shown in FIG. 37 as a function of applied force.

Furthermore, as shown in FIG. 40, the $V_{oc}$ values were proportional to the applied forces, with a slope of 28 mV/N, thus demonstrating the linear piezoelectricity of the peptide crystals.

Taken together, the above results indicate that cyclo-Phe-Trp crystals exhibit a considerable degree of piezoelectricity.

In addition, cyclic-Gly-Trp crystals were prepared and determined to be characterized by a $P2_1$ (monoclinic) space group with parameters a=7.5382(11) Å, b=6.1498(9) Å, c=12.1288(15) Å, β=91.569(3)°, V=562.06(14) Å$^3$, Z=2.

The piezoelectric properties of the crystals were assessed computationally (according to procedures described hereinabove), and calculated as exhibiting a piezoelectric coefficient ($d_{36}$) of 14.1 pC/N.

Power generators were fabricated using cyclo-Gly-Trp crystals, deposited over a 0.6×0.6 cm area on a silver substrate. Upon application of a force of 65 N, a maximal open-circuit voltage of 1.2 V and a maximal short-circuit current of 1.75 nA were obtained.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A piezoelectric transducer comprising, as a piezoelectric material, a three-dimensional structure, said three-dimensional structure is made of a plurality of peptides, said peptides being self-assembling and said structure being piezoelectric, wherein:
   said three-dimensional structure is characterized by a non-centrosymmetric unit cell, and
   at least a portion, or each, of said plurality of peptides is a peptide of 2 or 3 amino acid residues in length comprising at least two adjacent amino acid residues comprising an aromatic moiety, provided that said plurality of peptides is not consisted of a plurality of Phe-Phe dipeptides,
   said piezoelectric transducer being configured for transforming a mechanical input to an electronic output and/or for transforming an electronic input to a mechanical output.

2. The transducer of claim 1, wherein each of said adjacent amino acid residues that comprise said aromatic moiety is independently a residue of an amino acid selected from the group consisting of phenylalanine (Phe), tyrosine (Tyr), tryptophan (Trp), histidine (His), β,β-diphenylalanine (Dip), naphthylalanine (Nal), and dihydroxyphenylalanine (DOPA).

3. The transducer of claim 1, wherein at least one of said amino acid residues comprises a plurality of non-fused aromatic moieties.

4. The transducer of claim 1, wherein at least a portion, or each, of said plurality of peptides has a helical secondary structure, and said helical secondary structure is characterized by at least one amino acid residue having dihedral angles of psi (ψ) in a range of from −100° to 45° and phi (φ) in a range of from −180° to 15°.

5. The transducer of claim 4, wherein said peptides which have a helical structure comprise peptides having an amino acid sequence selected from the group consisting of Pro-Phe-Phe and Hyp-Phe-Phe.

6. The transducer of claim 1, wherein in at least a portion, or each, of said plurality of peptides, each peptide is a cyclic dipeptide.

7. The transducer of claim 6, wherein said cyclic dipeptide is selected from the group consisting of cyclo-Phe-Phe, and cyclo-Phe-Trp.

8. The transducer of claim 1, wherein at least a portion, or each, of said plurality of peptides is selected from the group consisting of (L)Pro-(L)Phe-(L)Phe, (D)Pro-(D)Phe-(D)Phe, (L)Hyp-(L)Phe-(L)Phe, (D)Hyp-(D)Phe-(D)Phe, Boc-(L)Dip-(L)Dip, Boc-(D)Dip-(D)Dip, (L)Trp-(D)Trp, (D)Trp-(L)Trp, Gly-Trp, cyclo-(L)Phe-(L)Phe, cyclo-(D)Phe-(D)Phe, cyclo-(L)Phe-(L)Trp, and cyclo-(D)Phe-(D)Trp.

9. An electronic device comprising the transducer of claim 1.

10. The device of claim 9, being a medical implant.

11. A peptide having the amino acid sequence Boc-Dip-Dip, wherein Boc is an N-terminal tert-butoxycarbonyl group.

12. A three-dimensional structure made of a plurality of self-assembling peptides, wherein in at least a portion, or each, of said plurality of peptides each peptide is the peptide of claim 11.

13. The three-dimensional structure of claim 12, being a piezoelectric structure.

14. The transducer of claim 1, wherein said piezoelectric material is characterized by a piezoelectric coefficient of at least 20 pC/N.

15. The transducer of claim 1, further comprising an electrical contact for collecting generated electronic output and/or for providing an electric input to the piezoelectric material.

* * * * *